US006448032B1

(12) United States Patent
Wikberg et al.

(10) Patent No.: US 6,448,032 B1
(45) Date of Patent: *Sep. 10, 2002

(54) HUMAN MELANOCYTE STIMULATING HORMONE RECEPTOR POLYPEPTIDE AND DNA

(76) Inventors: Jarl Wikberg, Trillvägen 13, S-905 92 Umeå; Vijay Chhajlani, Stigbergsvägen 8 A, S-752 42 Uppsala, both of (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/387,805
(22) PCT Filed: Aug. 20, 1993
(86) PCT No.: PCT/DK93/00273
§ 371 (c)(1),
(2), (4) Date: Feb. 21, 1995
(87) PCT Pub. No.: WO94/04674
PCT Pub. Date: Mar. 3, 1994

(30) Foreign Application Priority Data

Aug. 21, 1992 (DK) .............................. 1046/92
Sep. 10, 1992 (DK) .............................. 1118/92
May 5, 1993 (DK) .............................. 0528/93

(51) Int. Cl.[7] .................. C07K 14/72; C12N 15/10; C12N 5/10; C12N 15/12
(52) U.S. Cl. .................. 435/69.1; 435/320.1; 435/325; 435/252.3; 435/254.1; 435/69.7; 530/350; 530/306; 530/312; 530/300; 536/23.1; 536/23.4; 536/23.5; 536/24.33
(58) Field of Search .............................. 435/69.1, 240.7, 435/243, 320.1, 325, 254.11, 69.7, 252.3; 530/306, 312, 350; 536/23.1, 23.4, 23.5, 24.33

(56) References Cited

U.S. PATENT DOCUMENTS

| | | | |
|---|---|---|---|
| 5,270,605 A | 12/1993 | Lefrancois et al. | 310/263 |
| 5,280,112 A | * 1/1994 | Cone et al. | 536/23.5 |
| 5,710,265 A | * 2/1994 | Yamada et al. | 536/23.5 |
| 5,532,347 A | 7/1996 | Cone et al. | 536/23.5 |
| 5,554,729 A | * 9/1996 | Cone et al. | 536/23.5 |
| 5,622,860 A | 4/1997 | Yamada et al. | 435/252.3 |
| 5,773,229 A | 6/1998 | Cone et al. | 435/7.21 |
| 5,837,521 A | 11/1998 | Cone et al. | 435/240.1 |
| 5,849,871 A | 12/1998 | Cone et al. | 530/350 |
| 6,100,048 A | 8/2000 | Cone et al. | 435/7.21 |

OTHER PUBLICATIONS

Schiöth, Helgi B. et al., "Characterization of melanocortin receptor subtypes by radioligand binding analysis," *European Journal of Pharmacology* 288: 311–317 (1995).
Kobilka et al. (1987) Nature 329:75–79.*
Shimomura et al. (1990) Nucleic Acids Res. 18(15):4591.*
Oki et al. (1980) Eur. J. Pharmacol. 64:161–164.*
Mertz et al. (1991) Proc. Natl. Acad. Sci. USA 88:8525–8529.*
Pawelek (1976) J. Invest. Dermatol. 66:201–209.*
Reeck et al. (1987) Cell 50:667.*
Zach, Molecular Neurobiology, Sinauer Associates, pp.190–191, 1992.*
Lewin, When does homology mean something else?, Science, 237: 1570, 1987.*
Knapp et al., Proc. Natl. Acad. Sci., USA, 79: 2996–3000, May 1982.*
Susan A. Burchill, et al., "Tyrosinase Synthesis in Different Skin Types and the Effects of α–Melanocyte–Stimulating Hormone and Cyclic AMP," J. Invest. Dermatol. 95:558–561 (Nov. 1990).
Vijay Chhajlani, et al., "Molecular Cloning and Expression of the Human Melanocyte Stimulating Hormone Receptor cDNA," FEBS 309:417–420 (Sep. 1992).
Wesley G. Clark, et al., "Analysis of the Antipyretic Action of α–Melanocyte–Stimulating Hormone in Rabbits," J. Physiol. 359:459–465 (1985).
D. de Wied, "Melanotropins as Neuropeptides," Annals New York Academy of Sciences 680:20–28 (May 1993).
Ira Gantz, et al., "Molecular Cloning of a Novel Melanocortin Receptor," The Journal of Biological Chemistry 268:8246–8250 (Apr. 1993).
Ira Gantz, et al., "Molecular Cloning, Expression, and Gene Localization of a Fourth Melanocortin Receptor," The Journal of Biological Chemistry 268:15174–15179 (Jul. 1993).
G. Ghanem, et al., "Alpha–Melanocyte–Stimulating Hormone Immunoreactivity in Human–Melanoma Metastases Extracts," Pigment Cell Research 2:519–523 (1989).
Gail E. Handelmann, et al., "Alpha–Melanocyte Stimulating Hormone Facilitates Learning of Visual but not Auditory Discriminations," Peptides 4:145–148 (1983).
Melanie E. Hiltz, et al., "Antiinflammatory Activity of a COOH–Terminal Fragment of the Neuropeptide α–MSH," FASB J. 3:2282–2284 (Sep. 1989).
D.J. Hnatowich, "Antibody Radiolabeling, Problems and Promises," Nucl. Med. Biol. 17:49–55 (1990).

(List continued on next page.)

Primary Examiner—Lorraine Spector
Assistant Examiner—Claire M. Kaufman
(74) Attorney, Agent, or Firm—Sterne, Kessler, Goldstein & Fox P.L.L.C.

(57) ABSTRACT

Novel DNA fragments encoding novel polypeptides having properties of melanotropic hormone receptors, especially DNA molecules encoding melanocyte stimulating hormone receptors (MSH receptors), as well as polypeptides which are MSH receptors, are disclosed. The use and engineering of melanotropic hormone receptor DNA and polypeptides for production of monoclonal antibodies for diagnostic and therapeutic purposes, as well as the engineering of drugs, cell lines, vectors, and DNA for therapeutic and diagnostic purposes are also disclosed.

49 Claims, 10 Drawing Sheets

OTHER PUBLICATIONS

Figure 1:
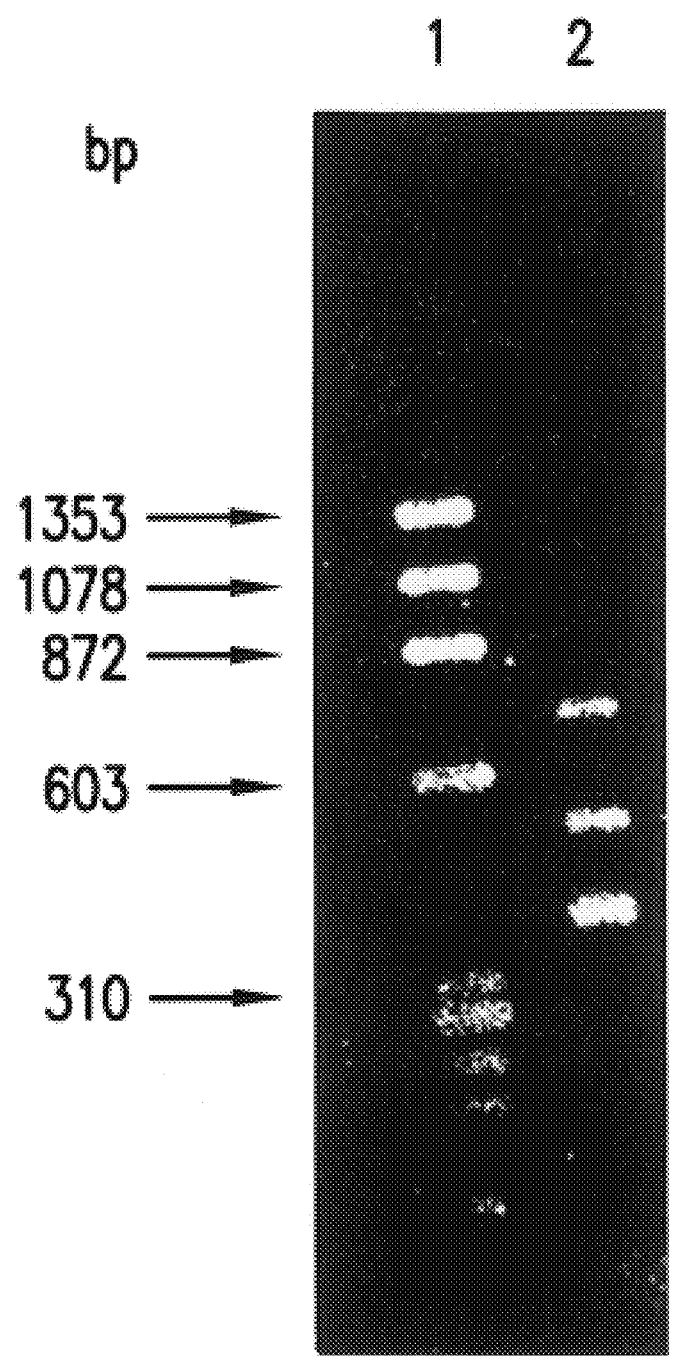

Vincent C. Ho, et al., "Therapy for Cutaneous Melanoma: An Update," J. Am. Acad. of Dermatol. 22:159–176 (Feb. 1990).

Koichiro Kameyama, et al., "Differentiation and the Tumorigenic and Metastatic Phenotype of Murine Melanoma Cells," Int. J. Cancer 45:1151–1158 (1990).

Steven M. Larson, "Biologic Characterization of Melanoma Tumors by Antigen–Specific Targeting of Radiolabeled Anti–Tumor Antibodies," J. of Nuclear Medicine 32:287–291 (Feb. 1991).

Normal Levine, et al., "Induction of Skin Tanning by Subcutaneous Administration of a Potent Synthetic Melanotropin," JAMA 266:2730–2736 (Nov. 1991).

Margaret Ann Liu, et al., "Hormone Conjugated with Antibody to CD3 Mediates Cytotoxic T Cell Lysis of Human Melanoma Cells," Science 239:395–398 (Jan. 1988).

Kathleen G. Mountjoy, et al., "The Cloning of a Family of Genes That Encode the Melanocortin Receptors," Science 257:1248–1251 (Aug. 1992).

John R. Murphy, et al., "Genetic Construction, Expression, and Melanoma–Selective Cytotoxicity of a Diphtheria Toxin–Related α–Melanocyte–Stimulating Hormone Fusion Protein," Proc. Natl. Acad. Sci. USA 83:8258–8262 (Nov. 1986).

Walter Siegrist, et al., "Characterization of Receptors for α–Melanocyte–Stimulating Hormone on Human Melanoma Cells," Cancer Research 49:6352–6358 (Nov. 1989).

Fleur L. Strand, et al., "Melanotropins as Growth Factors," Annals New York Academy of Sciences 680:29–50 (May 1993).

V.A. Sukhanov, et al., "Melanocyte–Stimulating Hormone (α–MSH) Inhibits the Growth of Human Malignant Melanoma Cells With the Induction of Phosphatidly Inositol and Myo–Inositol Phosphate Levels," Biochemistry International 24:625–632 (Jul. 1991).

Jeffrey B. Tatro, et al., "Specific Receptors for α–Melanocyte–Stimulating Hormone Are Widely Distributed in Tissues of Rodents," Endocrinology 121:1900–1907 (1987).

Jeffrey B. Tatro, et al., "Melanotropin Receptors of Murine Melanoma Characterized in Cultured Cells and Demonstrated in Experimental Tumors in Situ," Cancer Research 50:1237–1242 (Feb. 1990).

Jeffrey B. Tatro, et al., "Melanotropin Receptors Demonstrated in Situ in Human Melanoma," J. Clin. Invest. 85:1825–1832 (Jun. 1990).

Jeffrey B. Tatro, et al., "Interaction of an α–Melanoctye–Stimulating Hormone–Diphtheria Toxin Fusion Protein With Melanotropin Receptors in Human Melanoma Metastases," Cancer Research 52:2545–2548 (May 1992).

Jane L. Veith, et al., "Effects of MSH/ACTH 4–10 on Memory, Attention and Endogenous Hormone Levels in Women," Physiology & Behavior 20:43–50 (1978).

Marcia M. Ward, et al., MSH/ACTH 4–10 in Men and Women: Effects Upon Performance of an Attention and Memory Task, Physiology & Behavior 22:669–673 (1979).

Zilong Wen, et al., "Diphtheria Toxin–Related α–Melanocyte–Stimulating Hormone Fusion Toxin," The Journal of Biological Chemistry 266:12289–12293 (1991).

Marianne S. Wright, et al., "Cloning Strategies for Peptide Hormone Receptors," Acta Endocrinologica 126:97–104 (1992).

Chhajlani, V. et al., "Molecular Cloning of a Novel Human Melanocortin Receptor," *Biochemical and Biophysical Research Communications* 195(2): 866–873 (Sep., 1993).

* cited by examiner

HUMAN MELANOCYTE STIMULATING HORMONE RECEPTOR POLYPEPTIDE AND DNA

The present application claims priority to International Application No. PCT/DK93/00273, filed Aug. 20, 1993, the content of which is hereby incorporated by reference in its entirety.

FIELD OF THE INVENTION

The present invention relates to a DNA fragment encoding the human melanocyte stimulating hormone receptor (MSH receptor) or an analogue or subsequence thereof. The DNA fragment contains an open reading frame of 951 bp which codes for a polypeptide of 317 amino acids, said DNA fragment as well as its analogues, subsequences or modifications constitute an important aspect of the invention. The DNA fragment has been expressed in an eukaryotic cell line and the expressed protein has been found to have properties identical to that of a native MSH receptor. The invention also relates to a DNA fragment encoding a subtype of the human MSH receptor (in this application designated MC-2) which contains an open reading frame of 975 bp which codes for a polypeptide of 325 amino acids, said DNA fragment as well as its analogues, subsequences or modifications also constitute an important aspect of the invention. This DNA fragment has also been expressed in a eukaryotic cell line and the expressed protein has been found to have properties similar to that of an MSH receptor subtype.

The invention also relates to a polypeptide encoded by a DNA fragment of the invention and to analogues and subsequences of said polypeptide. Furthermore, the invention relates to the use of the DNA fragments or analogues or subsequences thereof, and to the use of polypeptides of the invention encoded by the DNA fragments of the invention. Especially interesting is the use of the polypeptides of the invention which have MSH receptor activity. The use of the polypeptides of the invention or analogues or subsequences thereof for generation of antibodies constitutes yet another aspect of the invention. Also, the invention relates to diagnostic and therapeutic methods and diagnostic and therapeutic agents for use in the diagnosis and treatment of MSH receptor expressing disease conditions such as vitiligo, melanoma, skin cancer, pyretic conditions, inflammatory conditions and nociceptive conditions, catatonic conditions and impaired memory conditions, and to methods for detecting and quantitating the MSH receptor. In addition, the invention provides methods for testing substances capable of interfering with the activity of the MSH receptor and methods for treatment of MSH receptor expressing disease conditions. The patent application also relates to the use of the MSH receptor coding fragments or the MSH receptor during non-disease conditions for the control or diagnosis and/or determination and/or production control of skin and/or hair and/or fur colour in man and/or animals. Moreover, the patent application relates to the elucidation of the structure of the MSH receptor in three dimensions by the utilization of computer modelling methods and/or by application of structure analysis by crystallo-graphic approaches and/or NMR (Nuclear Magnetic Resonance) and to the use of the knowledge of the receptor structure for the design of drugs with binding affinity for the MSH receptor and/or its subtype (MC-2).

The present invention which comprises a DNA fragment encoding the MSH receptor or analogues thereof and the application of these and in this connection methods for identifying products which pertains to the MSH receptor and/or its biological functions constitutes significant contributions which will become useful for biotechnological, pharmaceutical, medical and veterinary practices. As a background to the uses of a DNA fragment and analogues and subsequences thereof and the application of these, some of the most important facts regarding the MSH receptor and its biological functions in man and animals are summarized below.

GENERAL BACKGROUND

Although information existed regarding the MSH receptor (reviewed below), the structure of the MSH receptor gene as well as the primary amino acid sequence of the MSH receptor has not been known before the priority date of the present patent application. As appears from the following, the MSH receptor is a very important receptor with a number of different functions such as anti-inflammatory and antipyretic function and involved in a number of diseases such as melanoma and skin cancer and moreover, it is having an important role in the control of skin, hair and fur colour in man and animals.

MSH Receptor and Its Biological Functions

The MSH receptor belongs to a large class of receptors showing functional and structural similarities. These receptors mediate their cellular effects via coupling proteins termed guanine nucleotide regulatory proteins (G-proteins), of which several types are known (e.g. $G_s$, $G_i$, $G_k$ and others). The MSH receptor is a cell membrane bound protein which serves as a recognition site for α-MSH (melanocyte stimulating hormone). The term MSH relates to several peptides among which α-MSH, β-MSH and γ-MSH may be mentioned; the α-MSH generally showing the largest activity. These hormones are generally referred to as melanotropic hormones to which also the ACTH (adreno-corticotropic hormone) belongs as well as a number of related peptides, being present in man and animals. In the present patent application, peptides which have binding affinity for MSH receptors will collectively be referred to as MSH peptides or MSH receptor ligands. Upon binding of MSH receptor ligands to the MSH receptor, an activation of the receptor ensues which leads to altered activity of the cell in which the receptor is located. MSH receptors are known to be present in melanocytes which are pigment cells and in humans give the skin a varying amount of dark pigmentation and which have a role in protecting the skin from UV-radiation. In animals, melanocytes also have a role in skin pigmentation. In both animals and man changes in skin colour are at least partly mediated by melanocytes and these changes are also partly regulated by the degree of activation of MSH receptors by the peptide hormones that bind to the MSH receptor (Nordlund 1991; Levine 1991).

MSH receptors may also be localized in cell types other than melanocytes (Tatro 1987) where they may have other types of important physiological roles. α-MSH is known to be produced in certain areas of the brain, such as the hypothalamus, corpus amygdaloideum and cerebral cortex. Moreover, proopiomelanocortin, which is the precursor molecule for α-MSH, is found in lymphocytes of the thymus and spleen, neutrophils, placenta, ovary as well as in the epidermis (Nordlund 1991). There is evidence that by acting on MSH receptors, α-MSH may have roles in (i) mediating neurotransmitter effects in the CNS, (ii) participating in endocrine regulation, (iii) modulating immune-inflammatory responses, besides (iv) regulating the skin pigmentation, as mentioned above (Nordlund 1991, Levine 1991). MSH receptors perform various functions in neurochemical processes, such as the induction of antinociceptive effects, the perturbation of grooming behaviour, the alteration of stretch and yawn reflexes and the potentiation of catatonic states (Hirsh and O'Donohue 1986). Moreover, MSH receptors are implicated to have a function in the enhancement of visual and verbal learning (Veith et al. 1978; Ward et al. 1979, Handelman et al. 1983). The role for MSH receptors in endocrine function is indicated, for example, by observations that α-MSH may affect cortisol secretion from the adrenal gland, and increase plasma levels of growth hormone, luteinizing hormone and follicle-stimulating hormone (Reid et al. 1984).

MSH receptors also seem to be mediating the powerful antipyretic effect caused by α-MSH (Clark et al. 1985) as well as the anti-inflammatory actions induced by α-MSH (Rheins et al. 30 1989). Central MSH receptors are also involved in the mediation of anti-convulsive effects since MSH peptides exert anti-epileptic effects (De Wied 1993). Moreover, MSH receptors seem to mediate the growth factor effect of MSH peptides which mediates accelerated and enhanced nerve generation and muscle reinnervation after peripheral nerve injury (Strand et al. 1993).

MSH Receptors on Melanoma Cells

Melanoma cell lines are derived from immortalized melanocytes. Melanocytes are clinically the starting point of malignant melanoma (review ed below). MSH receptors are present on many such melanoma cell lines, the reported frequency in different cell lines being more than 70% (Tatro et al. 1990a). In experimental melanoma, differentiation, tumorigenicity and metastatic potential of the melanoma are influenced by MSH (Kameyama et al. 1990). Moreover, α-MSH immunoreactivity has been demonstrated to be present in human melanoma metastases (Ghanem et al. 1989) indicating the possibility that locally formed melanotropic activity has a role in the pathogenesis of melanoma.

The presence of MSH receptors on melanoma cell lines suggests that endogenous α-MSH, the major know n form of circulating melanotropin in mammals, may modulate melanoma cell activity in vivo. The demonstration of specific binding sites in melanoma tumours does not prove that these are linked to cellular response systems in vivo, but this seems highly likely in view of the close relationship between binding and biological responses in cultured melanoma cells (Tatro et al. 1990b). Evidence suggests that α-MSH may modulate proliferation and ability of melanoma cells to establish metastatic colonies (Lerner et al. 1989; Abdel-Malek et al. 1986).

It is well recognized that in mammalian melanocytes and melanoma cells α-MSH acts through MSH receptor on an intracellular pathway that involves the activation of adenylate cyclase (Tatro et al. 1990b). This leads to an increase in the production of cyclic AMP which in turn induces tyrosinase, a key enzyme in the melanin biosynthesis. However, there is evidence that melanotropins after binding to the MSH receptor increase the intracellular calcium (Mac Neil et al. 1990). It is conceivable that this effect is due to the fact that MSH/MSH receptor complex activates phospholipase C (PLC), which then acts to produce inositol 1,4,5-trisphosphate, which then in turn triggers mobilization of intracellular calcium. This proposition is due to the fact that receptor mediated activation of PLC is a G-protein linked event, and that it has been shown that receptors may simultaneously, e.g. in a promiscuous way, act via several of the known G-protein linked metabolic pathways (Traiffort et al. 1992 and Gudermann et al. 1992). Activation of phospholipase C also leads to the production of diacylglycerol, the activator of protein kinase C. Indeed, it has recently been shown that MSH can activate protein kinase C (Buffey et al. 1992). Two other G-protein coupled receptors, namely the $\alpha_{1b}$-adrenergic receptor and serotonin receptor, which are also coupled through the above mentioned second messenger system, are shown to be protooncogenic (Allen et al. 1991; Julius et al. 1989), thus further indicating the possibility that MSH receptor may have a pathogenic role in melanoma. Moreover, melanotropins are shown to induce expression of the growth associated oncogene c-fos (Hart et al. 1989) further supporting this notion. Note also Sukhanov et al. (1991).

Malignant Melanoma

Malignant melanoma (melanocarcinoma) is a malignancy derived from melanocytes. About 1% of all malignant tumours are malignant melanomas. The incidence of malignant melanoma is increasing rapidly. During the last decades the incidence has approximately doubled every 10 years with both sexes being affected equally. Malignant melanoma can develop at every site of the skin. There are sites of predilection: feet followed by head and neck. Infrequent sites are the genital organs, perineum, perianal region and mucous membranes. The tumour has a high incidence of metastasis to adjacent skin and regional lymph nodes. Haematogenous metastasis may also occur.

The main factor for the development of malignant melanoma is exposure to sunlight. The people who are mainly affected are those who have fair skin that can be easily damaged by the sunlight. Despite various therapeutic regimes the 5 year survival in melanoma with distant metastasis is only 5% and with regional metastasis it is 43% (Roses et al. 1991). Existing clinically approved therapies, besides surgical removal of lesions, are non-specific and include limb perfusion, chemotherapy, immunotherapy, radiotherapy and hormonal therapy (Ho et al. 1990). Radiopharmaceuticals such as iodoquinoline (Lambrecht et al. 1984), iodothiouracil (Coderre et al. 1986) and N-(2-diethylaminoethyl)-4-iodobenzamide (Michelot et al. 1991) have been used for the diagnosis and therapy of melanoma, albeit with very limited success. Another approach for the diagnosis and therapy of melanoma is to use radiolabelled monoclonal antibodies against melanoma associated antigens (Eary et al. 1989; Larson 1991). This poses the problem of having a true melanoma associated antigen. Also, different antigens are expressed based on the developmental stage of the melanoma tumour, and different tumour sites in the body may be expressing different antigens. This would require the use of a mixture of monoclonal antibodies, all of them with very high specificity. The composition of such a mixture will vary between patients and between different tumour stages of the same patient. All this would be very difficult to achieve. Previous work has shown that MSH receptors are detectable in melanoma metastases of about 80% of human patients (see Tatro et al. 1992).

MSH receptors on the melanoma cells have been considered as potential targets for novel drugs useful for treatment of the disease. Diphtheria toxin and α-MSH fusion protein have been constructed and shown to be selectively toxic for MSH receptor bearing cells in vitro by a targeted delivery of the diphtheria toxin (Murphy et al. 1986; Wen et al. 1991; Tatro et al. 1992). In another approach MSH was coupled with an antibody directed towards the CD3 receptor of cytotoxic T cells. The complex was shown to mediate cell lysis of melanoma cells in vitro. The MSH moiety binds to the MSH receptor of the melanoma cells whereas the antibody tags CD3 bearing cytotoxic T-cells which mediate lysis of the melanoma cell (Liu et al. 1988).

MSH Receptor and Skin Tanning and Control of Hair and Fur Colour

Endogenous and exogenous melanotropins are suggested to enhance human cutaneous pigmentation in vivo (Levine 1991; Mulligan et al. 1982; Lerener et al. 1961). The mechanism of action by which MSH and other melanotropins stimulate melanogenesis is well studied. The melanotropins bind MSH receptors on melanocytes and result in the activation of adenylate cyclase. Increased cAMP activates tyrosinase enzyme which converts tyrosine to dopa and dopa to dopaquinone, resulting in melanin formation. The melanin thus formed is partly secreted from the melanocytes and taken up by keratinocytes of the skin thus making the skin colour become more dark. Moreover, the pigment thus formed will constitute the colour of hair and fur in man and animal. Various colours will be produced depending on the level of the presence of melanin pigment in the hair, fur and skin.

MSH Receptor and Anti-pyretic and Anti-inflammatory Actions

The α-MSH is one of the most potent antipyretic agents identified (Clark et al. 1985). Moreover, both afferent and efferent inflammatory responses to chemicals and irritants, like phorbol esters or contact allergens, are blocked by the topical application of α-MSH. These anti-pyretic and anti-inflammatory effects seem to reside in the carboxy terminal region of the hormone supporting the notion of their mediation via an action on MSH receptors.

MSH Receptor and Vitiligo

In vitiligo areas of loss of skin pigmentation is a characteristic feature. Such loss of skin colour is due to loss and/or malfunction of pigment cells. Due to localization of MSH receptor on skin pigment cells it is considered that MSH receptor has a role in vitiligo. One of the causes of the vitiligo can be autoimmune reactions of the host against the MSH receptor protein and/or polypeptides. Thus, the MSH receptor constitute an interesting target in the cure and/or amelioration of the vitiligo condition.

DISCLOSURE OF THE INVENTION

The above summarized activity and involvement of the MSH receptor in a number of biological functions of various cells clearly shows the importance of the present invention which relates to a DNA fragment encoding a polypeptide having MSH receptor activity. Despite considerable efforts to elucidate the sequence of such a DNA fragment, nobody had prior to the present invention succeeded in doing this.

Accordingly, the present invention relates to a novel DNA fragment having the nucleotide sequence shown in SEQ ID NO: 1 or an analogue or subsequence thereof which
1) has a homology with the DNA sequence shown in SEQ ID NO: 1 of at least 50%, and/or
2) encodes a polypeptide, the amino acid sequence of which is at least 50% homologous with the amino acid sequence shown in SEQ ID NO: 2, and/or
3) encodes a polypeptide which binds an antibody which is also bound by an MSH receptor, and/or
4) encodes a polypeptide which is an MSH receptor or which has the same binding capacity as an MSH receptor.

The DNA fragment with the nucleotide sequence shown in SEQ ID NO: 1 is derived from a human cDNA library and has been found to contain an open reading frame of 951 bp which codes for a previously unknown polypeptide of 317 amino acids which is shown in SEQ ID NO: 2. This polypeptide constitutes the entire polypeptide of an MSH receptor.

A detailed description of the molecular cloning and nucleotide sequencing of the cDNA on the basis of the carefully constructed primers is given in Example 1. The cDNA of the MSH receptor represents a rather rare clone, based on the fact that its messenger RNA was found only in the melanoma cells and not in the other tissues examined like brain, thymus, parathyroid gland, parotid gland, salivary gland, adrenal gland, testis, liver, lung, heart, spleen, skeletal muscle, intestine and colon, cf. Example 1.

Transmembrane segments of the above-mentioned polypeptide (corresponding to nucleotides 286–351, 394–465, 517–588, 640–711, 733–804, 898–972 and 997–1068 in SEQ ID NO: 1, respectively) were determined by hydropathy analysis (Kyte et al. 1982).

Glycosylation sites are found at amino acid residues 15 and 29 in SEQ ID NO: 2, possible phosphorylation sites are found at amino acid residues 42–45, 151–154 and 306–308 SEQ ID NO: 2, and a possible palmitylation site is found at amino acid residue 316 in SEQ ID NO: 2.

The abbreviations of the amino acids used herein are the following:

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Each of the nucleotides shown herein is represented by the abbreviations generally used, i.e.
A represents deoxyadenine
T represents deoxythymidine
G represents deoxyguanine
C represents deoxycytosine
N represents deoxyinosine Using the DNA fragment G-8 described below (with the nucleotide sequence shown in SEQ ID NO: 7) as a hybridization probe, another novel DNA fragment has been isolated from a human genomic library. This DNA fragment is in the present application numbered as SEQ ID NO: 15. This fragment constitutes another interesting aspect of the invention as it has been shown to code for a previously unknown polypeptide which is also an MSH receptor and/or an MSH receptor subtype. The polypeptide encoded by the fragment is in the present context numbered as SEQ ID NO: 16. It is believed that the polypeptide is melanotropic hormone receptor such as an α-MSH receptor and/or a β-MSH receptor and/or a γ-MSH receptor and/or an ACTH receptor and is interchangeably referred to as MC-2 and MC-2 receptor herein. The MC-2 receptor is in particular known to be located in the central nervous system and also in peripheral organs such as gut, lung, heart, liver, spleen, smooth and skeletal muscle tissues and the immune system.

The novel DNA fragment with the nucleotide sequence SEQ ID NO: 15 comprises 1650 nucleotides and was sequenced as described herein. The nucleotides from 1 to 615 form the 5' untranslated region while the nucleotides 1591 to 1650 form the 3' untranslated region. The coding fragment from nucleotide 616–1590 encodes a polypeptide of 325 amino acids which is shown in SEQ ID NO: 16. The DNA-fragment was isolated from a human genomic library as described in Example 6.

Thus, an aspect of the invention relates to a DNA fragment having the nucleotide sequence shown in SEQ ID NO: 15 or an analogue or subsequence thereof which 1) has a homology with the DNA sequence shown in SEQ ID NO: 15 of at least 50%, and/or
2) encodes a polypeptide, the amino acid of which is at least 50% homologous with the amino acid sequence shown in SEQ ID NO: 16, and/or
3) encodes a polypeptide which binds an antibody which is also bound by an MSH receptor, and/or
4) encodes a polypeptide which is an MSH receptor or which has the same binding capacity as an MSH receptor.

While one particular aspect of the invention relates to DNA fragments having the nucleotide sequence shown in SEQ ID NO: 1 or in SEQ ID NO: 15 and encoding a polypeptide of the invention, an analogue or subsequence thereof comprising at least 15 nucleotides is another important aspect of the invention. The invention relates to the coding part of the described nucleotide sequence shown in SEQ ID NO: 1 or SEQ ID NO: 15 as well as the non-coding part. A DNA fragment which shows at least 55% homology, preferably at least 70%, more preferably at least 80% and most preferably at least 95% sequence homology with a DNA fragment of the same length obtained from the DNA sequence shown in SEQ ID NO: 1 or SEQ ID NO: 15 is also an interesting aspect of the invention as such fragments and subsequences may encode polypeptides capable of acting as epitopes and thus capable of eliciting an antibody response directed thereto. Such antibodies can also bind to a polypeptide constituting an MSH receptor and thereby being important in diagnosis and treatments of MSH receptor related diseases and conditions, as will appear from the following. In addition, such fragments and subsequences may among other utilities be used as probes in the identification of other DNA fragments as will appear from the following. In this respect a fragment and/or subsequence of the non-coding part of the DNA fragments shown in SEQ ID NO: 1 and 15 is equally important as the fragments and/or subsequences of the coding parts of these DNA fragments.

When used in the present context with regard to nucleotide sequences, the term "subsequence" indicates a nucleotide sequence which is derived from a DNA fragment of the invention and which has retained a characteristic nucleotide sequence thereof as evidenced by its conforming to at least one of the criteria 1)–4) above. Typically, the subsequence is a part of a nucleotide sequence shown in SEQ ID NO: 1 or SEQ ID NO: 15, the subsequence being either a consecutive stretch of nucleotides taken from a nucleotide sequence shown in SEQ ID NO: 1 or SEQ ID NO: 15 or being composed of one or more separate nucleotides or nucleotide sequences of a nucleotide sequence shown in SEQ ID NO: 1 and/or SEQ ID NO: 15.

It is important to note that a "characteristic nucleotide sequence" in the present context is meant to indicate a nucleotide sequence of a DNA fragment of the invention which is identifying the DNA fragment according to one or more of the following criteria:

it encodes a peptide with binding properties of an MSH receptor, and/or it encodes a peptide which is bound (with high specificity) by an antibody which also binds (with high specificity) to the polypeptide encoded by the original DNA fragment from which it is derived (the binding for instance being assessed as described in example 10), and/or it will be useful as a hybridization probe for identifying the original DNA fragment from which it is derived.

When a compound "X", such as a e.g. receptor, "binds" to a polypeptide, an antibody or another substance "Y" it is in the present application defined as a substantial specific binding of "X" to "Y" as assessed by the ability of "X" to distinguish between "Y" and other substances under physiological conditions (e.g. in a Ringer solution at 37° C. or e.g. using the binding buffer and conditions essentially as described in Example 3). It is preferred that "X" binds "Y" with known affinity. Preferably, the dissociation constant (defined as $$K = \frac{A_X \cdot A_Y}{A_{XY}},$$

wherein $A_X$, $A_Y$ and $A_{XY}$ are the activities of "X", "Y" and "XY" in the system $XY \rightleftharpoons X+Y$) of the complex "XY" is less than 10 $\mu$M, more preferably less than 1 $\mu$M, even more preferably less than 100 nM and most preferably the dissociation constant of the complex "XY" is less than 10 nM. Moreover, in a still further meaning, when "X" is said to bind to "Y", the latter which is also bound to a compound "Z" with a known high affinity (it has been established that "Y" binds to "Z" with such high affinity that it can be regarded as a test-tool), the dissociation constant of the complex "XY" formed is not more than 100,000-fold higher than that for "YZ", preferably not more than 10,000-fold, more preferably not more than 1,000-fold and most preferably not more than 100-fold higher than that for "YZ".

One way of determining such binding characteristics is to employ the method of example 3, wherein a panel of melanotropic hormones are tested with regard to their ability to inhibit binding of $^{125}$I-NDP-MSH to a suspected MSH receptor.

According to the above, a degree of homology of as little as 30% between a DNA fragment and one of the DNA fragments shown in SEQ ID NO: 1 or 15 or a subsequence thereof may in some instances ensure that a characteristic DNA sequence is retained in the first DNA fragment. Thus, the invention also relates to DNA fragments which have retained a characteristic DNA sequence of the DNA sequences in SEQ ID NO: 1 and 15, said characteristic DNA sequences having as little as 30% homology with any of the sequences shown in SEQ ID NO: 1 and 15. This will most likely be the case when the characteristic sequence is a part of a functionally important part of the polypeptide and therefore has little resemblance with other polypeptides. However, it is preferred that the degree of homology is at least 40% when the characteristic sequence codes a less functionally important part of the molecule. The degree of homology may in some instances be so high as 95%; this might be the case when the characteristic DNA fragment encodes a intramembraneous part of the polypeptide, wherein the amino acid sequence might be much like other sequences of transmembraneous polypeptides.

In the present specification and claims, the term "subsequence" thus designates a nucleotide sequence which preferably has a size of at least 15 nucleotides, more preferably at least 18 nucleotides, still more preferably at least 21 nucleotides, even more preferably at least 27 nucleotides and most preferably at least 51 nucleotides. It is well known that small fragments are useful as epitopes, DNA-probes for hybridization with DNA or RNA, in PCR techniques as is described herein, or useful in that they encode peptides comprising epitopes capable of eliciting the production of antibodies.

The term "analogue" with regard to the DNA fragments of the invention is intended to indicate a nucleotide sequence which encodes a polypeptide identical or substantially identical to a polypeptide encoded by a DNA fragment of the invention shown in SEQ ID NO: 1 or 15.

It is well known that the same amino acid may be encoded by various codons, the codon usage being related, inter alia, to the preference of the organisms in question expressing the nucleotide sequence. Thus, one or more nucleotides or codons of a DNA fragment of the invention may be exchanged by others which, when expressed, result in a polypeptide identical or substantially identical to the polypeptide encoded by the DNA fragment in question.

Thus, a DNA fragment encoding a polypeptide comprising the amino acids 1–317 of SEQ ID NO: 2, or a DNA fragment encoding a polypeptide comprising the amino acids 1–325 SEQ ID NO: 16 are very important embodiments of the invention.

Also, the term "analogue" is used in the present context to indicate a DNA fragment or a DNA sequence of a similar nucleotide composition or sequence as the DNA sequence encoding the amino acid sequence constituting an MSH receptor, allowing for minor variations which do not have an adverse effect on the ligand binding properties and/or biological function and/or immunogenicity as compared to the MSH receptor, or which give interesting and useful novel binding properties or biological functions and immunogenicities etc. of the analogue. The analogous DNA fragment or DNA sequence may be derived from an animal or a human or may be partially or completely of synthetic origin as described above. The analogue may also be derived through the use of recombinant DNA techniques.

Furthermore, the terms "analogue" and "subsequence" are intended to allow for variations in the sequence such as substitution, insertion (including introns), addition, deletion and rearrangement of one or more nucleotides, which variations do not have any substantial effect on the polypeptide encoded by a DNA fragment or a subsequence thereof. The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence-whether at either end of the sequence or at any suitable point within it, and "rearrangement" is intended to mean that two or more nucleotide residues have been exchanged with each other.

When using the term "any substantial effect on the polypeptide" is understood that the DNA fragment encodes a polypeptide which has retained its antigenicity and/or a MSH binding properties compared to the MSH receptor polypeptide encoded by the DNA fragment from which the analogue/subsequence is derived.

The terms "fragment", "sequence", "subsequence" and "analogue", as used in the present specification and claims with respect to fragments, sequences, subsequences and analogues according to the invention should of course be understood as not comprising these phenomena in their natural environment, but rather, e.g., in isolated, purified, in vitro or recombinant form.

The terms "homology" and "homologous" are, with respect to DNA fragments, intended to mean a homology between the nucleotides in question between which the homology is to be established, in the match with respect to identity and position of the nucleotides of the DNA fragments. With respect to polypeptides and fragments thereof described herein, the terms are intended to mean a homology between the amino acids in question between which the homology is to be established, in the match with respect to identity and position of the amino acids of the polypeptides.

"Binding capacity of an MSH receptor" is in this context meant as the binding properties of an MSH receptor assessed by a test wherein the binding between the receptor and various possible ligands is determined with respect to their ability of inhibiting binding of $^{125}$I-NDP-MSH ($^{125}$I-(Nle$^4$, D-Phe$^7$)-MSH) as described herein.

"Same binding capacity as an MSH receptor" is defined herein as a binding profile which shows that a substance binds $^{125}$I-NDP-MSH with a higher affinity than other compounds although the substance may be unable to elicit the effects exerted by the binding of MSH to an MSH receptor.

When reference is being made to "an analogue of MSH" or "an analogue of a melanotropic hormone" it is intended to mean a substance which shows binding capacity for an MSH receptor as defined above. Thus,.examples of analogues of MSH and analogues of melanotropic hormones are α-MSH, β-MSH, γ-MSH and NDP-MSH.

The term "melanotropic hormone" is intended to refer both to a natural peptide being derived from proopiomelanocortin (POMC), the natural peptide typically having a biological activity of that of MSH or ACTH, and a synthetic peptide, the synthetic peptide having the ability to induce at least one of the biological effects which may be induced by the natural melanotropic hormones. Examples of melanotropic hormones are α-MSH, β-MSH, γ-MSH, ACTH and NDP-MSH.

The term "melanotropic hormone receptor" is intended to mean a receptor which can be activated by a melanotropic hormone so as to induce a second messenger response (or any other typical receptor response) or a biological effect generally being referred to as a melanotropic hormone response. Stimulation of melanin formation in melanocytes and the stimulation of corticosteroid synthesis in the adrenal gland by the melanotropic hormones are typical examples of melanotropic hormone responses. Examples of melanotropic hormone receptors are the MSH receptor, the ACTH receptor and the MC-2 receptor.

The present invention is based on the construction of the primers shown as SEQ ID NO: 3 and SEQ ID NO: 4 and the analogues thereof which are defined below. As appears from the above, great interest and many efforts have been exerted in order to examine the function of the MSH receptor and thus, there has been obvious interest in isolating the DNA encoding the MSH receptor. The very careful work performed by the inventors of the present invention when designing these primers such as described in details in Example 1 rendered the present invention possible.

Thus, the DNA fragments of the invention used as primers constitute another interesting aspect of the invention and have various important utilities such as detection and isolation of other DNA fragments encoding polypeptides having similar functions and/or binding capacity as an MSH receptor. In particular, the primers can be used in the detection of other G-protein coupled or binding receptors. The invention therefore also relates to a DNA fragment having the nucleotide sequence SEQ ID NO: 3 (from segment 3) or analogues thereof, wherein the nucleotides 13 and/or 15 and/or 23 optionally are substituted by C and to a DNA fragment having the nucleotide sequence SEQ ID NO: 4 (from segment 6) or analogues thereof wherein the nucleotides 19 and/or 29 and/or 32 optionally are substituted by C, and wherein the nucleotides 20 and/or 31 are optionally substituted by G. In order to examine a DNA fragment of the invention or an analogue or subsequence thereof or an RNA fragment transcribed therefrom, such as to examine the relatedness to other foreign DNA fragments, hybridization is a useful method. Hybridization may be performed as follows: A DNA fragment or an analogue or a subsequence thereof of the invention is labelled with any of the labelling principles available (radioactive system, colour reaction system, light based system, or variations of these) so as to constitute a probe. The foreign DNA/RNA to be examined is coupled to a matrix. The matrix is subjected to a suitable treatment so as to couple the DNA/RNA to the matrix. The matrix is exposed to a prehybridization solution of a composition, at a temperature and for a period of time suited to the matrix and the foreign DNA/RNA in question. The matrix is then placed in a hybridization solution containing labelled denatured DNA probe. Hybridization is carried out at a suitable temperature and the period of time. The matrix is then washed with a solution of a composition, at a temperature and for a period of time suited to the matrix and the foreign DNA/RNA in question. The matrix is then subjected to a suitable detection system based on the nature of the label in the DNA probe. The results are then analyzed. Any hybridization of the foreign DNA/RNA and the DNA probe is an indication of similarity of the two species, and may be used to examine whether the foreign DNA/RNA is a part of the invention. In the above hybridization procedure a RNA probe corresponding to a polypeptide or an analogue or a subsequence thereof of the invention can also be used in place of a DNA probe. Another approach of determining similarity between DNA sequences is by determining the nucleotide sequence of the DNA fragment to be compared with a DNA fragment or an analogue or subsequence thereof of the invention by conventional DNA sequencing analysis, and comparing the degree of homology with the DNA fragment or an analogue or subsequence thereof of the invention.

Polymerase chain reaction (PCR) primers can be synthesized based on the nucleotide sequence of the cloned MSH receptor, or on the basis of other known similar sequences. These primers can then be used to amplify the whole or a part of an MSH receptor sequence or the sequences of its analogues. Primers as shown in SEQ ID NO: 3 and SEQ ID NO: 4 which constitute part of the invention may be used in this aspect. Polymerase chain reaction enzyme, a type of heat stable DNA polymerase, generally incorporates wrong nucleotides at a frequency of 1 in 10000 (Tindall et al. 1988) during amplification. Because of the iterative nature of the amplification this frequently attributes a new altered sequence to the amplified MSH receptor.

The DNA fragment described above and constituting an important aspect of the invention may be obtained directly from the genomic DNA or by isolating mRNA and converting it into the corresponding DNA sequence by using reverse transcriptase, thereby producing a cDNA. When obtaining the DNA fragment from genomic DNA, it is derived directly by screening for genomic sequences such as is described in Example 1. It can be accomplished by hybridization to a DNA probe designed on the basis of knowledge of an MSH receptor sequence, or the sequence information obtained by amino acid sequencing of the purified MSH receptor. When the DNA is of complementary DNA (cDNA) origin, it may be obtained by preparing a cDNA library with mRNA from cells containing MSH receptor or parts thereof. Hybridization can be accomplished by a DNA probe designed on the basis of knowledge of an MSH receptor sequence, or the sequence information obtained by amino acid sequencing of the purified MSH receptor.

The DNA fragments of the invention or analogues or subsequences thereof can also be obtained using other methods (Wright et al. 1992) like expression cloning in cell line (Xie et al. 1992) or the expression cloning in the oocyte (Julius et al. 1988; Masu et al. 1987).

A DNA fragment of the invention or an analogue or subsequence thereof can be obtained from other animals, such as mammals. The DNA obtained in this way could be exactly similar to the one shown in SEQ ID NO: 1 or SEQ ID NO: 15 or could have differences in structure attributed to well known inter-species variations.

A DNA fragment of the invention or an analogue or subsequence thereof can be replicated by fusing it with a vector and inserting the complex into a suitable microorganism or a mammalian cell line. Alternatively, the DNA fragment can be manufactured using chemical synthesis.

As mentioned above the polypeptides encoded by the DNA fragments of the invention shown in SEQ ID NO: 1 and 15 have been shown to contain coding regions encoding an MSH receptor and an MSH receptor/MSH receptor subtype, respectively.

Thus, in another particular important aspect, the invention relates to a polypeptide having the amino acid sequence shown in SEQ ID NO: 2 or an analogue or subsequence thereof which 1) is an MSH receptor or which is capable of binding to MSH or an analogue thereof, and/or 2) is encoded by a DNA fragment which is at least 50% homologous with the DNA fragment shown in SEQ ID NO: 1, and/or 3) binds an antibody which is also bound by an MSH receptor.

Another most important aspect of the invention thus relates to a polypeptide having the amino acid sequence shown in SEQ ID NO: 16 or an analogue or subsequence thereof which 1) is an MSH receptor or which is capable of binding to MSH or an analogue thereof, and/or 2) is encoded by a DNA fragment which is at least 50% homologous with the DNA fragment shown in SEQ ID NO: 1, and/or 3) binds an antibody which is also bound by an MSH receptor.

By the use of the term "MSH receptor" is meant a polypeptide being capable of binding MSH and by the term "analogue thereof" is meant any polypeptide having the same binding capacity as an MSH receptor in that the polypeptide is capable of binding MSH. Thus, included is also a polypeptide from different sources, such as different animals, such as mammals, in particular a human, which vary for example in the carbohydrate part, or the phosphorylation and/or in tissue distribution. In this context the term MSH receptor also refers to both the above-mentioned polypeptides of the invention.

The term analogue also includes polypeptides being capable of binding antibodies which also bind to an MSH receptor. Such analogues may be capable of eliciting or stimulating an immune response which is also directed against the MSH receptor or which can also be elicited by the MSH receptor. These and other analogues are encoded by a DNA fragment or analogue or subsequence thereof of the invention which with respect to analogues have been defined above. The analogues may in a particular aspect be of synthetic origin as discussed herein.

The term "analogue" with regard to a polypeptide is also used in the present context to indicate a protein or polypeptide of a similar amino acid composition or sequence as the characteristic amino acid sequence shown in SEQ ID NO: 2 or SEQ ID NO: 16 (or another polypeptide of the invention), allowing for minor variations which do not have an adverse effect on the ligand binding properties and/or biological function and/or immunogenicity, or which may give interesting and useful novel binding properties or biological functions and immunogenicities etc. of the analogue. The analogous polypeptide or protein may be derived from an animal or a human or may be partially or completely of synthetic origin. The analogue may also be derived through the use of recombinant DNA techniques.

It is being widely recognized that the same or similar gene may be present in two or several copies in the genome of the same animal. Because gene mutations will always tend to induce divergence of a DNA sequence the structure of the protein coded by the same and/or similar genes will tend to diverge during evolution. Thus, in the present context it is obvious that the MSH receptor, because of the existence of the DNA according to SEQ ID NO: 1 and SEQ ID NO: 15 in fact exist in at least two copies in the genome. Thus SEQ ID NO: 1 and 15 are both coding for proteins which have MSH receptor properties, albeit the binding properties of the two proteins for melanotropic hormones differ. It is therefore predicted that even more copies of the MSH receptor are present in the genome of an animal, for instance in homo sapiens. Because of the similarity between the amino acid composition of such proteins and the MSH receptors described herein, theses proteins are in the present application being regarded as being analogues of the MSH receptor. Thus such proteins are also part of the invention.

In the present context the term "characteristic amino acid sequence derived from an MSH receptor" is intended to mean an amino acid sequence which comprises amino acids constituting a substantially consecutive stretch (in terms of linear or spatial conformation) of the polypeptide shown in SEQ ID NO: 2 or the amino acid sequence shown in SEQ ID NO: 16 and encoding an MSH receptor. Such secondary or tertiary conformation may have interesting and useful properties and may constitute epitopes.

In the present context, the term "epitope" refers to any polypeptide of the invention or an analogue thereof capable of stimulating or interacting with immunocompetent cells and capable of stimulating the production of antibodies which also bind to a polypeptide constituting an MSH receptor. Especially epitopes showing desirable properties with regard to diagnosis and therapy constitute important aspects of the present invention.

In the present context, the term "epitope" also refers to any polypeptide of the invention or a characteristic amino acid sequence or an analogue thereof capable of interacting or binding existing or novel substances which are also bound by a polypeptide constituting an MSH receptor. The said substances can be organic molecules, small peptides or large polypeptides or derivatives of any of the above. Such an approach can find use in the drug screening programme.

The term "receptor subtype" is intended to mean a receptor which is capable of binding the same ligand and/or ligands as another receptor, albeit the affinities of the ligands for the receptors may be different for the compared receptors.

Thus, when referring to MC-2 as an "MSH receptor subtype" it is indicated that MC-2 is an MSH receptor, but that the pattern of binding to various ligands/substances is different from that of another MSH receptor, such as e.g. the MSH receptor with the amino acid sequence shown in SEQ ID NO: 2.

The term "subsequence" with regard to a polypeptide designates a polypeptide sequence which comprises a part of the polypeptide sequence shown in SEQ ID NO: 2 or SEQ ID NO: 16 or other polypeptide sequences of the invention which may optionally have retained its capability of binding MSH. Included are also polypeptide subsequences which have been analogized by modifications as explained herein. Polypeptides constituting interesting epitopes or encoded by a nucleotide subsequence of the invention as defined above are also included.

"A derivative of an MSH receptor" is meant to indicate both an analogue, subsequence or subtype of an MSH receptor.

In a most important aspect, the invention relates to a polypeptide encoded by the DNA fragment shown in SEQ ID NO: 1, preferably the polypeptide shown in SEQ ID NO: 2, and to a polypeptide encoded by the DNA fragment with the nucleotide sequence shown in SEQ ID NO: 15, preferably the polypeptide shown in SEQ ID NO: 16.

The polypeptides of the invention also comprises polypeptides which show a degree of homology of at least 55%, preferably at least 70%, more preferably at least 80% and most preferably at least 95% homology to a polypeptide of the same length which has an amino acid sequence which is a part of the sequences shown in SEQ ID NO: 2 and SEQ ID NO: 16.

The invention also relates to a characteristic amino acid sequence being a subsequence comprising from at least 5 amino acids to 316 acids of SEQ ID NO: 2 and to a subsequence comprising from 5 to 324 amino acids of SEQ ID NO: 16, and any analogue to such polypeptides. Preferably the subsequence comprises at least 7 amino acids, more preferably at least 10 amino acids, even more preferably at least 15 amino acids and most preferably at least 30 amino acids. The polypeptide may be coupled to any other moiety.

The present invention also relates to a substantially pure polypeptide which has the same binding capacity as an MSH receptor or which is recognized by an antibody raised against or reactive with a polypeptide of the invention. Furthermore the invention relates to any polypeptide of the invention in substantially pure form.

Furthermore, the invention relates to a polypeptide as defined herein which is glycosylated or which is linked to a carbohydrate or lipid moiety. Also a polypeptide containing a palmitoyl anchor or a part thereof constitutes an interesting aspect as well as any polypeptide of the invention in lipid soluble form which may, in one interesting aspect of the invention as described herein, be used in the treatment of an animal, in particular a human, having impaired function of the receptor.

The lipid soluble form of polypeptide of the invention may be a form comprising components such as liposomes, micelles and phospholipid so as to allow the polypeptide to be incorporated in the cell membrane of the recipient. It is important that the lipid soluble form is a form which ensures the stability of the polypeptide and preferably in a form which is pharmaceutically acceptable so as to allow the administration of the lipid soluble form to an animal, in particular a human. The lipid soluble form may also be in a form comprising components such a detergent, oil, such as mineral oil or vegetable oil or water, and which may be a suspension of one or more of the above mentioned components.

In the present context, the term "substantially pure" is understood to mean that the polypeptide in question is substantially free from other components, e.g. other polypeptides or carbohydrates, which may result from the production and/or recovery of the polypeptide or otherwise be found together with the polypeptide. The high purity of a polypeptide of the invention is advantageous when the polypeptide is to be used for, e.g., the production of antibodies. Also due to its high purity, the substantially pure polypeptide may be used in a lower amount than a polypeptide of a conventional lower purity for most purposes. The purification of a polypeptide of the invention may be performed by methods known to a person skilled in the art.

The polypeptides of the invention having the amino acid sequences shown in SEQ ID NO: 2 and 16 and which are MSH receptors bear similarity with other G-protein coupled receptors. They have the most common feature of passing through the cell membrane 7 times, like all other G-protein coupled receptors. Based on the observations of homology between the transmembrane segments of different G-protein coupled receptors, it has been hypothesized that the extracellular loops and the transmembrane segments are involved in the ligand binding, such as e.g. the binding of MSH or an analogue of MSH or of a synthetic organic molecule serving as ligand for the receptor. The intracellular loops have been assigned the role of coupling-to the G-proteins and possible involvement in other intracellular activities. In the present context the above mentioned extra and intracellular loops as well the transmembrane segments that are intended to be involved in the binding of the ligand and/or the coupling of G-proteins are one or two or several or all of the mentioned segments and loops of the receptor.

Intense efforts to solve the 3-dimensional (3D) structure of G-protein coupled receptors and some related proteins (e.g. bacteriorhodopsin and opsins) are ongoing in several laboratories world wide. It is expected that once the 3D structure of one of these proteins is solved, the 3D structure of other G-protein coupled receptors will become easily solvable using computational methods, provided that their primary amino acid structure is known. This is due to the fact that all G-protein coupled receptors are likely to show similar gross 3D structure (Sankara-Ramakrishnan & Vishveshwara 1989; Findlay & Eliopoulos 1990; Hibert M. F. et al. 1991).

Thus, in certain embodiments of the invention are considered especially important amino acids 1–39, 100–116, 182–188 and 269–276 which are considered to constitute the extracellular loops of the MSH receptor. These regions will be of particular importance as epitope targets for antibodies intended for clinical use in e.g. targeted drug delivery. or for drug design.

In other embodiments of the invention are considered especially important the amino acids 63–75, 142–157, 213–243 and 301–317 which are considered to constitute the intracellular loops of the MSH receptor. These regions will be particularly important in the elucidation of the mechanisms for the coupling of the MSH receptor to G-proteins. These regions may serve as targets for drugs aiming for the modulation of the interaction of the receptor with G-proteins. It may also in particular be desired to alter the amino acid sequences, by e.g. deletions, site directed mutations, insertions of extra amino acids, or combinations thereof, to generate novel MSH receptor analogues showing altered properties. Such altered receptors may be desired to further the understanding of the molecular mechanisms in the coupling of the receptor with G-proteins. Moreover, yet another aspect pertaining to this particular part of the invention is the DNA sequences coding for the intracellular segments, in particular base pairs 636–726, but also the other segments, as these regions are considered to be less homologous with other G-protein coupled receptor coding fragments. Thus, such regions of the sequence may serve to generate DNA probes which in hybridization studies, as is described in detail below, are selective for the MSH receptor DNA or mRNA.

In yet other embodiments of the invention are considered particularly important the amino acids 40–62, 76–99, 117–140, 158–181, 189–212, 244–268 and 277–300 which are considered to constitute the transmembrane segments of the MSH receptor. It may here be desired to alter one or several specific amino acids to generate MSH receptor analogues showing altered properties. Such altered receptors may be desired to further the understanding of the molecular mechanisms in the binding of MSH and MSH analogues to the receptor. Moreover, yet another aspect pertaining to this particular part of the invention is the DNA sequences coding for the transmembrane segments as these regions are considered to be highly homologous with other G-protein coupled receptor coding fragments which are natural variants of the MSH receptor. Such receptor coding fragments may exist in other species which code for species variants of the MSH receptor. Such receptor coding fragments may also exist in humans as well as animals which encode homologous receptors which are subtypes of the MSH receptor or which are closely related receptor types possibly belonging to the same class of melanotropic hormone receptor family. By using homology screening methods utilizing DNA sequences derived from the transmembrane segments it may be possible to obtain the DNA sequences of these homologous receptor coding fragments.

Because of the difference in sequence of SEQ ID NO: 16 from SEQ ID NO: 2 the following fragments of the MC-2 receptor are considered especially important: Amino acids 1–37, 98–114, 180–186 and 266–273 of SEQ ID NO: 16 which are considered to constitute the extracellular loops of the MC-2 receptor. These regions will be of particular importance as targets for antibodies intended for clinical use in e.g. targeted drug delivery or for drug design.

In other embodiments of the invention are considered especially important the amino acids 62–73, 139–155, 212–239 and 298–325 of SEQ ID NO: 16 which are considered to constitute the intracellular loops of the MC-2 receptor. These regions will be particularly important in the elucidation of the mechanisms for the coupling of the MC-2 receptor to G-proteins. These regions may serve as targets for drugs aiming for the modulation of the interaction of the receptor with G-proteins. It may also in particular be desired to alter the amino acid sequences, by e.g. deletions, site directed mutations, insertions of extra amino acids, or combinations thereof, to generate novel MC-2 receptor analogues showing altered properties. Such altered receptors may be desired to further the understanding of the molecular mechanisms in the coupling of the receptor with G-proteins. Moreover, yet another aspect pertaining to this particular part of the invention is the DNA sequences coding for the intracellular segments, in particular base pairs 633–717 of SEQ ID NO: 15, but also the other segments, as these regions are considered to be less homologous with other G-protein coupled receptor coding fragments. Thus, such regions of the sequence may serve to generate DNA probes which in hybridization studies, as is described in detail below, are selective for the MC-2 receptor DNA or mRNA.

In yet other embodiments of the invention are considered particularly important the amino acids 38–61, 74–97, 115–138, 156–179,187–211, 240–265 and 274–297 of SEQ ID NO: 16 which are considered to constitute the transmembrane segments of the MC-2 receptor. It may here be desired to alter one or several specific amino acids to generate MC-2 receptor analogues showing altered properties. Such altered receptors may be desired to further the understanding of the molecular mechanisms in the binding of MSH and MSH analogues to the receptor. Moreover, yet another aspect pertaining to this particular part of the invention is the DNA sequences coding for the transmembrane segments as these regions are considered to be highly homologous with other G-protein coupled receptor coding fragments which are natural variants of the MC-2 receptor. Such receptor coding fragments may exist in other species which code for species variants of the MC-2 receptor. Such receptor coding fragments may also exist in humans as well as animals which encode homologous receptors which are subtypes of the MC-2 receptor or which are closely related receptor types possibly belonging to the same class of melanotropic hormone receptor family. By using homology screening methods utilizing DNA-sequences derived from the transmembrane segments it may be possible to obtain the DNA sequences of these homologous receptor coding fragments.

The above mentioned specific amino acid sequences are prominent examples of subsequences according to the invention. It is to be understood that the other important subsequences according to the invention are subsequences which are modifications of the above mentioned subsequences in that, and with respect to particular subsequences of which they are modifications, they fulfil any one of the criteria 1)–3) for the polypeptide as stated above. Also included in this aspect of the invention is a DNA fragment encoding any such amino acid sequence.

Using the primers of the invention, three DNA fragments have been isolated and sequenced. These DNA fragments termed G-6 shown in SEQ ID NO: 5, G-8, shown in SEQ ID NO: 7 and G-10, shown in SEQ ID NO: 9, share homologies with the DNA sequence shown in SEQ ID NO: 1.

Thus, the present invention also relates to a DNA fragment or a subsequence or an analogue thereof which shows a homology with any of the nucleotide sequences shown in SEQ ID NO: 5, SEQ ID NO: 7 or SEQ ID NO: 9 of at least 40%, or which can be isolated by using the nucleotide sequence shown in SEQ ID NO: 13 and/or SEQ ID NO: 14 as a primer, or which has any of the nucleotide sequences shown in SEQ ID NO: 5, SEQ ID NO: 7 or SEQ ID NO: 9. The homology may in some aspects be at least 50%, preferably at least 55%,.more preferably at least 70%, even more preferably at least 80% and most preferably at least 95% with any of the DNA sequences shown in SEQ ID NO: 5, SEQ ID NO: 7 or SEQ ID NO: 9, respectively.

Polypeptide sequences or subsequences or analogues thereof which show a homology of at least 40% with any of the polypeptides shown in SEQ ID NO: 6, 8 or 10 encoded for by the DNA sequences shown in SEQ ID NO: 5, SEQ ID NO: 7 and SEQ ID NO: 9, respectively, constitute yet another embodiment of the invention. The homology may in some aspects be at least 50%, preferably at least 55%, more preferably at least 70%, even more preferably at least 80% and most preferably at least 95% with any of the polypeptides shown in SEQ ID NO: 6, SEQ ID NO: 8 and SEQ ID NO: 10, respectively.

Any of the DNA fragments of the invention may in a particular embodiment of the invention be used for the preparation of a DNA probe which may be labelled or unlabelled and which is used to isolate full length coding fragments and/or to detect or quantitate RNA. The information-of any of these DNA fragments may also be used to make PCR primers and for making a polypeptide.

As mentioned above and described in the examples, the G-8 fragment has been used to isolate a new MSH receptor subtype, MC-2. It is therefore contemplated to perform similar experiments using the two other fragments G-6 and G-10.

The DNA fragments G-6 and G-10 represent two potential G-protein coupled receptors, and can be used to isolate full length coding fragments for them using for example the same methodology as described in Example 1.

In particular, because of substantial homology of G-6 and G-10 with the primers shown in SEQ ID NO: 3 and SEQ ID NO: 4 of the invention, it is considered that one or both of G-6 and G-10 represent coding fragments encoding receptors for peptides sharing similar origin as the MSH receptor; that is the POMC (proopiomelanocortin) receptors, such as e.g. the ACTH receptor, the met-enkephalin receptor and the β-endorphin receptor. In particular, it is considered that one or both of G-6 and G-10 are the $\mu$, $\delta$ and $\sigma$ opioid receptors because of their dissimilarities to the $\kappa$ opioid receptor.

However, G-6 and G-10 each has unique sequence characteristics starting in the intracellular segment 5, that is the amino acids "L-Y-V/I-H-M", and it may be contemplated that one or both of G-6 and G-10 represent parts of DNA sequences encoding receptors for a novel class of peptide hormone receptors; e.g. the corticotropin releasing hormone receptor, the growth hormone releasing hormone receptor, the gonadotropin releasing hormone receptor, the thyrotropin releasing hormone receptor, the luteinizing hormone releasing hormone receptor, the follicle stimulating hormone releasing hormone receptor, the chorionic gonadotropin hormone receptor and/or the glucagon receptor.

However, G-6 and G-10 also has short extracellular loops, indicating that the receptors encoded by these fragments constitute the small peptide hormone type of G-protein coupled receptors. Thus, one or both of G-6 and G-10 may represent the neuropeptide Y receptor, the tumour necrosis factor receptor, the colony stimulating factor receptor, the interleukin 1 receptor, the neurotensin receptor, the atrial natriuretic factor receptor, the kallidin receptor, the bulbogastrin receptor, the motilin receptor, the pancreatic polypeptide receptor, the olfactory receptor subtype, the spermatozoon feromone receptor subtype, the insulin like growth factor receptor, the taste receptor subtype, the gustuducin coupled receptor subtype, the inhibin receptor subtype and/or the kyotropin receptor.

The dissimilarity of the G-6 and G-10 with other known nucleotide fragments coding for G-protein coupled receptors, the latter of which include a substantial amount of well characterized receptors for amines, may indicate that one or both of G-6 and G-10 by contrast encode genes for lipids, e.g. more specifically receptors for prostanoids, that is, more specifically the prostaglandin $E_1$ receptor, the prostaglandin $E_2$ receptor, the prostaglandin $F_{2\alpha}$ or receptors for prostacyclins, e.g. the $PGI_2$ receptor, and/or receptors for leukotrienes, e.g. the leukotriene $D_4$ receptor and/or the leukotriene $C_4$ receptor and/or a receptor for a non-lipid, e.g. the phosphatidic acid receptor and/or the thromboxane A2 receptor and/or the platelet activating factor receptor.

Due to general characteristics of G-6 and G-10 being G-protein coupled receptors, it is considered that one or both of G-6 and G-10 by contrast encode genes for subtype of the substance P receptor, substance K receptor, endothelin receptor, angiotensin receptor, chemoattractant peptide receptor, bombesin receptor, oxytocin receptor, vasopressin receptor, antidiuretic hormone receptor, gastrin receptor, cholecystokinin receptor, canabinoid receptor, follicle stimulating hormone receptor, luteinizing hormone receptor, growth hormone receptor, thyrotropin receptor, calcitonin receptor, calcitonin gene related peptide receptor and/or parathyroid hormone receptor.

Based on the knowledge of the DNA fragments of the invent on (or the knowledge of the analogues or RNA fragments) the described DNA fragments of the invention can be produced containing one or more modified nucleotides to improve resistance against nucleases or to improve transport across cell membranes.

Suitable polypeptides can be produced using recombinant DNA technology. More specifically, the polypeptides may be produced by a method which comprises cultivating or breeding an organism carrying a DNA fragment or an analogue or a subsequence thereof of the invention under conditions leading to expression of said DNA fragment, and subsequently recovering the expressed polypeptide from the said organism.

The organism which can be used for the production of such a polypeptide may be a higher organism e.g. an animal, or a lower organism e.g. a microorganism. Irrespective of the type of organism used, a DNA fragment of the invention or an analogue or a subsequence thereof (described above) should be introduced in the organism either directly or with the help of a suitable vector. Alternatively, the polypeptides may be produced in the mammalian cell lines by introducing a DNA fragment of the invention either directly or with the help of an expression vector.

The DNA fragments or analogues or subsequences thereof of the invention can also be cloned in a suitable stable expression vector and then put into a suitable cell line. The cells expressing the desired polypeptides are then selected using the conditions suitable for the vector and the cell line used. The selected cells are then grown further and form a very important and continuous source of the desired polypeptides.

A polypeptide of the invention can also be made by in vitro translation of the RNA complementary to a DNA fragment of the invention. This can be achieved for the whole molecule, or a part or parts of the molecule, in free form or in fusion with one or several proteins. The methods which can be used are described (Sambrook et al. 1989; Spirin et al. 1988). The polypeptides of the invention can also be expressed in vitro as functional proteins in the fused or the unfused form (Zozulya et al. 1990).

In line with the above, the invention relates to a vector containing a recombinant DNA insert coding for an MSH receptor polypeptide of the invention or a fusion polypeptide as defined herein. In one particular important embodiment, a DNA fragment or an analogue or subsequence thereof of the invention or a fusion DNA fragment of the invention as defined herein m ay be carried by a replicable expression vector which is capable of replicating in a host organism or a cell line.

The vector may in particular be a plasmid, phage, cosmid, mini-chromosome or virus. In an interesting embodiment of the invention, the vector may be a vector which, when introduced in a host cell, is integrated in the host cell genome.

Included a s an important aspect of the invention is also an organism which carries and is capable of expressing a DNA fragment of the invention. Such a plasmid vector has been constructed and i s designated pE-11D herein. This vector constitutes yet another aspect of the invention.

Also, the invention relates to an organism which carries and is capable of replicating a DNA fragment of the invention and also such a plasmid vector designated pB-11D has been constructed and constitutes a part of the invention. This vector was deposited on Aug. 24, 1992 under the number DSM 7214 in the Deutsche Sammlung von Mikroorganismen under the terms and conditions of the Budapest Treaty.

Further, yet another plasmid vector, designated pB-MC-2, has been constructed, which is capable of replicating a DNA of the present invention. pB-MC-2 thus constitutes yet a very important aspect of the invention. The construction of pB-MC-2 is described in detail in Example 6.

Moreover, still yet another plasmid vector, designated pE-MC-2, which is also a very important embodiment of the invention, has been constructed. The pE-MC-2 plasmid vector is capable of expressing the MC-2 receptor of the present invention. The construction of pE-MC-2 is detailed in Example 7 and the use of pE-MC-2 for the expression of the MC-2 receptor is exemplified in Example S. This vector has been deposited on Aug. 9, 1993 under the number DSM 8440 in the Deutsche Sammlung von Mikroorganismen under the terms and conditions of the Budapest Treaty.

Organisms which may be used in this aspect of the invention of producing the peptides of the invention comprise a cell which is a microorganism such as a bacterium, a yeast, a protozoan, or which is derived from a multicellular organism such as a fungus, an insect, a plant, a mammal or it may be a cell line. If the organism is a bacterium, it is preferred that the bacterium is of the genus Bacillus, e.g. *B. subtilis,* Escherichia, e.g. *E. coli,* or Salmonella.

If a higher organism is used, transgenic techniques may be employed for the production of the polypeptides. Examples of suitable animals are sheep, cattle, pigs etc. A DNA fragment encoding a polypeptide of the invention is expressed together with a polypeptide which i s inherently expressed by the animal, e.g. a milk protein or the like. The resulting fusion protein may then be subjected to post-translational modifications so as to obtain a polypeptide of the invention.

In another aspect of the invention a MSH receptor may be obtained from a suitable cell type found to naturally express MSH receptor from DNA encoding an MSH receptor. Such cells may be e.g. a melanoma cell line, as is shown in Example 3 for WM 266-4 cells, or they may be obtained from any tissue containing cells expressing a DNA fragment of the invention.

A stable cell line capable of producing a polypeptide of the invention having MSH binding properties, has been established. The cell lines of COS-7 cells constitute other important aspects of the invention. The cell line harbours the DNA fragment with the nucleotide sequence SEQ ID NO: 1 and steadily produces polypeptides having binding properties substantially identical to the binding properties described below. The production of this stable cell line is described in detail in example 5.

Thus, the invention also relates to a stable cell line producing a polypeptide of the invention which optionally binds NDP-MSH with high affinity; the establishment of such a cell line may be performed according to the technique described in Example 5, or to any other method known to the person skilled in the art.

In one particular aspect of the invention, a DNA fragment of the invention may comprise one or more second nucleotide sequence(s) encoding one or more polypeptide(s)

different from or identical to a polypeptide of the invention fused in frame to a DNA fragment of the invention or an analogue thereof encoding a polypeptide or an analogue or subsequence thereof of the invention with the purpose of producing a fused polypeptide which polypeptide constitutes yet another interesting aspect of the invention. When using recombinant DNA technology the fused DNA sequences may be inserted into a suitable vector or genome. Alternatively, one of the nucleotide sequences is inserted into the vector or genome already containing the other nucleotide sequence(s). A fusion polypeptide can also be made by inserting the nucleotide sequences separately and allowing the expression to occur. The host organism, which may be of eukaryotic or prokaryotic origin is grown under conditions ensuring expression of fused sequences. The fused polypeptide is then purified and a polypeptide of the invention separated from its fusion partner using a suitable method. The fusion polypeptide may in a particular embodiment of the invention still be capable of binding to MSH or an analogue thereof.

The second polypeptide to which a polypeptide of the invention is fused may in one particular embodiment of the invention be a DNA fragment encoding a diphtheria toxin, a staphylococcus protein, a ricin toxin, Pseudomonas endotoxin, abrin or fungal ribosome-inactivation proteins (RIP). In other embodiments of the invention the second DNA fragment may encode a subsequence of a melanotropic hormone receptor, an MSH receptor or an ACTH receptor.

The fusion polypeptides of the invention may be modified as well as other polypeptides of the invention, e.g. they may be glycosylated, coupled to a carbohydrate or lipid moiety, contain a palmitoyl anchor or a part thereof bound to a solid support and be provided with a detectable label.

The present invention also relates to a polypeptide of the invention in substantially pure form and to a method of producing the polypeptide. The method of producing a polypeptide of the invention comprises the following steps:

(a) inserting a DNA fragment of the invention in an expression vector, (b) transforming a suitable host organism with the vector produced in step (a), (c) cultivating the host organism produced in step (b) under suitable conditions for expressing the polypeptide, (d) harvesting the polypeptide, and (e) optionally subjecting the polypeptide to posttranslational modifications.

A DNA fragment or an analogue or subsequence thereof of the invention encoding a polypeptide of invention can be modified before or after it has been inserted into the vector or organism for expression. The polypeptide product may also be subjected to modification. The modification may comprise substitution, addition, insertion, deletion or rearrangement of one or more nucleotides and amino acids in the DNA and polypeptide, respectively. The term "substitution" is intended to mean the replacement of one or more nucleotides or amino acids in a DNA fragment or polypeptide of the invention. The term "addition" means addition of one or more nucleotides and amino acids at either end of a DNA fragment/polypeptide of the invention or a part of them. Insertion is intended to mean the introduction of one or more nucleotides and amino acids in a DNA fragment or polypeptide of the invention or a part of them. Deletion is intended to mean the removal of one or more nucleotides and amino acids from a DNA fragment or polypeptide of the invention or from a part of them. Rearrangement is intended to indicate that one or more nucleotides or amino acids have been exchanged within the DNA or polypeptide sequence, respectively. The DNA fragment may, however, also be modified by mutagenesis either before or after inserting it in the organism. A DNA or protein sequence of the invention may be modified in such a way that it does not lose any of its biophysical, biochemical or biological properties, or part of such properties (one and/or all) or all of such properties (one and/or all).

The polypeptide produced as described above may be subjected to posttranslational modifications such as thermal treatment, chemical treatment (formaldehyde, glutaraldehyde etc.) or enzyme treatment (peptidases, proteinases and protein modification enzymes). The polypeptide may be processed in a different way when produced in an organism as compared to its natural production environment. It may or may not be advantageous to remove or alter the processing characteristics caused by the host organism in question.

When a polypeptide according to the invention is produced in a prokaryotic organism such as a bacterium, a useful posttranslational modification may be refolding of the peptide in order to obtain the peptide in a native and functional form due to the fact that peptides produced this way are often found as insoluble non-functional inclusion bodies inside the microorganism. The refolding of such peptides of such inclusion bodies are traditionally refolded by denaturing the peptide followed by a gradual continuous renaturation.

The term "truncated" polypeptide refers to a polypeptide deleted of one or more amino acids eventually resulting in changing of the properties of the polypeptide, such as e.g. solubility. In a further meaning, the term "truncated" polypeptide refers to a mixture of polypeptides all derived from one polypeptide or expressed from the coding fragment (s) encoding said polypeptide.

Subsequent to the expression according to the invention of the polypeptide in an organism or a cell line, the polypeptide can either be used as such or it can first be purified from the organism or cell line. If the polypeptide is expressed as a secreted product, it can be purified directly. If the polypeptide is expressed as an associated product, it may require the partial or complete disruption of the host before purification. Examples of the procedures employed for the purification of polypeptides are: (i) immunoprecipitation or affinity chromatography with antibodies, (ii) affinity chromatography with a suitable ligand, (iii) other chromatography procedures such as gel filtration, ion exchange or high performance liquid chromatography or derivatives of any of the above, (iv) electrophoretic procedures like polyacrylamide gel electrophoresis, denaturating polyacrylamide gel electrophoresis, agarose gel electrophoresis and isoelectric focusing, (v) any other specific solubilization and/or purification techniques.

Also, preparation of polypeptides of the invention may be performed by the well known methods of liquid or solid phase peptide synthesis utilizing the successive coupling of the individual amino acids of the polypeptide sequence. Alternatively, the polypeptide can be synthesized by the coupling of individual amino acids forming fragments of the polypeptide sequence which are later coupled so as to result in the desired polypeptide. These methods thus constitute another interesting aspect of the invention.

Very important and thus constituting important aspects of the invention are various methods of regulating the activity exerted by an MSH receptor. This activity which has been described above in details may have important implications for the various disease conditions connected to the MSH receptor and for the various other biological functions. Thus, methods for preventing or stimulating the binding of the MSH receptor to various molecules constitute important aspects of the invention.

One of such aspects of the invention relates to a method of preventing or stimulating the coupling of the described MSH receptor to its guanine nucleotide binding protein comprising using a method wherein a ligand is bound to an epitope of the receptor which normally interacts with the G-protein, in particular one or several of the extracellular loops and/or the transmembrane sequence and/or the cytoplasmic loops and/or the C-terminal sequence, thereby inhibiting or stimulating the coupling between the G-protein and the receptor. Thus, in one aspect this method comprises administering a substance to an animal, in particular a human, which substance in advance has been found to bind to a polypeptide having the amino acid sequence shown in SEQ ID NO: 2 or 16 or a subsequence comprising any of the subsequences encoding one or several of the extracellular loops and/or the transmembrane sequence and/or the cytoplasmic loops and/or the C-terminal sequence or a combination thereof.

In this context a "ligand" will refer to a substance, which may be natural or synthetic, and which will bind in a preferably reversible, but also possibly irreversible manner to the MSH receptor.

Another method according to the invention of preventing or stimulating the binding of MSH or similar peptides or a G-protein to the described MSH receptor comprises administering a substance to an animal, in particular a human, which substance in advance has been found to bind to a polypeptide having the amino acid sequence shown in SEQ ID NO: 2 or 16 or an analogue or subsequence thereof comprising any of the subsequences encoding one or several of the extracellular loops and/or the transmembrane sequence and/or the cytoplasmic loops and/or the C-terminal sequence or a combination thereof, so as to occupy the binding site of the receptor using an agonist, an antagonist, a blocker or a substance such as a derivative of MSH having a structure similar to MSH, and optionally thereby preventing or stimulating the generation of second messenger elements. The substance may be a synthetic ligand such as a peptide, an organic compound or an antibody capable of binding to the receptor or a part thereof. The antibody may be a monoclonal or polyclonal antibody.

A method of reducing or increasing the binding affinity of the MSH receptor is an interesting aspect of the invention and may be obtained by the use of allosteric modulation. Further a way of preventing the coupling of the MSH receptor to its guanine nucleotide binding protein according to the invention is to reduce the production of the MSH receptor. This may be obtained by using antisense oligotherapy wherein a DNA or RNA fragment complementary to at least part of the mRNA corresponding to a polypeptide of the invention or an analogue thereof may be effective in arresting the translation of the polypeptide in human cells and thereby inhibiting the synthesis of MSH receptor polypeptide.

A method for increasing the production of the MSH receptor may be receptor upregulation. Also a method of decreasing or increasing the generation of second messenger elements and/or increasing the production of the MSH receptor and/or optionally increasing or decreasing the binding affinity of MSH to the MSH receptor is part of the invention. The method comprises administering to an animal, in particular a human, a medicament which is or becomes bound to a substance, which substance in advance has been found to bind to a polypeptide having the amino acid sequence shown in SEQ ID NO: 2 or 16 or an analogue or subsequence comprising any of the subsequences encoding one or several of the extracellular loops and/or the transmembrane sequence and/or the cytoplasmic loops and/or the C-terminal sequence or a combination thereof.

A substance as the above indicated could be chosen by employing the methods described below for identifying substances which can prevent or stimulate the effect exerted by MSH receptors.

A method for internalization of an MSH receptor, thereby making it unavailable for the binding of the hormone, constitutes another aspect of the invention. The method comprises using a substance which in advance has been found to bind to a polypeptide having the amino acid sequence shown in SEQ ID NO: 2 or 16 or a subsequence comprising any of the subsequences encoding one or several of the extracellular loops and/or the transmembrane sequence and/or the cytoplasmic loops and/or the C-terminal sequence or a combination thereof, such as a substance or a modified form of the MSH which is either able or unable to initiate the normal processes activated by the hormone but which substance causes internalization of the receptor. This method may also be used to regulate the effect exerted by the MSH receptor.

By using radioligand binding techniques and expressed MSH receptor protein and peptides the binding affinities of substances (ligands) for the MSH receptors may be measured. Such measurements are typically performed in the screening of novel drugs (synthetic or natural) with potential activity on MSH receptors. In pharmacological terms such drugs may act as agonists, partial agonists or as antagonists at the MSH receptor. All types of such substances are testable using the method according to the invention. The substances/ligands acting on the MSH receptor (or its derivative) can also be coupled to toxic agents (toxins, radionuclides) aiming to destroy the MSH receptor (or the MSH receptor derivative) bearing organisms or cells.

A very important aspect of the invention relates to methods for identifying substances which may be used for preventing or stimulating the effect exerted by an MSH receptor such as the generation of a second messenger element in a cell, such as a mammalian cell, in particular a human cell. Inhibiting the binding of MSH to the MSH receptor is one way of achieving this, and therefore methods for identifying substances which are capable of binding to the MSH receptors are very important aspects of the invention. The methods involve various methods of assessing the capability of the substance in question to compete with the binding of MSH to the MSH receptor. The substance may prevent this binding by blocking the MSH binding site on the MSH receptor resulting in blocking of the effects exerted by the MSH receptor upon binding of MSH. In another embodiment, the substance may be a substance with optionally increased binding capacity to the MSH receptor (compared to MSH) and which is in addition capable of activating the effects exerted by the MSH receptor.

One embodiment of this aspect of the invention is to incubate an MSH receptor protein or its analogue, obtained as described in Example 3, with radioactively labelled MSH or MSH analogue together with the test substance. Depending on the binding activity of the test substance the amount of labelled MSH or MSH analogue becoming bound to the MSH receptor will vary. Test substances with high binding affinity for the MSH receptor will exclude the binding of the labelled MSH or MSH analogue at lower concentration than test substances with lower binding affinity. Separation of bound versus free labelled MSH or MSH analogue is accomplished using techniques such as filtration, centrifugation, superflow or chromatography. Measurement of radioactivity either retained on the receptor or being present in the solution separated from the receptors is made using standard nuclear counting. In another variant of this embodiment of the invention, the amount of MSH or MSH analogue being bound to the receptor or being present in the solution separated from the receptors is detected by using any other suitable detection system capable of detecting MSH or MSH analogue. Examples of such detection systems are immune assays such as radio immune assay and ELISA (Enzyme linked immune sorbent assay), immune fluorescence assay, UV light absorption spectrometry or fluorescence emission spectrometry.

In another embodiment of this aspect of the invention, the amount of test substance bound to the MSH receptor is indirectly and/or approximately estimated by measuring the alteration in the degree of interaction of the MSH receptor with a G-protein caused by the binding of test substance to the MSH receptor. In a variant of such a test system, the effect of the test substance is studied alone. In another variant of such an assay, the ability of the test substance to compete for MSH or MSH analogue is studied by the simultaneous addition of test substance and MSH or MSH analogue. The degree of activation of the G-protein by the MSH receptor caused by the test substance, the MSH or the MSH analogue can be measured directly by e.g. measuring the GTPase activity of the system using previously described methods (Aktories and Jakobs 1981; Vachon et al. 1986), or by using other suitable methods. Alternatively the degree of activation of the system may be studied indirectly by measuring other biochemical or physiological parameters which may become altered as a consequence of the primary interaction of the ligand(s) with the MSH receptor. Examples of measurable entities in this context are adenylate cyclase activity, cAMP-levels, skin pigmentation, tyrosinase activity and [$^{35}$S]methionine incorporation (Burchill et al. 1990).

In yet another embodiment of the invention, which is particularly useful if the ligand is a macromolecule, such as when the ligand is an antibody, the detection of the binding of the ligand to the receptor may be done using other approaches. In one variant of this embodiment, the ligand is incubated with a substantially pure preparation of the MSH receptor or its analogue, the latter which has been tagged with a suitable molecule which, after separation of bound versus free MSH receptor, will allow the detection of the MSH receptor ligand complex by e.g. nuclear counting, colour, fluorescence or enzymatic activity. Separation of bound and free ligand may, for example, be accomplished by adding a second antibody which is directed towards the ligand thereby forming a precipitate of the ligand-receptor complex. In other variants of the invention, a substantially pure preparation of the MSH receptor is attached to a solid support. The ligand is then incubated with the solidified receptor whereafter detection of the amount of ligand bound to the receptor may be done using conventional ELISA or using any similar suitable approach.

It will be understood that the ligands described herein may be provided with a detectable label. The ligands themselves can be macromolecules, such as monoclonal or polyclonal antibodies or they may be substances of natural or synthetic origin which are able to bind to MSH receptor.

Using the above and similar approaches substances can be identified which can block the binding of the MSH receptor (or its derivative) by the receptor ligands. In the present context the term "blocking of the MSH receptor (or its derivative)" means that the MSH receptor (or its derivative) is occupied by the substance so that the receptor ligands cannot bind the MSH receptor (or its derivative) or that the MSH receptor ligands are capable of binding to the MSH receptor but unable to activate the MSH receptor.

It will be understood that methods similar to those mentioned above for identifying substances which bind to an MSH receptor can be used for identifying substances which bind to other melanotropic hormone receptors. Since the DNA fragments of the invention which have the nucleotide sequences shown in SEQ ID NO: 5 and 9, coding for the polypeptides of the invention shown in SEQ ID NO: 6 and 10 may be derived from other melanotropic hormone receptors, the binding properties of these melanotropic hormone receptors may be of great importance. Thus, important aspects of the invention are methods as the above-mentioned for identifying substances which are capable of binding to melanotropic hormone receptors.

It is of course also important to note, that the DNA fragments having the nucleotide sequence shown in SEQ. ID NO: 5, 7 and 9 can be modified in the same manner as other DNA fragments of the invention, and thus, all disclosure in the present specification relating to the modifications of the DNA fragments having the nucleotide sequence shown in SEQ. ID NO: 1 and 15 applies analogously or mutatis mutandis to modifications of the DNA fragments having the nucleotide sequence shown in SEQ ID NO: 5, 7 and 9. Also, as aspects of the invention, the DNA fragments having the nucleotide sequences shown in SEQ ID NO: 5, 7 and 9 can be used in the same manners as described in the present specification for the DNA fragments having the nucleotide sequences shown in SEQ ID NO: 1 and 15. Likewise, the polypeptides having the amino acid sequences SEQ ID NO: 6, 8 and 10 can be modified in the same manner as the polypeptides shown in SEQ ID NO: 1 and 15, and thus, all disclosure in the present specification relating to the modification of the polypeptides having the sequences shown in SEQ ID NO: 6, 8 and 10 applies analogously or mutatis mutandis to modifications of the polypeptides shown in SEQ ID NO: 1 and 15. Also, as aspects of the invention, the polypeptides having the amino acid sequences shown in SEQ ID NO: 6, 8 and 10 can be used in the same manners as described in the present specification for the polypeptide having the amino acid sequence shown in SEQ ID NO: 1 and 15.

The polypeptide with the amino acid sequence SEQ ID NO: 2 has been identified as an MSH receptor, based on the results of such binding experiments. A series of POMC (pro-opiomelanocortin) derived peptides showed differential potencies in inhibiting $^{125}$I-NDP-MSH binding to MSH receptor coding fragment transfected COS-7 cells. The potency order was NDP-MSH ($K_i$=23±0.5 pM)>α-MSH ($K_i$=92±19 pM)>ACTH (1–39) ($K_i$=170±37 pM)>β-MSH ($K_i$=449±74 pM)>γ-MSH ($K_i$=1010±200 pM). ACTH (4–10) showed very low binding affinity ($K_i$=22,400±7200 pM), whereas the non-melanotropic POMC peptide β-endorphin showed no affinity for the expressed MSH receptor.

Moreover, in addition the polypeptide with the amino acid sequence shown in SEQ ID NO: 16, referred to as the MC-2 receptor, has been identified as an MSH receptor and/or MSH receptor subtype based on the result of such binding experiments. A series of POMC derived peptides showed the following differential potencies in inhibiting 125I-NDP-MSH binding to MC-2 receptor coding fragment transfected COS-7 cells: NDP-MSH (Ki=5.18±0.54 nM)>α-MSH (Ki=

928±314 nM)=ACTH (1–39) (Ki=929±389 nM)>β-MSH (Ki=1.75±0.67 μM)>γ-MSH (Ki=3.45±0.88 μM). The non-melanotropic POMC peptide β-endorphin showed no affinity for the expressed MC-2 receptor.

The above mentioned binding experiments can be done using whole animal systems, human clinical trials, a tissue specimen, a microorganism and/or a cell, in particular a cell line expressing the said receptor protein or its analogue. It can also be achieved using the purified protein of the invention. The purified protein can be used in a soluble form or in the solid phase being attached to a suitable matrix.

Drugs can be designed so as to act on very specific parts of a polypeptide of the invention. Drugs can be acting on either only the regions of or within the extracellular loops or transmembrane segments. In either case it may be affecting the binding of the natural ligands to the MSH receptor or its derivatives. Specific drugs can also be directed towards the regions of intracellular loops. Such drugs could be affecting the coupling of the MSH receptor or its derivatives to the intracellular systems like the G-proteins. Such drugs could also be affecting the G-proteins so that they cannot couple to the MSH receptor or its derivatives.

Various ways of treating the disease conditions wherein an MSH receptor is involved are provided by the present invention. These diseases include MSH receptor expressing disease condition such as melanoma, skin cancer, pyretic condition, inflammatory condition, nociceptive condition, catatonic condition, impaired memory condition, reduced or increased skin tanning and/or pigmentation conditions, epilepsy. The invention also includes a method to improve nerve repair, muscle reinnervation and/or neuron growth.

Due to its central nervous system localization the MC-2 receptor is in particular a target for drugs used in treating conditions such as pain, pyretic, catatonic and impaired memory conditions. Moreover, due to peripheral localization of the MC-2 receptor it is an interesting target for the anti-inflammatory drugs. The MC-2 receptor is also an interesting target for drugs improving growth and/or regeneration and/or repair of neurons being damaged due to disease and/or toxic influence and/or age and/or by other condition being associated with or leading to neuron damage. Moreover, due its ability to improve muscular reinnervation the MC-2 receptor is an interesting target for drugs treating condition of impaired muscle innervation. In addition due to its central nervous system localization the MC-2 receptor is also an important target for drugs used in the treatment of epilepsy.

Thus, the invention relates to a method of targeting a cell that contains an MSH receptor on the surface with a medicament comprising administering the medicament in the form of a substance that binds to the MSH receptor. In a particular embodiment of the invention, the medicament may be attached to a substance such as an antibody or a part thereof or be a molecule of natural or synthetic origin having affinity for the MSH receptor. The medicament may be a radionuclide or a toxin or any other molecule of natural or synthetic origin. The use of an antibody such as a monoclonal antibody as a substance to which a medicament is bound comprises an important aspect of the invention. The antibody could be tagged with toxin or radioactivity for diagnostic or therapeutic purposes. Such an approach is expected to be superior to the MSH toxin conjugates mentioned above, because of the expected high avidity and specificity of such MSH receptor antibodies. Moreover, the MSH toxin conjugates might induce untoward effects by virtue of their potential hormonal activity. The use of toxin or radiation coupled monoclonal antibodies against the MSH receptor may prove to be a very attractive approach as the MSH receptor is the most common and most specific component of the melanoma cells.

In another embodiment of the invention the substance is a natural or synthetic organic compound, or a peptide or derivative thereof, that binds to the receptor or an epitope thereof and which optionally may become discovered by using methodology described in the present application. Such a substance may in particular be a synthetic and/or a natural compound which have or do not have any structural resemblance to MSH. Such substances are typically composed of one or two or several aromatic and/or non-aromatic rings and/or heterocyclic rings, with side chains appropriately attached and may in addition have chains interconnecting the ring structures. Such substances vary considerably in their structure and there exist several different classes of such substances which is due to the fact that they either bind to the same or the differing epitopes of the MSH receptor. Some of these substances share partly or totally the same binding epitope on the MSH receptor as the MSH peptide, whereas other substances bind to other and/or partially other epitopes of the MSH receptor. Some of these substances have the ability to mimic the action of MSH in that when they bind to the receptor they cause the same effects in a cell and/or organ and/or tissue as when MSH binds to the MSH receptor. Other substances by contrast have the ability to prevent the action of MSH on the receptor by their binding to the MSH receptor.

In a very important aspect of the invention, a lipid soluble form of an MSH receptor may be used in the treatment of an animal, in particular a human, by administering this form to the animal.

Also in a very important aspect of the invention, conditions caused by MSH receptor deficiency or impaired MSH receptor function in an animal, in particular a human may be treated by introducing a DNA fragment encoding an active form of an MSH receptor. One such condition which may be treated by the present invention is tyrosinase-positive albinism.

As stated previously, endogenous and exogenous melanotropins are suggested to enhance human cutaneous pigmentation in vivo (Levine 1991; Mulligan et al. 1982; Lerener et al. 1961). A treatment which produces tanning without sun exposure will be helpful to people who tan poorly and sunburn easily. Increased melanin in the skin might afford these people protection against ultraviolet light and thus put them at low risk for skin cancer.

The use of MSH and other melanotropins may be an effective and safe means of achieving skin darkening without harmful excess sun exposure. In addition, the resultant increased skin pigmentation might provide protection against the effects of subsequent sun exposure. In patients with tyrosinase-positive albinism, the molecular machinery to make melanin is present, but functions suboptimally (King et al. 1988). Perhaps, by acting on MSH receptor melanotropins could in these patients stimulate tyrosinase resulting in an increase in pigmentation. This may afford these individuals protection from ultraviolet light while improving their appearance and social acceptance.

In the present context melanotropin is intended to be a substance that is binding to an epitope of an MSH receptor and thereby e.g. induces a similar skin tanning effect as MSH or any other desirable effect similar to that of MSH. Such a substance may be found using the methodology described in the present application and may in particular be a synthetic substance which have or do not have any structural resemblance to MSH.

Also, the invention relates to a method for increasing the melanin content of the skin in an animal, in particular a human, comprising using substances that are active through an MSH receptor. Thus, the skin tanning may be obtained without or with reduced exposure to sunlight which will make it possible to avoid sunburns, which is most desirable as already explained above.

Detection of the MSH receptors of the invention is important in various diagnostic aspects of the invention and may facilitate the diagnosis of various of the disease conditions associated with a content of MSH receptors in the tissue that is higher than normally found in said tissue and improve the prognosis of some of the diseases such as melanoma and skin cancer. Especially important aspects of the invention are the use of the detection of MSH receptor in MSH receptor expressing diseases, such as melanoma or skin cancer, in assessing the prognosis and/or guidance for further treatment.

Thus, the invention relates to a method of diagnosing an MSH receptor expressing disease condition such as melanoma or skin cancer comprising targeting a cell containing an MSH receptor on the surface with a diagnostic agent capable of binding to the MSH receptor, which diagnostic agent can be detected following binding to the receptor. The diagnostic agent may be administered bound to a substance that binds to MSH receptor.

The diagnostic agent may be a radioactive substance, or may be linked to a radioactive substance. In other embodiments, the diagnostic agent may be a coloured or colour generating substance or linked to a colour or colour generating agent.

One diagnostic method of the invention is detecting an MSH receptor in a biological sample, wherein the sample is treated with a substance that binds to the MSH receptor, and detecting or visualizing the presence of the bound substance. In a particular interesting embodiment of the invention, the substance is an antibody or a part thereof. The antibody may be an antibody that distinguishes between possible different forms of the MSH receptor. The antibody may be labelled with radionuclide, or biotinylated or may be unlabelled and later detected by immunostaining. An important method in connection with this part of the invention is detection and/or measurement of the bound antibody by a method of the ELISA type or by a method of the radioimmunoassay type.

The terms "a sample" or "a biological sample" as used herein are defined as a cell, a subcellular fraction, a cell fraction, a tissue sample, a cell culture, or a cell suspension.

In connection with the above, the invention also relates to polyclonal and monoclonal antibodies which are reactive with a polypeptide or an analogue or subsequence thereof of the invention. A detailed description of the various aspect of the invention involving antibodies and which constitutes parts of the invention is given herein.

In the present context the term antibody is understood as the whole antibody molecule or any fragments thereof. An antibody can be fragmented during and/or after the production. It can also be made in the fragmented form to begin with and used as such or used after joining different fragments.

The animal used for the preparation of antibodies to a polypeptide of the invention is preferably selected from the group consisting of rabbit, monkey, sheep, goat, mouse, rat, pig, horse and guinea pigs. The cells producing the antibodies may be spleen cells or peripheral blood lymphocytes.

The antibody or fragments thereof may be of a monospecific (polyclonal) kind. The monospecific antibody may be prepared by injecting a suitable animal with a substantially pure preparation of a polypeptide of the invention. This can be followed by one or more booster injections at suitable intervals before the first bleeding. The animals are bled about 5–7 days after each immunization. Antibodies may optionally be isolated from the serum using standard antibody purification techniques (Sambrook et al. 1989).

Using the sequence of SEQ ID NO: 2 polyclonal antibodies have been prepared by chemically synthesizing two peptides which had the amino acid sequences identical to amino acids 4–19 and 25–35 of SEQ ID NO: 2, respectively.

These two peptides were (separately) coupled to thyroglobulin and separately injected into rabbits in Freund's adjuvant. After four booster injection both the conjugates were found to have induced formation of sera in the rabbits which were highly reactive against MSH receptor containing cells. The details of the manufacturing of the anti MSH rabbit sera is given in Example 10.

A monoclonal antibody or fragments thereof may be raised against an essential component of an MSH receptor, i.e. an epitope. The monoclonal antibody may be produced using conventional techniques (Köhler et al. 1975) by use of a hybridoma cell line, or by clones or subclones thereof or by cells carrying genetic information from the hybridoma cell line producing said monoclonal antibody. The monoclonal antibody may be produced by fusing cells producing said monoclonal antibody with cells of a suitable cell line, and cloning the resulting hybridoma cells producing said monoclonal antibody. Alternatively, the monoclonal antibody may be produced by immortalizing an unfused cell line producing said monoclonal antibody. The monoclonal antibodies are ultimately harvested from the cell growth medium. Hybridoma cells used to make monoclonal antibody may be grown in vitro or in the body cavity of an animal. The monoclonal antibody or fragments thereof may also be made using the recombinant DNA techniques (Huse et al. 1989).

Monoclonal antibodies may also be made by immunizing the suitable animals with a unpurified preparation of an MSH receptor protein. The resulting hybridoma clones secreting monoclonal antibodies can be screened for their ability to block the binding of MSH or its analogue to the MSH receptor e.g. using the approach described in example 3.

The idiotypic (antigen binding) structure of the antibody is antigenic and can thus give rise to specific antibodies directed against the idiotypic structure. The antibodies raised against the idiotype are called the anti-idiotypic antibodies. Such antibodies may mimic the structure of the original antigen and therefore may function as the original antigen. Such antibodies may be able to substitute the original antigen (MSH receptor protein, polypeptides or their analogues) for a part or all of the functions, usability and properties of the original polypeptide of the invention.

Preferably the monoclonal antibodies or fragments thereof will be used in most cases but polyclonal antibodies or fragments thereof may also be used. Typical uses of MSH receptor antibodies are as follows:

For Purification of Proteins

The antibodies can be used to purify an MSH receptor or its derivatives from the biological samples, using the affinity chromatography or the immunoprecipitation techniques.

For Diagnosis and Therapy

The monoclonal antibodies against an MSH receptor or its derivatives can be used in the diagnosis and therapy of disease conditions in animals and humans. The diagnostic and therapeutic antibodies may be valuable for the disorders of skin, like skin cancer generally described as melanoma.

The finding that MSH receptor is consistently found on melanoma tissues supports this notion. The diagnostic agent may be an antibody with the specificity for a polypeptide of the invention. The antibody can be coupled to another protein or a solid support and/or can be used in the agglutination tests or the colour developing tests. Such antibodies can also be used to quantitate the MSH receptor or its derivatives in biological samples using the standard histochemistry or immunochemistry techniques.

For Toxin Therapy

The specific monoclonal antibodies can be coupled to different toxins like ricin or diphtheria toxin. Generally the A-chain of the plant toxin ricin or the A-chain of the diphtheria toxin is conjugated to the monoclonal antibody in order to assemble hybrid proteins which have a targeted cytotoxicity. Moreover, the toxin used may alternatively be selected from Pseudomonas endotoxin, abrin or fungal ribosome-inactivation proteins (RIP). In the present context, a hybrid between the monoclonal antibody against a polypeptide of the invention and a toxin moiety can be used to bring about the killing of the MSH receptor bearing cells in an organism. Moreover, in the present context the toxin is intended to mean any toxin that is suitable for the purpose of killing and/or damaging the cell wherein the MSH receptor is located. The toxic effect of the toxin may be brought about when the toxin is still conjugated with the antibody. However, more likely the toxin will be processed once the antibody-toxin conjugate has become attached to the MSH receptor bearing cell. Such processing may involve e.g. internalisation of the antibody-toxin complex, cleavage of toxin from antibody and transportation of the toxin within the cell to its site of action. The processing is being done by the natural machinery of the MSH receptor bearing cell and careful engineering of the properties of the antibody-toxin complex will maximise its toxicity by affording the most favourable processing pathway for the complex.

In order to improve the clinical efficiency of the antibody-toxin complex the monoclonal antibody can be designed so as to reduce its size by e.g. utilising F(ab')$_2$ or Fab' fragments instead of the whole intact antibody. The reduction in the size of the molecule will increase the ability of the antibody-toxin complex to diffuse from the blood to the site of the tumour cell. Moreover, selecting a small sized toxin for the conjugation to the antibody, such as e.g. fungal RIP, will afford the same effect. Moreover, elimination of the Fc fragment, as is achieved with the use of F(ab')2 or Fab' fragments for toxin conjugation, will eliminate the possibility that the antibody-toxin conjugate will bind to cells containing Fc receptors thus minimising non-specific binding of the toxin complex to other cells than MSH receptor bearing cells. Thus, this measure will increase the selectivity of the antibody-toxin complex and increase its cytotoxic effect since a higher dose will be possible to administer. The problem of inducing a humoral immune response in the patent to whom the antibody-toxin conjugate is administered may be minimised by prior and/or concomitant administration of a drug which suppress the immune response. Such drugs may e.g. be selected from cyclophosphamide, prednisone, azathioprine and/or cyclosporin. Moreover, another approach for the same purpose is to administer a monoclonal antibody directed towards CD4 antigen. Yet, another approach for the same purpose is to carefully engineer the antibody-toxin complex to minimise its immunogenicity. Such engineering is afforded by eliminating the most immunogenic epitopes of the complex while still retaining its ability to bind to the MSH receptor with high affinity and retaining its desired toxic effect. Moreover, the engineering will also have the purpose to increase the stability of the complex after it has been administered to the patient. Increased stability is essential to afford a good therapeutic effect.

Increased clinical efficiency of the antibody-toxin complex may also be afforded by concomitant administration to the patient of another agent which will potentiate the toxicity of the complex. The other agent may e.g. be cyclophosphamide, daunorubicin and/or interferon. Moreover, increased toxicity may be afforded by simultaneously utilising antibody-toxin complexes where two and/or several toxins with different mechanism for their toxicity has been included. As an alternative the simultaneous administration of another antibody-toxin complex which is directed for yet another melanoma protein, with the anti MSH receptor antibody-toxin complex of the present invention, will afford increased clinical efficiency. Yet another measure to afford increased clinical efficiency of the antibody-toxin complex will be afforded by the additional coupling to the MSH receptor antibody-toxin complex a suitable radionuclide which by virtue of RIT induces a cytotoxic effect. The approach of RIT for therapy of melanoma is described further below.

For Radiodiagnosis and Radiotherapy

The monoclonal antibodies against an MSH receptor or its derivatives can be used in the diagnosis and therapy of disease conditions in animals and humans. The diagnostic and therapeutic antibodies may be valuable for the disorders like skin cancer generally described as melanoma. The finding that MSH receptor is consistently found on melanoma tissues supports this notion.

The specific monoclonal antibodies can also be coupled to different radionuclides like, $^{123}$I, $^{125}$I, $^{131}$I, $^{99m}$Tc, $^{111}$In, $^{186}$Re, $^{188}$Re, $^{211}$At, $^{212}$Bi, $^{90}$Y, $^{67}$Cu and $^{67}$Ga. Such radiolabelled antibodies can be used for diagnosis (Radioimmunoscintigraphy) or therapy (Radioimmunotherapy).

In the present context a radionuclide is intended to mean any radionuclide that is suitable for the purpose of detecting the cell and/or cell cluster that is hosting an MSH receptor. Coupling of radionuclides to anti MSH receptor antibodies may be afforded by a number of techniques. For $^{123}$I, $^{125}$I and/or $^{131}$I coupling is afforded by well established chloramine-T, iodogen, lactoperoxidase and/or hydroxyperoxidase methods. Moreover, radioiodination may as an alternative be afforded using Bolton-Hunter reagent. Radiolabelling with e.g. $^{111}$In and/or $^{90}$Y and/or $^{67}$Cu may be afforded by the coupling of a bifunctional chelating agent to the antibody and then adding the radionuclide to the complex. By virtue of the chelating ability of the complex the radionuclide will become attached to the complex. Suitable chelators may be selected from eg. isothiocyanatobenzyl EDTA (CITC), diethylenetriaminepenta-acetic acid (DTPA) and be coupled via the mixed anhydride or the cyclic anhydride (Hnatowich 1990). However, since such complexes may provide somewhat unstable chelation and moreover during their manufacture intra and intermolecular cross linking of antibodies, other chelators such as e.g. GYK-DTPA or SCN-Bz-DTPA may be used as an alternative (Hnatowich 1990). Radiolabelling of $^{99m}$Tc to the antibody may be afforded by using direct labelling techniques such as by reducing disulphide bonds on the antibody thereby providing sites for stable attachment of $^{99m}$Tc. One method for this end is to use tin which will afford reduction of disulphide bonds and adding [$^{99m}$Tc]pertechnetate which also will provide $^{99m}$Tc by reduction with the tin (Hnatowich 1990). In the present context tin may be provided in the form of e.g. stannous tartrate or any other form suitable for the purpose. As an alternative to tin another suitable reducing agent may be used such as e.g. dithiotreitol and/or 2-mercaptoethanol. Moreover, [$^{99m}$Tc]-glucartate and/or [$^{99m}$Tc]-phosphonate may substitute for [$^{99m}$Tc] pertechnetate as source for $^{99m}$Tc. Yet another approach for $^{99m}$Tc labelling of anti MSH antibodies is to use chelators as was described above. For the purpose of $^{99m}$Tc chelation a promising concept is to couple metallothioneins to the anti MSH receptor antibody since the proteins afford strong chelation of $^{99m}$Tc. Still another chelator that may be employed is the diamide demercaptide chelator (Fritzberg et al. 1986).

Radioimmunoscintigraphy procedure is based on the fact that the labelled antibody will recognize the MSH receptor (or its derivative) on the cells, normal or diseased, and that the antibody will not bind to the cells devoid of the MSH receptor (or its derivative). The ultimate quality of the scintigraphic examination is dependent on the absolute quantity of the MSH receptor (or its derivative) in the specimen under examination and the background activity. It is possible to detect tumours using this technique when the tumour to non-tumour signal ratios are 1.5/1 or higher. Imaging is initially generally performed as planar scintigraphic examination. Anatomical landmarks are indicated with a point source, separately recorded, and afterwards added with computer assistance. A Single Photon Emission Computed Tomography (SPECT) can be performed, acquiring data by a 360 degree rotation of the gamma camera around the object under examination. Transverse, coronal, sagittal or oblique sections are then reconstructed using mathematical calculations. SPECT appears to improve sensitivity and requires low tumour/non-tumour signal ratio. In the present context the above mentioned approach can be used in the diagnosis of skin cancers and other disease conditions where MSH receptor (or its derivative) is expressed and can be approached by the monoclonal antibody against a polypeptide of the invention.

Radioimmunotherapy (RIT) for killing diseased cells by a toxic agent bound to a specific monoclonal antibody is a promising concept. In order to be efficient RIT has requirements besides the tumour/non-tumour signal ratio. The amount of radioactivity has to be sufficient to eradicate tumour without giving a high radiation dose to the surrounding normal tissue. Furthermore, distribution of the labelled monoclonal antibody in the tumour has to be homogeneous, allowing radiation of all tumour cells. The biological half life of the monoclonal antibody in the tumour has to be long enough to allow the radionuclide to exert maximal radiation effects. In the present context, the above mentioned approach can be used in the therapy of skin cancers and other disease conditions where MSH receptor (or its derivative) is expressed and can be approached by the monoclonal antibody against a polypeptide of the invention.

As Ligand Binding Blockers

The prevention of the binding of an MSH receptor (or its derivative) by the receptor ligands can be suitably performed by the antibodies with the specificity for a polypeptide of the invention. In the present context the term "blocking of an MSH receptor (or its derivative)" means that the MSH receptor (or its derivative) is occupied by the antibodies so that the receptor ligands cannot activate the MSH receptor (or its derivative).

In accordance with the above, the invention also relates to an antibody capable of binding to a polypeptide of the invention provided with a detectable label, and to a polypeptide of the invention provided with a detectable label. The polypeptide or the antibody may in some embodiments be coupled to a solid support. The support may be selected from the group consisting of plates, strips, beads, particles, films and paper, and the solid support may be of latex, polystyrene, polyvinyl chloride, polyolefin, nylon, polyvinylidene difluoride, cellulose, silicone or silica.

Other methods for detection and/or quantitation of an MSH receptor comprise detection of the DNA or RNA and such methods are preferably based on the principles of hybridization which have been described in details above. Thus, in one such aspect the invention relates to a method for detection and/or quantitation of the mRNA of an MSH receptor comprising extracting RNA from a biological sample such as a subcellular fraction, a cell, a tissue sample, a cell culture or a cell suspension and measuring the hybridization of said RNA to a labelled DNA fragment of the invention or a labelled RNA fragment which can be constructed from a DNA fragment of the invention. Also, methods for measuring RNA such as northern blot or dot blot may be employed. The hybridization may be performed in situ or a labelled antisense mRNA probe may be used. In another embodiment detection and/or quantitation of the MSH receptor mRNA may be obtained by extracting RNA from cells or tissues and converting it into cDNA for subsequent use in the polymerase chain reaction (PCR). The PCR primer(s) may be synthesized based on a DNA fragment of the invention such as the DNA fragments shown in SEQ ID NO: 1, SEQ ID NO: 3 or SEQ ID NO: 4 or any other DNA fragment of the invention. This method for detection and/or quantification may be used as a diagnostic method for diagnosing an MSH receptor expressing disease condition such as melanoma, skin cancer, pyretic condition, inflammatory condition, nociceptive condition, catatonic condition, impaired memory condition, reduced or increased skin tanning condition and/or pigmentation condition.

In another specific embodiment of the invention this method for the detection of MSH receptor RNA and/or DNA is used as production control in the breeding of animals for obtaining a desired fur and/or skin colour in the animal. Animals for which such a control of fur and/or skin colour is desired may be selected from e.g. mammals and reptiles and may in particular e.g. be a snake, alligator, crocodile, mink, fox, hamster or chinchilla.

In yet a further embodiment of the invention the MSH receptor coding fragment(s) or a subsequence thereof is being analyzed in an animal by using e.g. cloning or PCR as described above. The thus obtained DNA and/or cDNA is subjected to sequence analysis using known methodology with the purpose of detecting a specific variant of an MSH receptor. The detection of such variants of MSH receptor may be desired e.g. in production control for the breeding of animals in order to obtain a desired skin and/or fur colour. Animals for which such a control of fur and/or skin colour is desired may be selected from e.g. mammals and reptiles and may in particular e.g. be a snake, alligator, crocodile, mink, fox, hamster or chinchilla.

In still a further embodiment of the invention a desired skin and/or fur colour of the animal is being obtained by introducing into the animal the desired variant of the MSH receptor by e.g. manufacturing a transgenic animal which will appropriately produce the MSH receptor variant. As an alternative the desired MSH receptor variant is being obtained by mutating a natural MSH receptor coding fragment in situ in the animal. Animals where the introduction of MSH receptor variants are desired may be selected from e.g. mammals and reptiles and may in particular e.g. be a snake, alligator, crocodile, mink, fox, hamster or chinchilla.

In the present context an MSH receptor variant is intended to mean a homologue and/or analogue of SEQ ID NO: 1, SEQ ID NO: 2, SEQ ID NO: 15 or SEQ. ID NO: 16.

The lack of detailed structural information at the atomic level about the tertiary structure of the MSH receptor (a member of the G-protein coupled receptor family) continues to hamper efforts to understand receptor function at the molecular level. A polypeptide of the invention can be produced in large quantities using protein purification methods, and/or recombinant DNA techniques and/or synthetic chemistry approach. The polypeptide of the invention can then be crystallized. Crystallization, the ordered packing of molecules in three dimensions, relies on achieving the right balance of attractive and dispersive or repulsive forces between protein molecules in solution. To solubilize an integral membrane protein, like an MSH receptor or its derivatives, it is necessary to replace the natural phospholipid environment by the detergent. The resultant shell of detergent around the protein is considered to be the most important factor impeding the formation of ordered crystals. Removal of the detergent leads to the precipitation of the protein and renders it useless for the crystallographic studies.

The main problem in crystallisation of an MSH receptor is to find the ideal detergents which forms stable or semi-stable complexes with the membrane section of the MSH receptor, where there are 7 transmembrane sections. It is also a prerequisite that the overall structure of the receptor is not affected too much, something which can be validated using functional assays such as e.g. radioligand binding as has been described in the present application. Several classes of detergents, which are useful for crystallisation, are presently known and may be applied. It is a good approach for each of these detergents to obtain individual phase diagram for the solubility of the MSH receptor and analyze these diagrams in detail in order to find optimal conditions for crystallisation. Using such approach it will be possible to find and refine a buffered solution or a mixture of detergents and salts to force the protein unit to arrange intermolecular contacts for crystal growth. By salts are in the present context intended mono and/or divalent ions which may support the interaction of individual MSH receptor molecules to arrange in a crystal lattice. Moreover, crystallisation may be afforded by alternatively or in addition adding MSH or an MSH analogue which will bind to the receptor and increase the possible surface(s) for intramolecular contact. In addition the solubility of the MSH receptor may be analyzed using temperature gradients. The initial aggregation of nucleus, indicating crystallisation, can be analyzed in combination with e.g. laser light scattering. To obtain crystals the approaches such as e.g. sitting and hanging drop as well as micro-batch applications may be utilised. Improved crystals may be obtained using microgravity conditions. As a final approach heavy atom cluster can also be applied.

Crystal aggregates may be analyzed by subjecting them to e.g. synchrotron radiation at a suitable wave length, such as e.g. an 1 Å wave length or a wave length more or less than 1 Å, and collecting data for radiation diffraction. The application of anomalous scattering to solve the phase problem in crystallography can be applied. Moreover, cooling of crystals a suitable temperatures such as e.g. −10° C. and 4° C. or the flash freezing of MSH receptor crystals, which are very radiation sensitive, may be applied. The solution of 3D structure of the MSH receptor from X-ray diffraction pattern may be afforded using well known computational techniques.

Although no G-protein coupled receptor (family to which the MSH receptor belongs) has yet formed crystals, two other integral membrane proteins, the photosynthetic reaction centre (Allen et al. 1987) and bacteriorhodopsin (Henderson et al. 1990), have been successfully studied. Similar techniques as singly or in combination can be applied to the crystallization and/or atomic structure determination of the polypeptides of the invention. Moreover, other techniques aiming at the elucidation of the 3D structure of proteins are being rapidly developed. One such technique, which is already far advanced, is two-dimensional NMR (Wright 1989), as well as modern multidimensional NMR-techniques. In order to utilize such a technique for elucidation of MSH receptor 3D structure it is required to have sufficient amounts of pure MSH protein and then obtain the appropriate two-dimensional or multidimensional NMR data which is used along with the known primary amino acid sequence of the receptor applying appropriate computational methods. In addition computational methods are also being developed aiming to elucidate the 3D structure of proteins in the computer. These methods are generally and collectively referred to as molecular modelling. It is predicted that once the 3D structure of one member of the G-protein coupled receptor family is solved, it will be possible to rapidly solve the 3D structure of the other members provided that their primary amino acid sequences are known, by using one, two or several of above mentioned methods. This is due to the predicted high similarities in the 3D structure of these receptors. Successful elucidation of the 3D structure of other classes of proteins, such as the elucidation of the 3D structure of renin based on its homology to trypsin (Radung 1988), has already been successfully achieved, and an analogous approach may be used to obtain the 3D structure of an MSH receptor. In such an approach the backbone of the MSH receptor protein is aligned with the backbone of another G-protein coupled receptor using the most homologous parts of the amino acid sequences (subsequences) of the two proteins. In general only the transmembrane segments of the receptors are considered in this alignment. After that the MSH receptor has been aligned with the backbone of the other G-protein coupled receptors refinement of the structure of the MSH receptor is being made by careful positioning of the transmembrane segments of the MSH receptor, e.g. involving the rotation and tilting of transmembrane segments, as well as the positioning of amino acid side chains, until eventual Wan der Waals overlaps has been eliminated. Moreover, further refinement of the structure is being made by finding positions of the amino acid side chains which will form suitable bonds, such as e.g. hydrogen bonds, in between different amino acids of the same and/or the adjacent transmembrane segments. Finally further refinement of the structure is being made by minimizing the energy of the system using well known computational techniques. The energy of the system is usually calculated by approximate methods e.g. by using the Amber force field but also the more exact methods of quantum mechanical calculations may be applied. Such computations are readily being made using commercially available computer programmes such as e.g. Hyperchem, Sybyl etc.

It is understood that once the atomic structure of one of the G-protein coupled receptors is known, it will be relatively easy to do the same for other members, including an MSH receptor, of this very important receptor family.

Knowledge of the atomic structure on the one hand will help to understand the receptors function in minute details and on the other hand will facilitate the improvement of the specific drug developments through computational and/or other suitable methods. Among the methods that can be applied are 3D graphical analysis of epitopes, the docking of ligands to potential epitopes of the MSH receptor and de novo design of substances in the computer.

Thus, the present invention also relates to the use of a polypeptide sequence of the invention for the deduction of three dimensional structure of an MSH receptor or an analogue thereof having MSH binding capacity for use in the design of a substance capable of binding to the MSH receptor.

It will be understood that the above disclosed DNA fragments can be used for finding and isolating other similar DNA fragments, i.e. DNA fragments of the invention, by employing techniques like PCR and hybridization. Also, it is possible to use the polypeptides of the invention for designing DNA probes to be used for such finding and isolation. Thus, using this approach oligonucleotide primers are deduced from the polypeptide sequences of the present invention using the universal genetic code. Such primers can be used to perform PCR to find and isolate other similar DNA fragments as described in Examples 1 and 4. Thus, such uses of DNA fragment and polypeptides of the invention also constitute important aspects of the invention.

BRIEF DESCRIPTION OF THE DRAWINGS

FIG. 1. Agarose gel electrophoresis analysis. Lane 1—molecular weight markers. Lane 2—PCR reaction as described in Example 1. Three DNA products can be seen at 705 bp, 501 bp and 372 bp. The band at 372 bp position was later used to clone the full length coding fragment for human MSH receptor.

FIG. 2. Northern blot analysis of the tissue distribution of the GE4 mRNA. Ten μg of poly(A)$^+$ RNA from different tissues, namely brain (lane 2), thymus (lane 3), parathyroid gland (lane 4), Parotid gland (lane 5), salivary gland (lane 6), adrenal gland (lane 7), testis (lane 8), liver (lane 9), lung (lane 10), heart (lane 11), spleen (lane 12), skeletal muscle (lane 13), intestine (lane 14), colon (lane 15) and WM 266-4 human melanoma cells (lane 16), was separated by electrophoresis and blotted onto a membrane. It was then hybridized to $^{32}$P-labelled GE4 probe. As can be seen a positive band was seen only in lane 16 corresponding to the WM 266-4 human melanoma cells. The GE4 DNA was later found to be a part of the MSH receptor coding fragment. See Example 1 for details.

FIG. 3. Plasmid map of pB-11D.

FIG. 4. Plasmid map of pE-11D.

FIG. 5. $^{125}$I-NDP-MSH binding to the WM266-4 human melanoma cells.

FIG. 6. Relative potencies of melanotropins for inhibiting $^{125}$I-NDP-MSH binding to COS-7 cells (available from ATCC) transfected with MSH receptor cDNA. Competition curves are shown for non-labelled NDP-MSH (■), α-MSH (●), ACTH (1–39) (□), β-MSH (▲), γ-MSH (▼), ACTH (4–10) (○) and β-endorphin (Δ). Experimental procedures are as described in Examples 2 and 3. Each point represents the mean of quadruplicate determinations. Non-specific binding was less than 8 percent of the total binding.

FIG. 7. Plasmid map of pB-MC-2.

FIG. 8. Plasmid map of pE-MC-2.

FIG. 9. Relative potencies of melanotropins for inhibiting 125I-NDP-MSH binding to COS-7 cells (available from ATCC) transfected with pE-MC-2 plasmid DNA. Competition curves are shown for non-labelled NDP-MSH (■), α-MSH (●), ACTH (1–39) (□), β-MSH (▲), γ-MSH (▼), and β-endorphin (○). Experimental procedures are as described in Examples 7 and 8. Each point represents the mean of quadruplicate determinations. Non-specific binding was less than 8 percent of the total binding.

FIG. 10. Agarose gel electrophoresis analysis of the PCR products generated from the human brain and melanoma cells mRNA. Lane 1—molecular weight markers, Lane 2—human brain mRNA without reverse transcription, Lane 3—human brain mRNA after reverse transcription, Lane 4—human melanoma cells mRNA without reverse transcription, Lane 5—human melanoma cells mRNA after reverse transcription. A specific product at the expected position of 380 bp is seen only in the human brain sample after reverse transcription.

EXAMPLES

Example 1

Molecular Cloning and Nucleotide Sequencing of the MSH Receptor cDNA

Design of Polymerase Chain Reaction (PCR) Primers

The primers were designed by careful examination of the sequence homologies in the membrane spanning segments 3 and 6 of the earlier cloned G-protein coupled receptors. The design of the primers was not inclined towards any one receptor or any one class of the receptors. The primers were degenerate (redundancy=8 for primer from segment 3 and redundancy=32 for primer from segment 6) and also had an inert nucleotide called deoxyinosine at places which otherwise would have become highly degenerate. The primers were chemically synthesized on a custom order basis by Symbicom AB (Tvistevägen 48, Umeå, Sweden). Primers were synthesized with EcoRI (segment 3) and BamHI (segment 6) linkers at the 5'-ends to facilitate the cloning.

The primer sequences are shown in SEQ ID NO: 3 and SEQ ID NO: 4.

Polymerase Chain Reaction (PCR) on Human Genomic DNA

One μg of human genomic DNA (Purchased from Clontech Laboratories Incorporated 4030 Fabian Way, Palo Alto Calif. 94303 USA) was subjected to PCR using the above described primers. The PCR was done in a final volume of 50 μl. It contained one μg of human genomic DNA, 10 mM Tris-HCl pH 8.3, 50 mM KCl, 1.5 mM $MgCl_2$, 0.001% gelatin, 200 μM of each deoxynucleotide, 1 μM of each primer and 1 unit of the enzyme Taq DNA polymerase (enzyme was obtained from Perkin Elmer Cetus, 761 Main Av., Noewalk, Conn. 06859, USA).

The PCR thermal profile used was 93° C. for 60 seconds, 55° C. for 40 seconds and 72° C. for 60 seconds for a total of 25 cycles, using a thermal Cycler (Hybaid, 111-113 Waldegrave road, Teddington, Middlesex, TW11 8LL, UK).

Ten percent of the reaction was analyzed by agarose gel electrophoresis, using the standard methods (Sambrook et al. 1989) (see FIG. 1). Three products were identified at approximately 705 bp, 501 bp and 372 bp. The 705 and 501 bp products were later identified as DNA for two of the already cloned receptors, but the 372 bp product was identified as a novel G-protein coupled receptor, and was the only one processed further.

Sequencing of the 372 bp Product

The 372 bp product was cloned into the pGEM7zf(+) vector (Promega Corp. Madison, Wis., USA) using the standard techniques (Sambrook et al. 1989) and one of the resulting plasmid termed as GE4 was sequenced using the chain termination method (Sanger et al. 1977). It was found to contain the sequence shown in SEQ ID NO: 11.

Tissue Distribution of the GE4 mRNA

Figure 2:
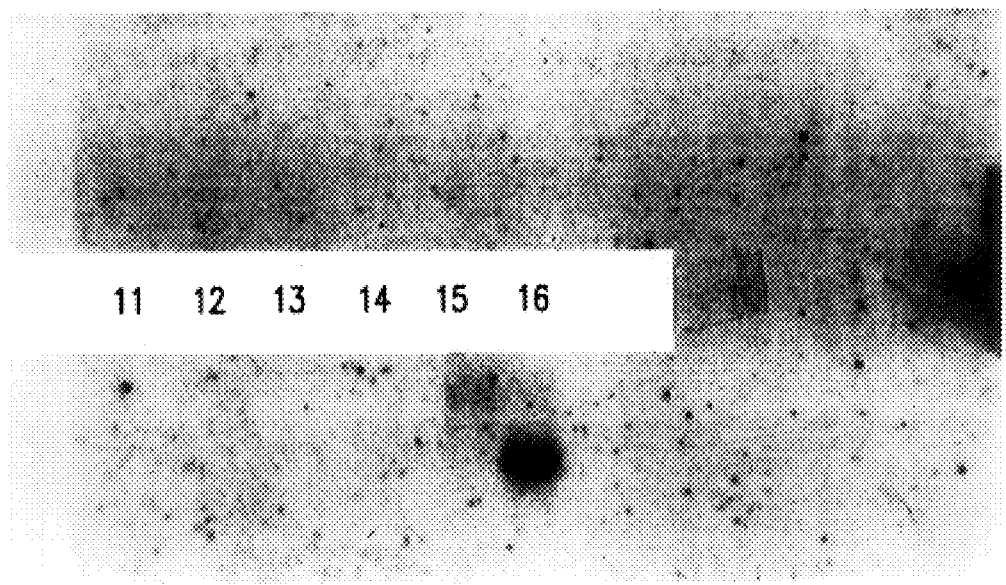

Poly(A)+ RNA was prepared using the oligo-dT purification scheme as described in standard protocols (Sambrook et al. 1989) from the following tissues: brain, thymus, parathyroid gland, parotid gland, salivary gland, adrenal gland, testis, liver, lung, heart, spleen, skeletal muscle, intestine, colon and WM 266-4 human melanoma cells (ATCC # CRL 1676). Ten µg of Poly(A)$^+$ RNA was subjected to electrophoresis through a 0.8% agarose-formaldehyde gel as described (Sambrook et al. 1989). The RNA was then blotted on to a Genescreen membrane (New England Nuclear, USA), and cross linked to the membrane with UV light. The membrane was then placed in a sealed plastic bag containing 10 ml of prehybridization solution (50% formamide, 5×SSC, 5×Denhardt's solution, 0.1% SDS, 10 mM Sodium phosphate pH 7.0, 10 mM EDTA and 100 µg/ml denatured calf thymus DNA) at 42° C. for 4 hours. The prehybridization solution was then replaced with the 10 ml of hybridization solution (10 ml prehybridization solution+$^{32}$p labelled GE4 DNA probe). The GE4 DNA was labelled with $^{32}$p using a commercial multiprime kit (Amersham, Aylesbury, Buckinghamshire, HP20 1BR, U.K.). The membrane was left in the hybridization solution for 12 hours at 42° C. The membrane was then washed in a solution of 0.1×SSC and 0.1% SDS at 60° C. for 30 minutes, air dried and then exposed to autoradiographic film for 16 hours. See FIG. 2. A positive signal can only be seen in the lane #16, which is for human melanoma WM 266-4 cells.

Construction and Screening of the cDNA Library from WM 266-4 Cells

The WM 266-4 cells were obtained from ATCC, Bethesda, Md., USA. The cells were grown in the medium as advised by the ATCC. Poly(A)$^+$ RNA from these cells was made using the fast track mRNA isolation kit (InVitrogen corp., 3985 Sorrento Valley Blvd. #B, San Diego, Calif. 92121, USA). Five µg of this RNA was then used to make a random primed cDNA library in the lambda gt11 vector using the materials and the conditions described by the manufacturer of the kit used (Amersham, Aylesbury, Buckinghamshire, HP20 1BR, U.K.).

Approximately 7×10$^5$ plaque forming units from the unamplified library were plated on the agar-LB plates (Sambrook et al. 1989), grown for 8 hours and were then transferred to Hybond-C filter discs (Amersham, Aylesbury, Buckinghamshire, HP20 1BR, U.K.). The DNA on the filter discs was then denatured and fixed as described (Sambrook 1989). The filter discs were then placed in sealed bags (4 filters/bag) containing the prehybridization solution (6×SSC, 5×Denhardt's solution, 10 mM sodium phosphate pH 7.0, 1 mM EDTA, 0.5% SDS and 0.1 mg/ml of denatured Salmon testis DNA) for 6 hours at 60° C. The filters were then placed in the hybridization solution (prehybridization solution+$^{32}$P-labelled GE4 DNA probe), for 12 hours at 60° C. The GE4 DNA was labelled with $^{32}$P using a commercial multiprime kit (Amersham, Aylesbury, Buckinghamshire, HP20 1BR, U.K.). The filters were then washed at 65° C. in a solution of 0.1×SSC and 0.1% SDS for 20 minutes, air dried and then exposed to the autoradiographic film for 24 hours. The positive plaques were picked and after repeating the screening for two more times a positive plaque designated 11 D was isolated.

Subcloning and Sequencing of the 11D cDNA

Figure 3:
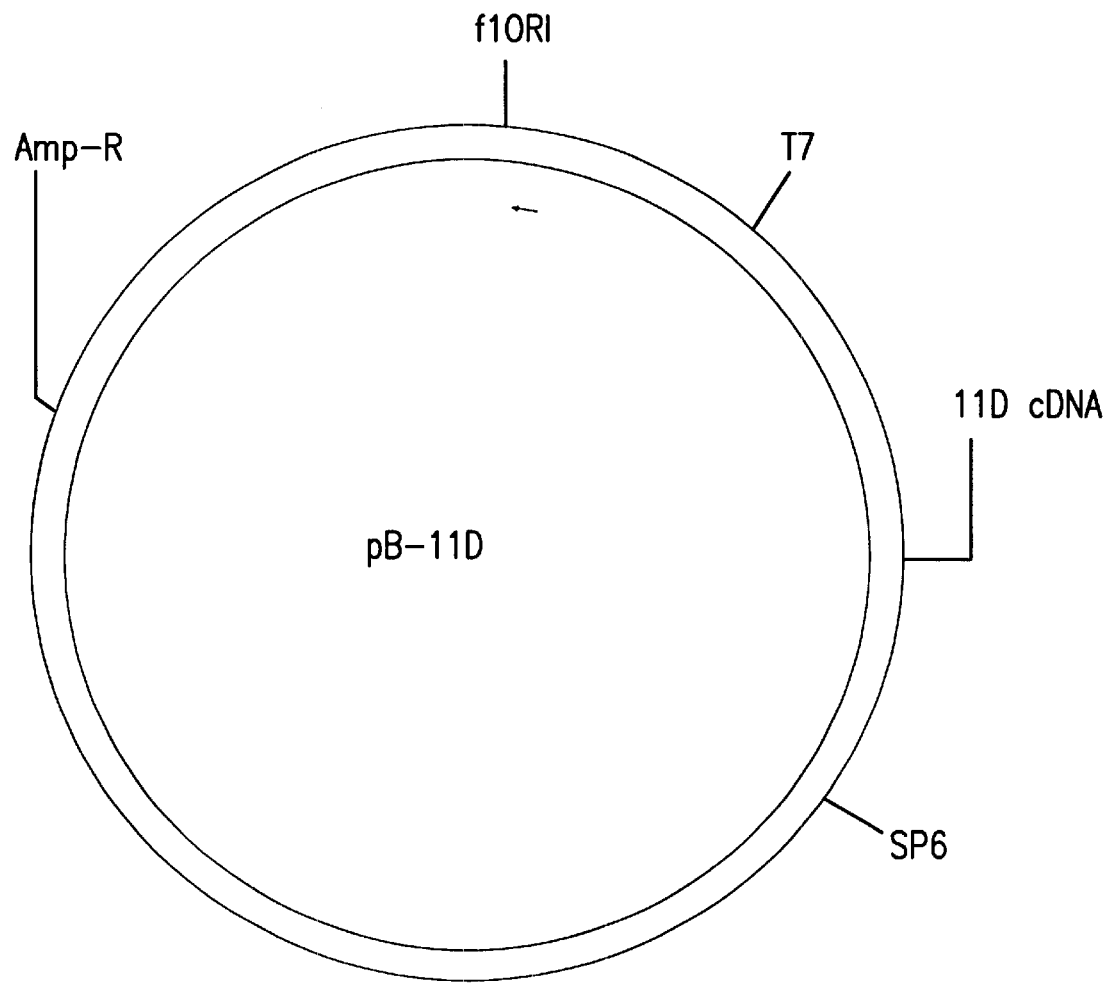

A large scale lambda DNA preparation was made for the 11D clone as described (Sambrook et Al. 1989). The insert was excised out with the EcoRI and HindIII enzymes. This took out all of the coding and 5'-untranslated sequences with part of the 3'-untranslated sequence. The EcoRI-HindIII fragment was cloned between the EcoRI and Hind III sites of the pGEM7Zf(+) vector (Promega Corp., Madison, Wis., USA) using the standard methods described (Sambrook 1989). The resulting plasmid DNA (See FIG. 3; pB-11D) was then transfected into competent DH5alfa E.Coli (BRL, 8400 Helgerman court, Gaithersburg, Md. 20877, USA). Bacterial colonies were grown on agar plates containing ampicillin. Individual colonies were picked in ampicillin containing 5 ml LB medium (Sambrook 1989) and grown overnight. Plasmid DNA was prepared as described (Sambrook 1989). Prepared plasmid DNAs were checked for the presence of 11D cDNA in correct position. The plasmid constructs with 11D cDNA in correct position were then amplified further in 500 ml cultures. Plasmid DNA from such large scale preparations were prepared with Qiagen Kits (Qiagen Inc., 11712 Moorpark Street, Studio City, Calif. 91604, USA). Both the strands of DNA in the entire coding sequence and the 5'-untranslated region and a small portion of the 3'-untranslated region were sequenced by making the over-lapping fragments. The method of sequencing was the chain termination method (Sanger et al. 1977). The cloned 11D cDNA was found to have the nucleotide sequence shown in SEQ ID NO: 1 and was shown to contain 7 hydrophobic segments (corresponding to nucleotides 286–351, 394–465, 517–588, 640–711, 733–804, 898–972 and 997–1068 in SEQ ID NO: 1, respectively).

Example 2

Cloning of the 11D cDNA into an Expression Vector

The expression vector pcDNAI (Invitrogen Corp., 3985 Sorrento Valley Blvd. #B, San Diego, Calif. 92121, USA), is a 4.2 kb multifunctional eukaryotic expression vector. It has the human CMV promoter and enhancer for high level expression.

Figure 4:
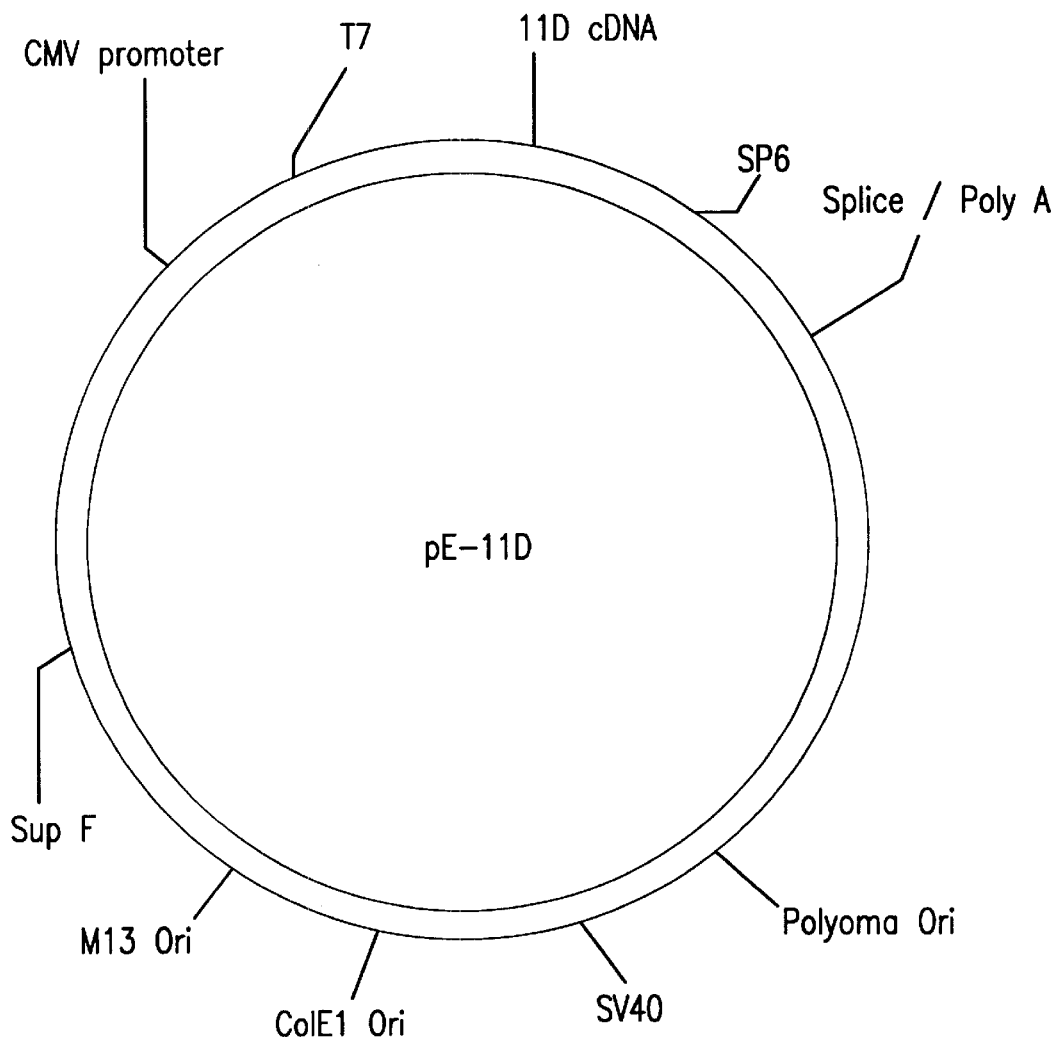

The 11D cDNA was excised from pGEM7Zf(+) vector (described above in 5.1.6) with EcoRI and NsiI enzymes, and ligated into the same sites of pcDNAI vector. The resulting plasmid DNA (See FIG. 4; pE-11D) was then transfected into competent MC1061/P3 E. Coli. Bacterial colonies were grown on agar plates containing ampicillin. Individual colonies were picked in 5 ml LB-ampicillin medium (Sambrook 1989) and grown overnight. Plasmid DNA was prepared as described (Sambrook 1989). Prepared plasmid DNAs were checked for the presence of 11D cDNA in correct position. The plasmid constructs with 11D cDNA in correct position were then amplified further in 500 ml cultures. Plasmid DNA from such large scale preparations were prepared with Qiagen Kits (Qiagen Inc., 11712 Moorpark street, Studio city, Calif. 91604, USA).

Example 3

Expression of the 11D cDNA and Establishment of its Identity

Figure 5:
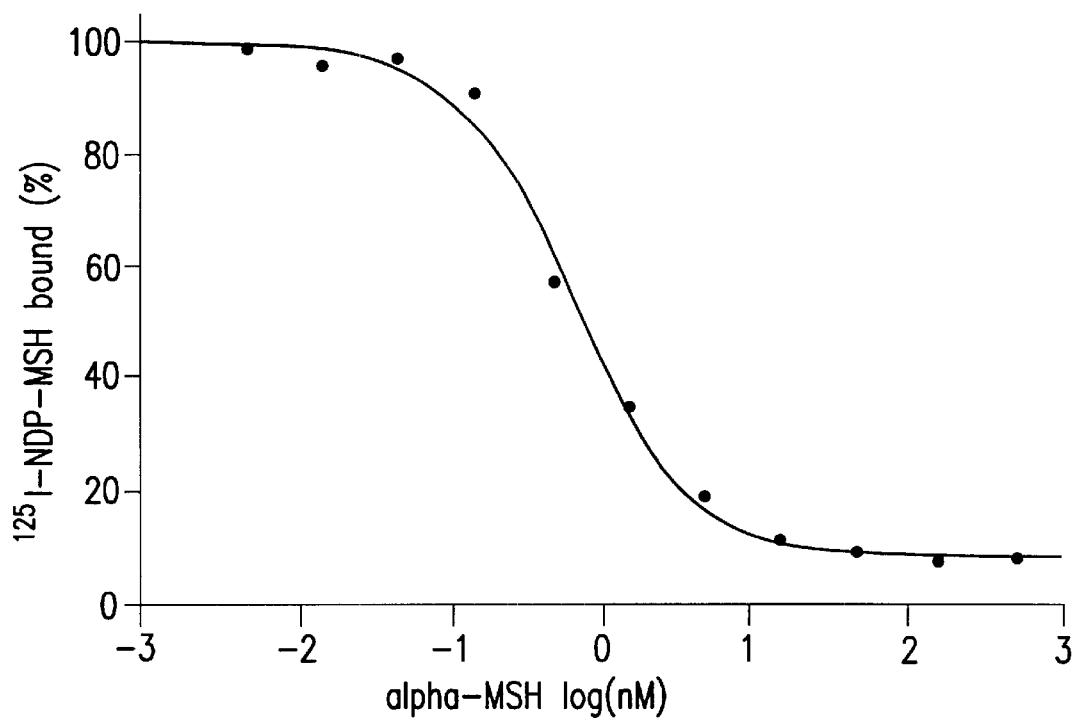

The WM266-4 human melanoma cells (from which the MSH receptor cDNA has been cloned) were grown under conditions described by ATCC. These cells were subjected to radioligand binding as described below for the transfected COS-7 cells. The WM-266-4 cells were shown to bind the $^{125}$I-labelled NDP-MSH in a specific manner. (FIG. 5)

Figure 6:
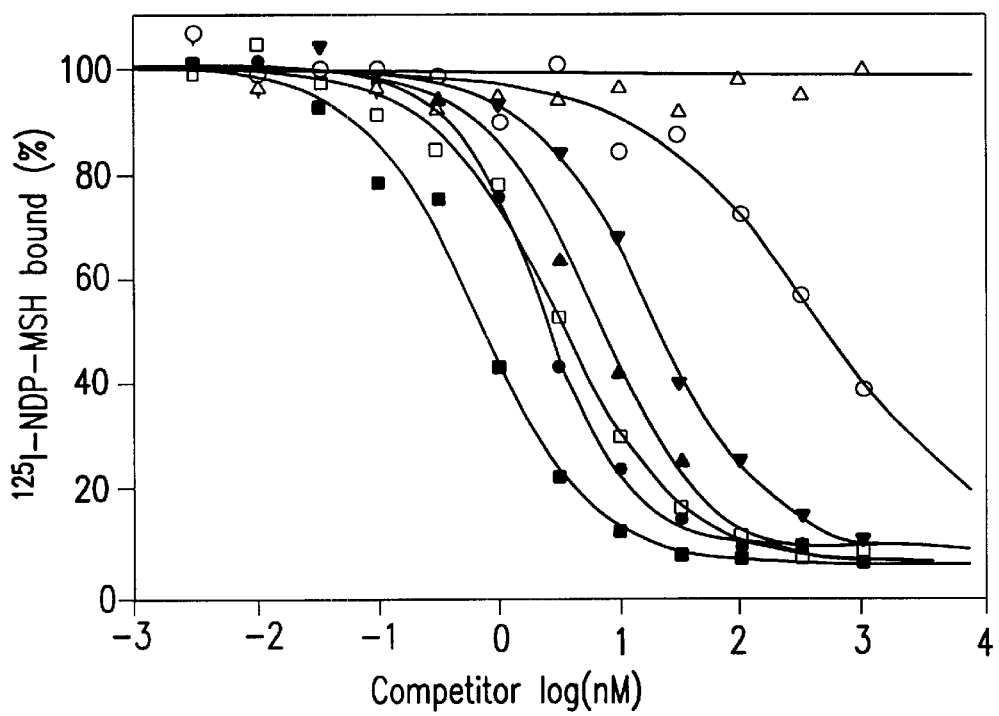

COS-7 cells were grown in Dulbecco's modified Eagle medium with 8% foetal calf serum and non-essential amino acids (Gibco/BRL, 8400 Helgerman Court, Gaithersburg, Md. 20877, USA). Eighty percent confluent cultures were transfected with 1 µg of pE-11D plasmid DNA and 40 µg lipofectin (BRL, 8400 Helgerman Court, Gaithersburg, Md. 20877, USA) in serum free medium. Five hours after transfection, serum containing medium was replaced, and cells were cultivated for 20 hours. Cells were then scraped off, centrifuged, resuspended in serum containing medium, plated on 48 well plates, and allowed to grow for 24 hours. The cells were then washed with 0.3 ml of binding buffer (minimum essential medium with Earle's salts, 25 mM HEPES pH 7.0, 0.2% bovine serum albumin, 1 mM 1,10-phenanthroline, 0.5 mg per liter leupeptine and 200 mg per liter bacitracin) and then incubated at 37° C. for 2 hours with 0.3 ml binding buffer containing 24,000 cpm of $^{125}$I-NDP-MSH and appropriate concentration of unlabelled peptides. NDP-MSH was labelled with $^{125}$Iodine (see below for details) to the specific activity of $8.6 \times 10^4$ cpm per Mol. The plates were then put on ice, cells washed with 0.3 ml of ice cold binding buffer and detached from plates with 0.3 ml of 0.1 N NaOH. Radioactivity was counted and data analyzed by iterative, non-linear curve fitting programme suitable for radioligand binding analysis (see FIG. 6). A series of POMC (pro-opiomelanocortin) derived peptides (purchased from Saxon Biochemicals GmbH, Hannover, Germany) showed differential potencies in inhibiting $^{125}$I-NDP-MSH binding to pE-11D transfected COS-7 cells. The potencies and reciprocals of binding affinities ($K_i$s) were determined by testing several (e.g. 11–12) concentrations of every tested peptide and fitting the data for the counts found to be bound to the cells to the four parameter logistic function using non-linear regression analysis using previously described methods (Bergström and Wikberg 1986). The $K_i$-values were then calculated from the IC-50 values estimated thus estimated by using the Cheng and Prusoff equation, as previously described (Cheng and Prusoff 1973). The potency order and $K_i$ values found from the analysis were NDP-MSH ($K_i$=23±0.5 pM)>α-MSH ($K_i$=92±19 pM)>ACTH (1–39) ($K_i$=170±37 pM)>μ-MSH ($K_i$=449±74 pM)>γ-MSH ($K_i$=1010±200 pM). ACTH (4–10) showed very low binding affinity ($K_i$=22,400±7200 pM), whereas the non-melanotropic POMC peptide β-endorphin showed no affinity for the expressed MSH receptor. These results conclusively prove that the cloned DNA of the invention is the MSH receptor cDNA.

Iodination of NDP-MSH

Four μg of the peptide NDP-MSH was iodinated with 1 mCi of 125-iodine using the Iodobeads (Pierce, Rockford, Ill., USA) in 100 mM sodium phosphate buffer (pH 6.5) for 10 minutes. The Iodobead was then removed from the solution which was applied to the C-18 reverse phase chromatography cartridge pre-equilibrated with 15% acetonitrile/0.05 M ammonium acetate pH 5.8. The cartridge was washed with 5 ml of the pre-equilibration buffer and then eluted at a flow rate of 1 ml/minute using a peristaltic pump. The elution gradient was 15% to 35% of acetonitrile containing 0.05 M ammonium acetate pH 5.8. Fractions of 1 ml were collected and the radioactivity determined by counting 2.5 μl from each fraction on to a gamma counter. Fractions 25 to 29 were pooled, dried under vacuum and redissolved in 1 ml water. The radioactivity was counted and the specific activity was calculated.

Example 4

Identification of DNA Sequences Related to the Cloned MSH Receptor cDNA

Two PCR primers were designed based on the sequence of the cloned MSH receptor cDNA. Their nucleotide sequences are shown in SEQ ID NO: 13 and in SEQ ID NO: 14, respectively.

These primers were used to perform PCR on human genomic DNA in exactly the same way as described in Example 2 except for the thermal profile, which was 94° C. for 30 sec, 45° C. for 20 sec, 72° C. for 20 sec for 5 cycles and then 94° C. for 30 sec, 60° C. for 20 sec, 72° C. for 20 sec for 25 cycles. Ten percent of the reaction was analyzed by agarose gel electrophoresis, using the standard methods (Sambrook et al. 1989). The products obtained were cloned into the pGEM7zf(+) vector and sequenced to completion. They were shown to have the nucleotide sequences shown in SEQ ID NO: 5, SEQ ID NO: 7 and SEQ ID NO: 9, respectively.

Example 5

Cloning of the 11D cDNA into a Stable Expression Vector

Cloning of the 11D cDNA

The expression vector pRC/CMV (Invitrogen corp., 3985 Sorrento Valley Blvd. #B. San Diego, Calif. 92121, USA), is a 4.5 kb multifunctional eukaryotic expression vector. It has the CMV promoter and enhancer for high level expression, and neomycin gene for selection of stable transfectants.

The 11D cDNA was excised from pcDNA I vector as described in example 2 with Hind III enzyme and ligated into the same site of pRC/CMV vector. The resulting plasmid DNA was then transfected into competent INVαF' *E. coli*. Bacterial colonies were grown on agar containing ampicillin. Individual colonies were picked in 5 ml LB-ampicillin medium (Sambrook 1989) and grown overnight. Plasmid DNA was prepared as described (Sambrook 1989). Prepared plasmid DNAs were checked for the presence of 11D cDNA in correct position. The plasmid constructs with 11D cDNA in correct were then amplified further in 500 ml cultures. Plasmid DNA from such large scale preparations were prepared with Qiagen Kits (Qiagen Inc., 11712 Moorpark Street, Studio City, Calif. 91604, USA).

Stable Expression of the 11D cDNA

COS-7 cells (available from ATCC) were grown in Dulbecco's modified Eagle medium with 8% fetal calf serum and non-essential amino acids (Gibco/BRL, 8400 Helgerman Court, Gaithersburg, Md. 20877, USA) in serum free medium, five hours after transfection, serum containing medium was replaced, and cells were cultivated for 48 hours. At this time selection for the calls stably harbouring the pRC/CMV-11D plasmid was begun by growing the cells in neomycin (0.5 mg/ml) containing medium (selection medium). Selection procedure was continued for two weeks, replacing the selection medium every 4th day. surviving cells were collected and maintained in the selection medium. These cells constitute the stable cell line.

To investigate the binding properties cells were scraped off from the culture flask, centrifuged, resuspended in selection medium, plated on 48 well, and allowed to grow for 24 hours. The cells were then washed with 0.3 ml of binding buffer (minimum essential medium with Earle's salts, 25 mM HEPES pH 7.0, 0.2% bovine serum albumin, 1 mM 1,10-phenanthroline, 0.5 mg per liter leupeptine and 200 mg per liter bacitracin) and then incubated at 37° C. for 2 hours with 0.3 ml binding buffer containing 24,000 cpm of $^{125}$I-NDP-MSH and appropriate concentration of unlabelled peptides. NDP-MSH was labelled with $^{125}$Iodine as explained in example 3 to the specific activity of $8.6 \times 10^4$ cpm per Mol. The plates were then put on ice, cells washed with 0.3 ml of ice cold binding buffer and detached form plated with 0.3 ml of 0.1 N NaOH. Radioactivity was counted and data analyzed by an iterative, non-linear curve fitting programme suitable for radioligand binding analysis. A series of POMC (pro-opiomelanocortin) derived peptides (purchased from Saxon Biochemicals GMBH, Hannover, Germany) showed differential potencies in inhibiting $^{123}$I-NDP-MSH binding to the stable cell line. The potency order found from the analysis were NDP-MSH>α-MSH>ACTH(1–39)>β-

MSH>γ-MSH. ACTH(4–10) showed very low binding affinity, whereas the non-melanotropic POMC peptide β-endorphin showed no affinity for the expressed MSH receptor. These results conclusively prove that the cloned MSH receptor cDNA is produced and expressed in a stable cell line.

Example 6

Molecular Cloning and Nucleotide Sequencing of the Full Length Clone of G8 DNA

Screening of a Human Placental Genomic Library

A human genomic DNA library was purchased from Stratagene, USA. Approximately $7 \times 10^5$ plaque forming units from this library were plated on the agar-LB plates (Sambrook et al. 1989), grown for 8 hours and were then transferred to Hybond-N filter discs (Amersham, Aylesbury, Buckinghamshire, HP20 1BR, U.K.). The DNA on the filter discs was then denatured and fixed as described (Sambrook et al. 1989). The filter discs were then placed in sealed bags (4 filters/bag) containing the prehybridization solution (6×SSC, 5×Denhardt's solution, 10 mM sodium phosphate pH 7.0, 1 mM EDTA, 0.5% SDS and 0.1 mg/ml of denatured Salmon testis DNA) for 6 hours at 60° C. The filters were then placed in the hybridization solution (prehybridization solution+$^{32}$P-labelled G-8 DNA probe, as in SEQ ID NO: 7), for 12 hours at 60° C. The G-8 DNA was labelled with $^{32}$p using a commercial multiprime kit (Amersham, Aylesbury, Buckinghamshire, HP20 1BR, U.K.). The filters were then washed at 65° C. in a solution of 0.1×SSC and 0.1% SDS for 20 minutes, air dried and then exposed to the autoradiographic film for 24 hours. The positive plaques were picked and after repeating the screening for two more times a positive plaque containing a gene designated MC-2 was isolated.

Subcloning and Sequencing of the Full Length MC-2 DNA

Figure 7:
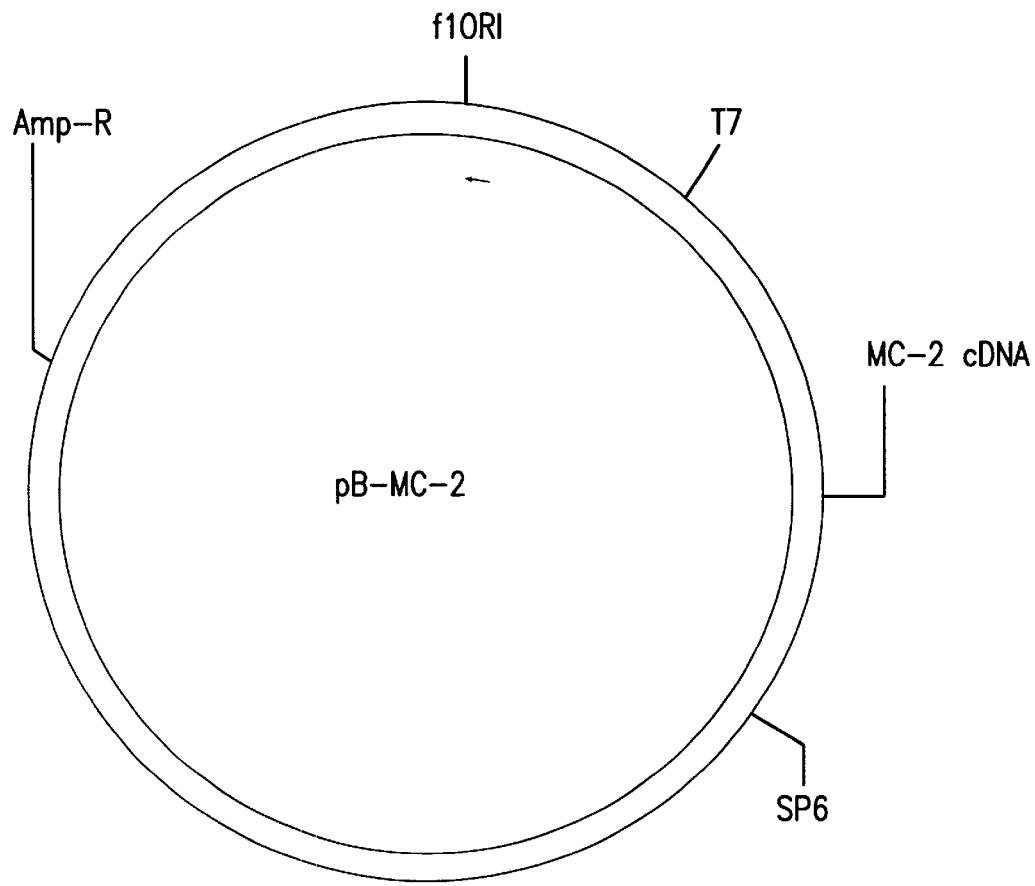

A large scale lambda DNA preparation was made for the MC-2 clone as described (Sambrook et al. 1989). The insert was excised out with the Sac I enzyme. This took out a 2.4 kb fragment containing all of the coding and a parts of 5'- and 3'-untranslated sequence. The Sac I fragment was cloned in the Sac I site of the pGEM5Zf(+) vector (Promega Corp., Madison, Wis., USA) using the standard methods described (Sambrook 1989). The resulting plasmid DNA pB-MC-2 (FIG. 7) was then transfected into competent DH5alfa E.Coli (BRL, 8400 Helgerman court, Gaithersburg, Md. 20877, USA). Bacterial colonies were grown on agar plates containing ampicillin. Individual colonies were picked in ampicillin containing 5 ml LB medium (Sambrook et al. 1989) and grown overnight. Plasmid DNA was prepared as described (Sambrook et al. 1989). Prepared plasmid DNAs were checked for the presence of MC-2 DNA in correct position. The plasmid constructs with MC-2 DNA in correct position were then amplified further in 500 ml cultures. Plasmid DNA from such large scale preparations were prepared with Qiagen Kits (Qiagen Inc., 11712 Moorpark Street, Studio City, Calif. 91604, USA). Both the strands of DNA in the entire coding sequence and the 5'-untranslated region and a small portion of the 3'-untranslated region were sequenced by making the overlapping fragments and primer walking. The method of sequencing was the chain termination method (Sanger et al. 1977). The cloned MC-2 DNA was found to contain the sequence shown in SEQ ID NO: 15.

Example 7

Cloning of the MC-2 DNA into an Expression Vector

The expression vector pRC/CMV (Invitrogen Corp., 3985 Sorrento Valley Blvd. #B, San Diego, Calif. 92121, USA), is a 4.5 kb multifunctional eukaryotic expression vector. It has the human CMV promoter and enhancer for high level expression.

Figure 8:
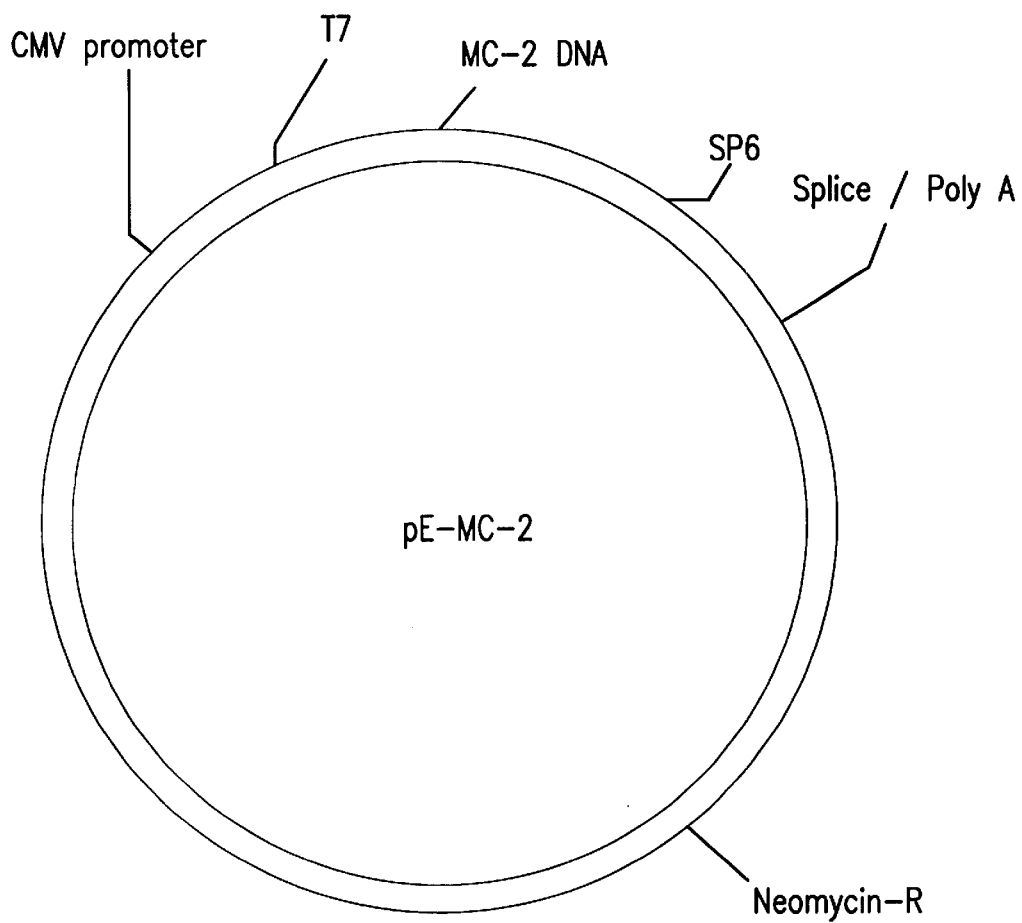

The MC-2 DNA (from nucleotide no. 520 to nucleotide no. 1620 from the seq. I.D. no. 15) was ligated between the HindIII and the XbaI sites of the pRC/CMV vector. The resulting plasmid DNA pE-MC-2 (FIG. 8) was then transfected into competent INVαF' E. coli. Bacterial colonies were grown on agar plates containing ampicillin. Individual colonies were picked in 5 ml LB-ampicillin medium (Sambrook et al. 1989) and grown overnight. Plasmid DNA was prepared as described (Sambrook et al. 1989). Prepared plasmid DNAs were checked for the presence of MC-2 DNA in the correct position. The plasmid constructs with MC-2 DNA in the correct position were then amplified further in 500 ml cultures. Plasmid DNA from such large scale preparations were prepared with Qiagen Kits (Qiagen Inc., 11712 Moorpark Street, Studio City, Calif. 91604, USA).

Example 8

Expression of the MC-2 DNA and Establishment of its Identity

Figure 9:
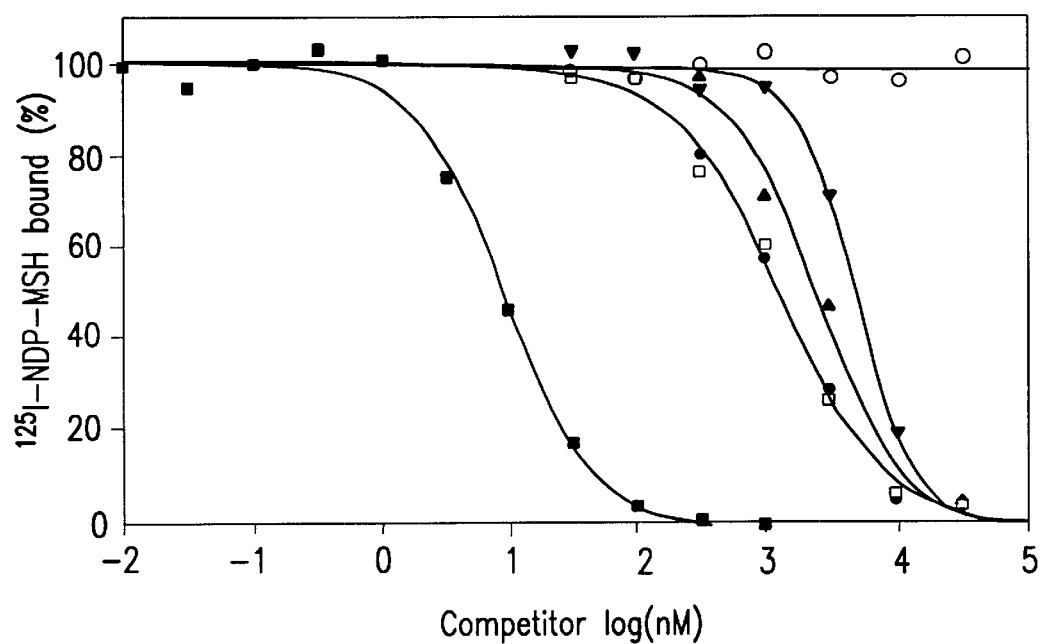

COS-7 cells were grown in Dulbecco's modified Eagle medium with 8% foetal calf serum and non-essential amino acids (Gibco/BRL, 8400 Helgerman Court, Gaithersburg, Md. 20877, USA). Eighty percent confluent cultures were transfected with 1 μg of pE-MC-2 plasmid DNA and 40 μg lipofectin (BRL, 8400 Helgerman Court, Gaithersburg, Md. 20877, USA) in serum free medium. Five hours after transfection, serum containing medium was replaced, and cells were cultivated for 20 hours. Cells were then scraped off, centrifuged, resuspended in serum containing medium, plated on 48 well plates, and allowed to grow for 24 hours. The cells were then washed with 0.3 ml of binding buffer (minimum essential medium with Earle's salts, 25 mM HEPES pH 7.0, 0.2% bovine serum albumin, 1 mM 1,10-phenanthroline, 0.5 mg per liter leupeptine and 200 mg per liter bacitracin) and then incubated at. 37° C. for 2 hours with 0.3 ml of binding buffer containing 24,000 cpm of $^{125}$I-NDP-MSH and appropriate concentration of unlabelled peptides. NDP-MSH was labelled with $^{125}$Iodine (see below for details) to the specific activity of 8.6×104 cpm per Mol. The plates were then put on ice, cells washed with 0.3 ml of ice cold binding buffer and detached from plates with 0.3 ml of 0.1 N NaOH. Radioactivity was counted and data analyzed by iterative, non-linear curve fitting programme suitable for radioligand binding analysis (see FIG. 9). A series of POMC (pro-opiomelanocortin) derived peptides (purchased from Saxon Biochemicals GmbH, Hannover, Germany) showed differential potencies in inhibiting $^{125}$I-NDP-MSH binding to pE-MC-2 transfected COS-7 cells. The potencies and reciprocals of binding affinities ($K_i$s) were determined by testing several (e.g. 10–12) concentrations of every tested peptide and fitting the data for the counts found to be bound to the cells to the four parameter logistic function using non-linear regression analysis using previously described methods (Bergström and Wikberg 1986). The $K_i$-values were then calculated from the IC-50 values estimated thus estimated by using the Cheng and Prusoff equation, as previously described (Cheng and Prusoff 1973). The potency order and $K_i$ values found from the analysis were NDP-MSH ($K_i$=5.18±0.54 nM)>α-MSH ($K_i$=928±314 nM)=ACTH (1–39) ($K_i$=929±389 nM)>β-MSH ($K_i$=1.75±0.67 μM)>γ-MSH ($K_i$=3.45±0.88 μM). The non-melanotropic POMC peptide β-endorphin showed no affinity for the expressed MC-2 receptor. These results conclusively prove that the cloned MC-2 DNA of the invention is a new member of the melanotropic receptor family.

Iodination of NDP-MSH: Four mg of the peptide NDP-MSH was iodinated with 1 μCi of $^{125}$Iodine using the Iodobeads (Pierce, Rockford, Ill., USA) in 100 mM sodium phosphate buffer (pH 6.5) for 10 minutes. The Iodobead was then removed from the solution which was applied to the C-18 reverse phase chromatography cartridge preequilibrated with 15% acetonitrile/0.05 M ammonium acetate pH 5.8. The cartridge was washed with 5 ml of the pre-equilibration buffer and then eluted at a flow rate of 1 ml/minute using a peristaltic pump. The elution gradient was 15% to 35% of acetonitrile containing 0.05 M ammonium acetate pH 5.8. Fractions of 1 ml were collected and the radioactivity determined by counting 2.5 µl from each fraction on to a gamma counter. Fractions 25 to 29 were pooled, dried under vacuum and redissolved in 1 ml of water. The radioactivity was counted and the specific activity was calculated.

Example 9

MC-2 RNA Detection by PCR Analysis

RNA from human brain tissue (purchased from Clontech, USA) and WM266-4 melanoma cells (made by Fast Track kit from Invitrogen Corp. USA) were reverse transcribed with Super-Script RNase H⁻ reverse transcriptase (BRL, USA). PCR was performed on samples before and after reverse transcription to rule out the possibility of genomic DNA contamination in RNA preparations. Five µg of RNA was used for reverse transcription and then all of it was used as template in the first PCR. The first PCR was performed with primers (described below as number 1 & 2) specific for the 5'- and 3'-untranslated regions of the MC-2 DNA. Ten percent of the first PCR reaction was then subjected to a second PCR with primers (described below as number 3 & 4) specific for the coding region of the clone MC-2.

Primer 1: 5'-GGAAGCTTTCTTTGGTAGGCTG (SEQ ID NO: 17)

Primer 2: 5'-GGTCTAGAGCCACAGAGAG
    GAG    (SEQ ID NO: 18)

Primer 3: 5'-CTGCATTTCTTGGATCT    (SEQ ID NO: 19)

Primer 4: 5'-AAGCTGCACATGGATGC    (SEQ ID NO: 20)

Figure 10:
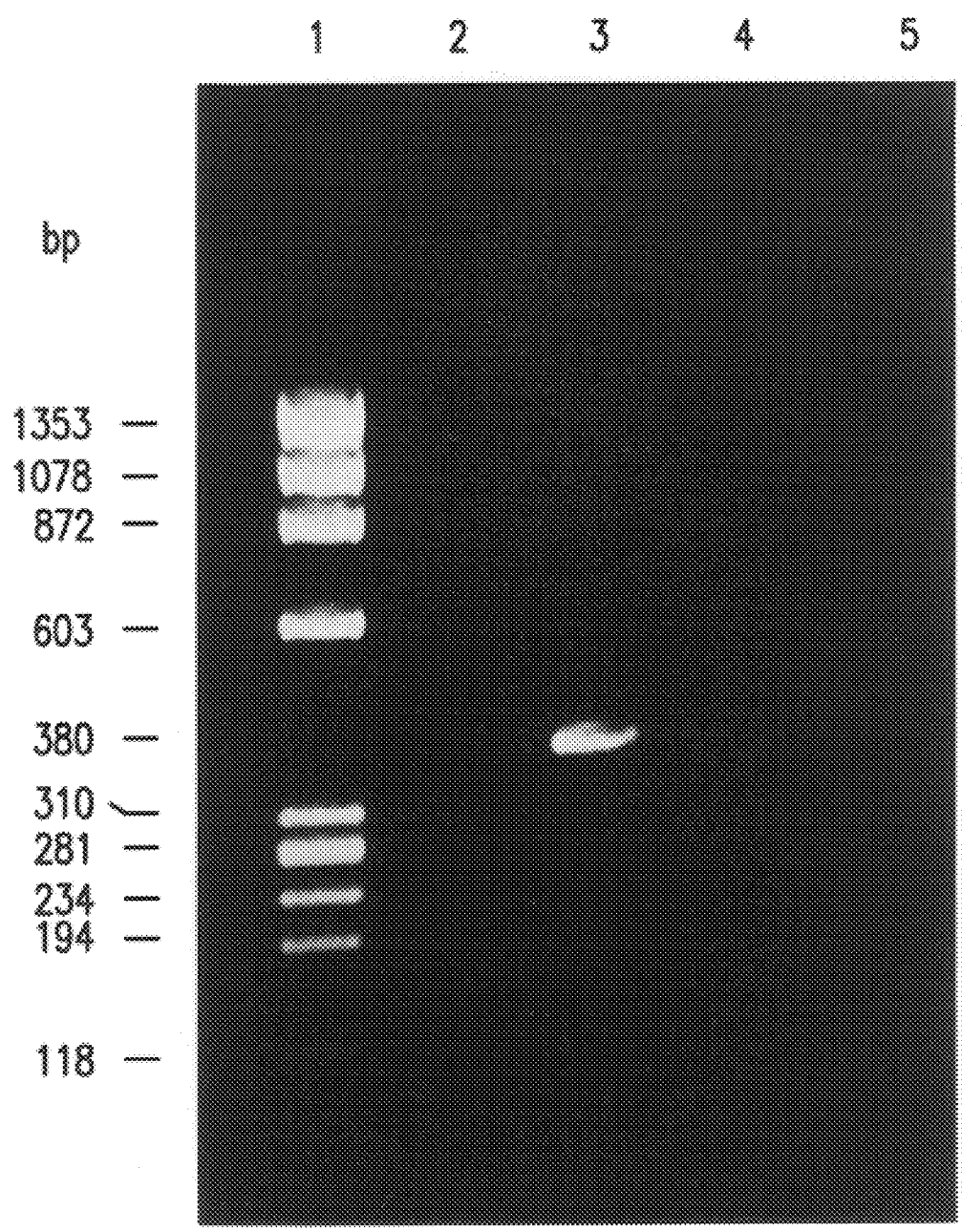

Both the PCRs were performed with Gene amplification kit (Perkin Elmer Cetus, USA). The PCR thermal profile used was 93° C. for 60 seconds, 55° C. for 40 seconds and 72° C. for 60 seconds for a total of 40 cycles. Fifty percent of the reaction was analyzed by agarose gel electrophoresis. The product was seen at the expected 380 bp position (FIG. 10).

Example 10

Development of Polyclonal Antibodies Against the MSH Receptor with Polypeptide Sequence According to SEQ ID NO: 2

The following two peptides, which were based on the polypeptide in SEQ ID NO: 2, were synthesized:

Peptide M1-Y, amino acids 4–19 of SEQ ID NO: 2:

Gln Gly Ser Gln Arg Arg Leu Leu Gly Ser Leu Asn Ser Thr Pro Cys

Peptide M2-Y, amino acids 25–35 of SEQ ID NO: 2:

Gly Leu Ala Ala Asn Gln Thr Gly Ala Arg Cys

The peptides were synthesized commercially by the multiple peptide system, U.S.A. The synthetic peptides were conjugated to thyroglobulin (THY) by use of the MBS method. This method allows coupling of the free sulfhydryl group of the cysteine-containing peptide onto the carrier protein via the bifunctional crosslinker MBS.

Immunization of Rabbits

Each of the THY-peptide (0.5 mg) conjugates were separately emulsified in Freund's complete adjuvant(1:1) and separately injected into SWL rabbits. After three weeks, the rabbits were given an additional booster injections with 0.5 mg of conjugate in incomplete adjuvant. Booster injection were then given with 4-weeks intervals, using the same procedure up until totally four booster injections had been given. Sera were collected 12–14 days after the last injection. A specimen of normal rabbits serum (pre-immune serum) was taken from each rabbit before immunization. All sera were aliquoted for storage at −80° C. before being used.

Antibody Screening

Cultured cells which were, respectively, expressing and not expressing the MSH receptor, were attached to poly-L-lysine coated slides for 24 hours, and the slides were then gently washed in PBS. (As MSH receptor expressing cells, COS-7 cells transfected with pE-11D, using the method described in Example 3 were used. As controls, which were not expressing MSH receptors, non-transfected COS-7 cells were used). The cells, being attached to the slides, were fixed in 4% paraformaldehyde for 10 minutes at 22° C. whereafter the slides were washed twice in PBS. Cells were then permeabilized by incubating in 0.2% Triton X-100 in PBS for 4 minutes at 22° C. and the slides were then again washed gently in PBS with 3 changes in 5 minutes intervals. Slides were then pre-incubated in 10% foetal calf serum for 30 minutes at 22° C. whereafter they were incubated with either the pre-immune sera diluted (1:100) or the antisera diluted (1:100) in 10% foetal calf serum, for 60 minutes at 22° C. After this procedure the slides were gently washed in PBS with 3 changes in 5 minute intervals. Slides were then incubated with TRITC-labelled anti-rabbit secondary antibody (diluted 1:40) for 60 minutes at 22° C. and then again washed gently in PBS with 3 changes in 5 minute intervals. The cells were then observed under a fluorescent microscope using appropriate filters for the correct wavelengths.

Results

The cells expressing the MSH receptor showed very little fluorescence when tested with pre-immunesera (reaction can be categorised as +).

The cells expressing the MSH receptor showed high fluorescence both when tested with antisera developed against Peptide M1-Y and when tested with antisera developed against Peptide M2-Y (The reaction can in both cases be categorised as ++++).

The control cells not expressing the MSH receptor showed very little fluorescence when tested with antisera developed against Peptide M1-Y or against Peptide M2-y (the reaction can, in both cases, be categorised as +).

6. REFERENCES

Clark, W G, M Holdeman & J M Lipton: Analysis of the antipyretic action of α-melanocyte stimulating hormone in rabbits. J. Physiol. 1985, 359, 459–465.

Findlay, J & E Eliopoulos: Three-dimensional modelling of G protein-linked receptors. TiPS. 1990, 11, 492–499.

Ghanem, G, J Verstegen, A Libert, R Arnould & F Lejeune: Alpha-melanocyte-stimulating hormone immunoreactivity in human melanoma metastases extracts. Pigment Cell Res. 1989, 2, 519–523.

Handelman, G E, T L O'Donohue, D Forrested & Cook: Alpha-melanocyte stimulating hormone facilitates learning of visual but not of auditory discriminations. Peptides. 1983, 4, 145–148.

Hirsch, M D & T L O'Donohue: Structural modifications of pro-opiomelanocortin.derived peptides alter their behavioural effects markedly. J. Pharmacol. Exp. Ther. 1986, 237, 378–385.

Ho, V C & A J Sober: Therapy for cutaneous melanoma: an update. J Am Acad Dermatol. 1990, 22, 159–176.

Kameyama, K, W D Vieira, K Tsukamoto, L W Law & V J Hearing: Differentiation and the tumorigenic and metastatic phenotype of murine melanoma cells. Gt J Cancer. 1990, 45, 1151–1158.

Liu, M A, S R Nussbaum & H N Eisen: Hormone conjugated with antibody to CD3 meidates cytotoxic T cell lysis of human melanoma cells. Science. 1988, 239, 395–398.

Murphy, T R, W Bishai, M Borowski, A Miyanohara, J Boyd & S Nagle: Genetic construction, expression, and melanoma-selective cytotoxicity of a diphtheria toxin-related alpha-melanocyte-stimulating hormone fusion protein. Proc Natl Acad Sci U S A. 1986, 83, 82588262.

Nordlund, J J: α-Melanocyte-stimulating hormone. A ubiquitous cytokine with pigmenting effects. JAMA. 1991, 266, 2753–2754.

Reid, R L, N Ling & S S C Yen: Gonadotropin-releasing activity of α-melanocyte stimulating hormone in normal subjects and in subjects with hypothalamic-pituitary dysfunction. J. Clin. Endocrinol. Metab. 1984, 58, 773–777.

Rheins, L A, A L Cotleur, R S Kleier, W B Hoppenjans, D N Sauder & J J Nordlund: Alpha-melanocyte stimulating hormone modulates contact hypersensitivity responsiveness in C57/BL6 mice. FASEB J. 1989, 3, 2282–2284.

Roses, D F, N S Karp, R Oratz, N Dubin, M N Harris, J Speyer, A Boyd, F M Golomb, J Ransohoff, M Dugan et al.: Survival with regional and distant metastases from cutaneous malignant melanoma. Surg. Gynecol. Obstet. 1991, 172, 262–268.

Sankara-Ramakrishnan, R & S Vishveshwara: A hydrogen bonded chain in bacteriorhodopsin by computer modelling approach. J Biomol Struct Dyn. 1989, 7, 187–205.

Tatro, J B, M Atkins, J W Mier, S Hardarson, H Wolfe, T Smith, M L Entwistle & S Reichuln: Melanotropin receptors demonstrated in situ in human melanoma. J Clin Invest. 1990a, 85, 1825–1832.

Tatro, J B, Z Wen, M L Entwistle, M B Atkins, T J Smith, S Reichlin & J R Murphy: Interaction of an alpha-melanocyte-stimulating hormone-diphtheria toxin fusion protein with melanotropin receptors in human melanoma metastases. Cancer Res. 1992, 52, 2545–2548.

Veith, J L, C A Sandman, J M George & V C Stevens: Effects of MSH/ACTH 4–10 on memory, attention, and endogenous hormone levels in women. Physiol. Behav. 1978, 20, 43–50.

Ward, M M, C A Sandman, J M George & H Shulman: MSH/ACTH 4–10 in men and women: effects upon performance of attention and memory task. Physiol. Behav. 1979, 22, 669–673.

Wen, Z L, X Tao, F Lakkis, T Kiyokawa & J R Murphy: Diphtheria toxin-related alpha-melanocyte-stimulating hormone fusion toxin. Internal in-frame deletion from Thr387 to His485 results in the formation of a highly potent fusion toxin which is resistant to proteolytic degradation. J Biol Chem. 1991, 266, 12289–12293.

Levine, N, Sheftel, S N, Eytan, T et al.: Induction of skin tanning by subcutaneous administration of a potent synthetic melanotropin. JAMA 1991, 266, 2730–2736.

Hibert, M F, Kallmeyer, S T, Bruinvels, A and Hoflack, J: Threedimensional models of neurotransmitter G-binding protein coupled receptors. Molecular Pharmacol. 1991, 40, 8–15.

Sambrook, J, Fritsch, E F and Maniatis, T: Molecular cloning—a laboratory manual. Cold Spring Harbor Laboratory press. 1989.

Wright, M S, Gautvik, V T, Gautvik, K M: Cloning strategies for peptide hormone receptors. Acta Endocrinol. 1992, 126, 97–104.

Xie, G-X, Miyajima, A, Goldstein, A: Expression cloning a cDNA encoding seven-helix receptor from human placenta with affinity for opioid ligands. Proc. Natl. Acad. Sci. USA. 1992, 89, 41244128.

Julius, D, MacDermott, A B, Axel, R, Jessel, T M: Molecular characterization of a functional cDNA encoding the serotonin 1c receptor. Science, 1988, 241, 558–564.

Masu, Y, Nakayama, K, Tamaki, H, Harada, Y, Kuno, M, Nakanishi, S: cDNA cloning of bovine substance-K receptor through oocyte expression system. Nature 1987, 329, 836–838.

Tindall, K R and Kunkel, T A: Fidelity of DNA synthesis by Thermud aquaticus DNA ploymerase. Biochemistry, 1988, 27, 6008–6013.

Tatro, J B and Reichlin, S: Specific receptors for alpha-melanocyte-stimulating hormone are widely distributed in tissues of rodents. Endocrinology, 1987, 121, 1900–1907

Tatro, J B, Entwistle, M L, Lester, B R and Reichlin, S: Melanotropin receptors of murine melanoma characterized in cultured cells and demonstrated in experimental tumours in situ. Cancer Research, 1990b 50, 1237–1242

Lerner, A B, Moellmann, G, Varga, J M, Halaban, R and Pawelek, J: Action of melanocyte stimulating hormone on pigment cells. Cell proliferation, 1989, 6, 187–197

Abdel-Malek, Z, Hadley, M E, Bregman, M D, Meyskens, F L and Hruby, V J: Actions of melanotropins on mouse melanoma cell growth in vitro. J. Natl. Cancer Inst., 1986, 76, 857–863.

Hart, I R, Rao, J and Wilson, R E: cAMP induced c-fos expression in cells of melanocyte origin. Biochem. Biophys. Res. Commun., 1989, 150, 408–413

Mac Neil, S, Dobson, J, Bleehen, S S and Buffey, J A: MSH increases intracellular calcium in melanoma cells. British J. of Dermatology, 1990, 123, 828

Buffey, J, Thody, A J, Bleehen, S S and Mac Neil, S: alpha-melanocyte-stimulating hormone stimulates protein kinase C activity in murine B16 melanoma. J. of Endocrinology, 1992, 133, 333–340

Allen, L F, Lefkowitz, R J, Caron, M G and Cotecchia, S: G-protein-coupled receptor genes as protooncogenes: Constitutively activating mutation of the alpha 1b-adrenergic receptor enhances mitogenesis and tumorigenicity. Proc. Natl. Acad. Sci. USA, 1991, 88, 11354–11358

Julius, D, Livelli, T J, Jessel, T M and Axel, R: Ectopic expression of the serotonin 1c receptor and the triggering of malignant transformation. Science, 1989, 244, 1057–1062

Lambrecht, R M, Packer, S and Wolf, A P, et al.: Detection of ocular melanoma with 4-(3-dimethylaminopropylamino)-7-(123I)-iodoquinoline. J. Nucl. Med., 1984, 25, 800–804

Coderre, J A, Packer, S and Fairchild, R G, et al.: Iodothiouracil as a melanoma localizing agent. J. Nucl. Med., 1986, 27, 1157–1164

Michelot, J M, Moreau, M C, Labarre, P G, et al.: Synthesis and evaluation of new iodine-125 radiopharmaceuticals as potential tracers for malignant melanoma. J. Nucl. Med., 1991, 32, 1573–1580

Eary, J F, Schroff, R W, Abrams, P G, et al.: Successful imaging of malignant melanoma with technetium-99m-labelled monoclonal antibodies. J. Nucl. Med., 1989, 30, 25–32

Larson, S M: Biologic characterization of melanoma tumors by antigen-specific targeting of radiolabelled anti-tumour antibodies. J. Nucl. Med., 1991, 32, 287–291

Mulligan, T M and Sowers, J R: Hyperpigmentation, vitiligo and Addison's disease. Cutis, 1982, 26, 317–322

Lerner, A B and McGuire, J S: Effects of alpha- and beta-melanocyte stimulating hormones on the skin colour of man. Nature, 1961, 189, 176–179

King, R A and Summers, C G : Albinism. Dermatol. Clin., 1988, 6, 217–228

Kyte, J and Dolittle, F F : A simple method for displaying the hydropathic character of a protein. J. Mol. Biol., 1982, 157, 105–132

Köhler, G and Milstein, C: Continuous cultures of fused cells secreting antibody of predefined specificity. Nature, 1985, 256, 495–497

Huse, W D, Sastry, L, Iverson, S, et al.: Generation of a large combinatorial library of the immunoglobulin repertoire in phage lambda. Science, 1989, 246, 1275–1281

Spirin, A S, Baranov, V I, Ryabova, L A, et al.: A continuous cell-free translation system capable of producing polypeptides in high yield. Science, 1988, 242, 1162–1164

Zozulya, S A, Gurevich, V V, Zvyaga, T A, et al.: Functional expression in vitro of bovine visual rhodopsin. Protein Engineering, 1990, 3, 453–458

Allen, J P, Feher, G, Yeates, T O, et al.: Structure of the reaction center from Rhodobacter sphaeroides R-26: the cofactors. Proc. Natl. Acad. Sci. USA, 1987, 84, 5730–5734

Henderson, R, Baldwin, J M, Ceska, T A, et al.: Model of the structure of bacteriorhodopsin based on high-resolution electron cryo-microscopy. J. Mol. Biol., 1990, 213, 899–929

Sanger, F, Nicklen, S and Coulson, A R: DNA sequencing with chain termination inhibitors. Proc. Natl. Acad. Sci. USA, 1977, 74, 5463–5467

Kozak, M: A scanning model for translation: An update. J. Cell Biol., 1989, 108, 229

Kennely, P J and Krebs, E G. Consensus sequences as substrate specificity determinants for protein kinases and protein phosphatases. J. Biol. Chem., 1991, 266, 15555–15558

Siegrist, W, et al.: Characterization of receptors for alpha-melanocyte-stimulating hormone on human melanoma cells. Cancer Research, 1989, 49, 6352–6358

Sunahara, R K et al.: Human dopamine D1 receptor encoded by an intronless gene on chromosome 5. Nature, 1990, 347, 80–83

Aktories, K & K H Jakobs: Epinephrine inhibits adenylate cyclase and stimulates a GTPase in human platelet membranes via alphaadrenoceptors. FEBS Letters. 1981, 130, 235–238.

Vachon, L, T Costa & A Hertz: Differential sensitivity of basal and opiod-stimulated low Km GTPase to guanine nucleotide analogs. J. Neurochem. 1986, 47, 1361–1369.

Wright, P E: What can two-dimensional NMR tell us about proteins?. TIBS. 1989, 14, 255–260.

Bergström, A & J E S Wikberg: Guanine nucleotides regulates both agonist and antagonist binding to cod brain alpha1-adrenoceptors. Acta pharmacol. toxicol. 1986, 59, 270–278.

Cheng, Y C & W H Prusoff: Relationship between the inhibition constant ($K_i$) and the concentration of inhibitor which cause 50 percent inhibition (I50) of an enzymatic reaction . Biochem. Pharmacol. 1973, 22, 3099–3108.

Sukhanov, V A, I M Voronkova, S V Shvets, V L Dyakov & L F Morozova: Melanocyte-stimulating hormone (alpha-MSH) inhibits the growth of human malignant melanoma cells with the induction of phosphatidyl inositol and myo-inositol phosphate levels. Biochem act. 1991, 24, 625–32.

Radunz, H E : Vom screening zum Drug Design—Moderne Methoden der Wirkstoff-Findung. Phar. Unser Zeit. 1988, 17, 161–176.

Burchill, S A, J M Marks & A J Thody: Tyrosinase synthesis in different skin types and the effects of alpha-melanocyte-stimulating hormone and cyclic AMP. J Invest Dermatol. 1990, 95, 558–61.

Traiffort, E and Ruat, M et al.: Expression of a cloned rat histamine H2 receptor mediating inhibition of arachidonate release and activation of cAMP accumulation. Proc. Natl. Acad. Sci. USA, 1992, 89, 2649–2653.

Gudermann, T, Birnbaumer, M and Birnbaumer, L: Evidence for dual coupling of the murine luteinizing hormone receptor to adenylate cyclase and phosphoinositide breakdown and $Ca^{2+}$ mobilization. J. Biol. Chem., 1992, 267, 4479–4488.

De Wied, D: Melanotropins as neuropeptides. In: The melanotropic peptides (Ed. H Vaudry and A N Eberle): Ann. NY Acad Sci. 1993, 680, 20–28.

Strand, F L et al.: Melanotropins as growth factors. In: The melanotropic peptides (Ed. H Vaudry and A N Eberle): Ann. NY Acad Sci. 1993, 680, 29–50.

Hnatowich, D J: Antibody radiolabeling, problems and promises. Nucl. Med. Biol. vol 17, 1, 49–55, 1990. Int. J. Radiat. Appl. Instrum. Part B.

Fritzberg, A E et al.: Specific and stable labelling of antibodies with technetium 99m with a diamide dithiolate chelating agent. Proc. Natl. Acad. Sci. 1988, 85, 4025–4029.

What is claimed is:

1. A purified DNA comprising a nucleotide sequence selected from the group consisting of
    (a) a nucleotide sequence encoding the amino acid sequence of amino acids 1–325 of SEQ ID NO:16; and
    (b) a nucleotide sequence encoding the melanocyte stimulating hormone receptor amino acid sequence encoded by the DNA clone contained in Deutsche Sammlung von Mikroorganismen Deposit NO. DSM 8440.

2. The purified DNA of claim 1, wherein said nucleotide sequence encodes the amino acid sequence of amino acids 1–325 of SEQ ID NO:16.

3. The purified DNA molecule of claim 2, wherein said amino acid sequence is encoded by bases 616–1590 of SEQ ID NO:15.

4. The purified DNA of claim 1, wherein said nucleotide sequence encodes the melanocyte stimulating hormone receptor amino acid sequence encoded by the DNA clone contained in Deutsche Sammlung von Mikroorganismen Deposit No. DSM 8440.

5. A vector comprising a nucleotide sequence from the group consisting of
    (a) a nucleotide sequence encoding the amino acid sequence of amino acids 1–325 of SEQ ID NO:16; and
    (b) a nucleotide sequence encoding the melanocyte stimulating hormone receptor amino acid sequence encoding by the DNA clone containing in Deutsche Sammlung von Mikroorganismen Deposit NO. DSM 8440.

6. The vector of claim 5, wherein said nucleotide sequence encodes the amino acid sequence of amino acids 1–325 of SEQ ID NO:16.

7. The vector of claim 6, wherein said amino acid sequence is encoded by bases 616–1590 of SEQ ID NO:15.

8. The vector of claim 5, wherein said nucleotide sequence encodes the melanocyte stimulating hormone receptor amino acid sequence encoded by the DNA clone contained in Deutsche Sammlung von Mikroorganismen Deposit No. DSM 8440.

9. The vector of claim 5, wherein said vector is an expression vector.

10. A method of making a host cell comprising a nucleotide sequence encoding a melanocyte stimulating hormone receptor, said method comprising transforming or transfecting a host cell with the vector of claim 5.

11. The host cell obtained by the method of claim 10.

12. A host cell comprising the vector of claim 5.

13. The host cell of claim 12, wherein said nucleotide sequence encodes the amino acid sequence of amino acids 1–325 of SEQ ID NO:16.

14. The host cell of claim 13, wherein said amino acid sequence is encoded by bases 616–1590 of SEQ ID NO:15.

15. The host cell of claim 12, wherein said nucleotide sequence encodes the melanocyte stimulating hormone receptor amino acid sequence encoded by the DNA clone contained in Deutsche Sammlung von Mikroorganismen Deposit No. DSM 8440.

16. The host cell of claim 12, wherein said host cell is capable of replicating said vector.

17. The host cell of claim 16 wherein said nucleotide sequence is integrated into the genome of said host cell.

18. The host cell of claim 12 wherein said host cell is capable of expressing said melanocyte stimulating hormone receptor, and wherein the expression of said melanocyte stimulating hormone receptor in said host cell is detectable in an NDP-MSH binding assay.

19. A composition comprising the host cell of claim 18, wherein said host cell is disrupted.

20. A method for expressing a melanocyte stimulating hormone receptor, said method comprising culturing the host cell of claim 12 under conditions suitable for expressing said melanocyte stimulating receptor, wherein the expression of said melanocyte stimulating hormone receptor in said host cell is detectable in an NDP-MSH binding assay.

21. A method for producing a melanocyte stimulating hormone receptor, said method comprising
    (a) culturing the host cell of claim 12 under conditions suitable for expressing said melanocyte stimulating hormone receptor; and
    (b) purifying said melanocyte stimulating hormone receptor.

22. A purified polypeptide comprising an amino acid sequence selected from the group consisting of
    (a) amino acids 1–325 of SEQ ID NO:16; and
    (b) the amino acid sequence of the melanocyte stimulating hormone receptor amino acid sequence encoded by the DNA clone contained in Deutsche Sammlung von Mikroorganismen Deposit No. DSM 8440.

23. The purified polypeptide of claim 22, wherein said polypeptide comprises a polypeptide having an amino acid sequence of amino acids 1–325 of SEQ ID NO:16.

24. The purified polypeptide of claim 22, wherein said polypeptide comprises a polypeptide having the amino acid sequence of the melanocyte stimulating hormone receptor amino acid sequence encoding by the DNA clone contained in Deutsche Sammlung von Mikroorganismen Deposit No. DSM 8440.

25. The purified polypeptide of claim 22, wherein said polypeptide further contains at least one modification selected from the group consisting of glycosylation, coupling to a carbohydrate or lipid moiety, the presence of a palmitoyl anchor or part thereof, detectable labeling, and coupling to a solid support.

26. The purified polypeptide of claim 22, said polypeptide being in substantially pure form.

27. The purified polypeptide of claim 22, said polypeptide being in lipid-soluble form.

28. A fusion polypeptide comprising a first polypeptide fused to a second polypeptide, wherein said first polypeptide comprises the polypeptide of claim 22.

29. A purified polypeptide selected form the group consisting of a polypeptide comprising amino acids from 1 to 37 in SEQ ID NO:16, a polypeptide comprising amino acids from 98 to 114 in SEQ ID NO:16, a polypeptide comprising amino acids from 180 to 186 in SEQ ID NO:16, a polypeptide comprising amino acids from 266 to 273 in SEQ ID NO:16, a polypeptide comprising amino acids from 62 to 73 in SEQ ID NO:16, a polypeptide comprising amino acids from 139 to 155 in SEQ ID NO:16, a polypeptide comprising amino acids from 212 to 239 in SEQ ID NO:16, a polypeptide comprising amino acids from 298 to 325 in SEQ ID NO:16, a polypeptide comprising amino acids from 38 to 61 in SEQ ID NO:16, a polypeptide comprising amino acids from 74 to 97 in SEQ ID NO:16, a polypeptide comprising amino acids from 115 to 138 in SEQ ID NO:16, a polypeptide comprising amino acids from 156–179 in SEQ ID NO:16, a polypeptide comprising amino acids from 187–211 in SEQ ID NO:16, a polypeptide comprising amino acids from 240 to 265 in SEQ ID NO:16, and a polypeptide comprising amino acids from 274 to 297 in SEQ ID NO:16.

30. A purified DNA consisting of a nucleotide sequence selected from the group consisting of
   (a) a nucleotide sequence encoding the amino acid sequence set forth in SEQ ID NO: 8; and
   (b) the nucleotide sequence set forth in SEQ ID NO:7.

31. The purified DNA of claim 30, wherein said nucleotide sequence encodes the amino acid sequence set forth in SEQ ID NO:8.

32. The purified DNA of claim 30, wherein said nucleotide sequence is that set forth in SEQ ID NO:7.

33. A vector comprising a nucleotide sequence selected from the group consisting of
   (a) a nucleotide sequence encoding the amino acid sequence set forth in SEQ ID NO:8; and
   (b) the nucleotide sequence set forth in SEQ ID NO:7.

34. The vector of claim 33, wherein said nucleotide sequence encodes the amino acid sequence set forth in SEQ ID NO:8.

35. A host cell comprising the vector of claim 34.

36. The vector of claim 33, wherein said nucleotide sequence is that set forth in SEQ ID NO:7.

37. A host cell comprising the vector of claim 36.

38. The vector of claim 33, wherein said vector is an expression vector.

39. A host cell comprising the vector of claim 33.

40. The host cell of claim 39, wherein said host cell is capable of replicating said vector.

41. The host cell of claim 40 wherein said nucleotide sequence is integrated into the genome of said host cell.

42. A composition comprising the host cell of claim 41, wherein said host cell is disrupted.

43. A method of making a host cell, said method comprising transforming or transfecting a host cell with the vector of claim 33.

44. The host cell obtained by the method of claim 43.

45. A purified polypeptide comprising the amino acid sequence set forth in SEQ ID No. 8.

46. The purified polypeptide of claim 45, wherein said polypeptide further contains at least one modification selected from the group consisting of glycosylation, coupling to a carbohydrate or lipid moiety, the presence of a palmitoyl anchor or part thereof, detectable labeling, and coupling to a solid support.

47. The purified polypeptide of claim 45, said polypeptide being in substantially pure form.

48. The purified polypeptide of claim 45, said polypeptide being in lipid-soluble form.

49. A fusion polypeptide comprising a first polypeptide fused to a second polypeptide, wherein said first polypeptide comprises the polypeptide of claim 45.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 1270 base pairs
      (B) TYPE: nucleic acid
      (C) STRANDEDNESS: double
      (D) TOPOLOGY: linear (ii) MOLECULE TYPE: DNA (cDNA)

(ix) FEATURE:
    (A) NAME/KEY: CDS
    (B) LOCATION: 169..1122

(xi) SEQUENCE DESCRIPTION: SEQ ID NO: 1:

```
GGAGAGGGTG TGAGGGCAGA TCTGGGGGTG CCCAGATGGA AGGAGGCAGG CATGGGGGAC      60

ACCCAAGGCC CCCTGGCAGC ACCATGAACT AAGCAGGACA CCTGGAGGGG AAGAACTGTG     120

GGGACCTGGA GGCCTCCAAC GACTCCTTCC TGCTTCCTGG ACAGGACT ATG GCT GTG     177
                                                   Met Ala Val
                                                    1

CAG GGA TCC CAG AGA AGA CTT CTG GGC TCC CTC AAC TCC ACC CCC ACA      225
Gln Gly Ser Gln Arg Arg Leu Leu Gly Ser Leu Asn Ser Thr Pro Thr
     5                  10                  15

GCC ATC CCC CAG CTG GGG CTG GCT GCC AAC CAG ACA GGA GCC CGG TGC      273
Ala Ile Pro Gln Leu Gly Leu Ala Ala Asn Gln Thr Gly Ala Arg Cys
 20                  25                  30                  35

CTG GAG GTG TCC ATC TCT GAC GGG CTC TTC CTC AGC CTG GGG CTG GTG      321
Leu Glu Val Ser Ile Ser Asp Gly Leu Phe Leu Ser Leu Gly Leu Val
                 40                  45                  50

AGC TTG GTG GAG AAC GCG CTG GTG GTG GCC ACC ATC GCC AAG AAC CGG      369
Ser Leu Val Glu Asn Ala Leu Val Val Ala Thr Ile Ala Lys Asn Arg
             55                  60                  65

AAC CTG CAC TCA CCC ATG TAC TGC TTC ATC TGC TGC CTG GCC TTG TCG      417
Asn Leu His Ser Pro Met Tyr Cys Phe Ile Cys Cys Leu Ala Leu Ser
         70                  75                  80

GAC CTG CTG GTG AGC GGG AGC AAC GTG CTG GAG ACG GCC GTC ATC CTC      465
Asp Leu Leu Val Ser Gly Ser Asn Val Leu Glu Thr Ala Val Ile Leu
 85                  90                  95

CTG CTG GAG GCC GGT GCA CTG GTG GCC CGG GCT GCG GTG CTG CAG CAG      513
Leu Leu Glu Ala Gly Ala Leu Val Ala Arg Ala Ala Val Leu Gln Gln
100                 105                 110                 115

CTG GAC AAT GTC ATT GAC GTG ATC ACC TGC AGC TCC ATG CTG TCC AGC      561
Leu Asp Asn Val Ile Asp Val Ile Thr Cys Ser Ser Met Leu Ser Ser
                120                 125                 130

CTC TGC TTC CTG GGC GCC ATC GCC GTG GAC CGC TAC ATC TCC ATC TTC      609
Leu Cys Phe Leu Gly Ala Ile Ala Val Asp Arg Tyr Ile Ser Ile Phe
            135                 140                 145

TAC GCA CTG CGC TAC CAC AGC ATC GTG ACC CTG CCG CGG GCG CGG CGA      657
Tyr Ala Leu Arg Tyr His Ser Ile Val Thr Leu Pro Arg Ala Arg Arg
        150                 155                 160

CGC GTT GCG GCC ATC TGG GTG GCC AGT GTC GTC TTC AGC ACG CTC TTC      705
Arg Val Ala Ala Ile Trp Val Ala Ser Val Val Phe Ser Thr Leu Phe
165                 170                 175

ATC GCC TAC TAC GAC CAC GTG GCC GTC CTG CTG TGC CTC GTG GTC TTC      753
Ile Ala Tyr Tyr Asp His Val Ala Val Leu Leu Cys Leu Val Val Phe
180                 185                 190                 195

TTC CTG GCT ATG CTG GTG CTC ATG GCC GTG CTG TAC GTC CAC ATG CTG      801
Phe Leu Ala Met Leu Val Leu Met Ala Val Leu Tyr Val His Met Leu
                200                 205                 210

GCC CGG GCC TGC CAG CAC GCC CAG GGC ATC GCC CGG CTC CAC AAG AGG      849
Ala Arg Ala Cys Gln His Ala Gln Gly Ile Ala Arg Leu His Lys Arg
            215                 220                 225

CAG CGC CCG GTC CAC CAG GGC TTT GGC CTT AAA GGC GCT GTC ACC CTC      897
Gln Arg Pro Val His Gln Gly Phe Gly Leu Lys Gly Ala Val Thr Leu
        230                 235                 240

ACC ATC CTG CTG GGC ATT TTC TTC CTC TGC TGG GGC CCC TTC TTC CTG      945
Thr Ile Leu Leu Gly Ile Phe Phe Leu Cys Trp Gly Pro Phe Phe Leu
```

```
            245                 250                 255
CAT CTC ACA CTC ATC GTC CTC TGC CCC GAG CAC CCC ACG TGC GGC TGC         993
His Leu Thr Leu Ile Val Leu Cys Pro Glu His Pro Thr Cys Gly Cys
260                 265                 270                 275

ATC TTC AAG AAC TTC AAC CTC TTT CTC GCC CTC ATC ATC TGC AAT GCC        1041
Ile Phe Lys Asn Phe Asn Leu Phe Leu Ala Leu Ile Ile Cys Asn Ala
                280                 285                 290

ATC ATC GAC CCC CTC ATC TAC GCC TTC CAC AGC CAG GAG CTC CGC AGG        1089
Ile Ile Asp Pro Leu Ile Tyr Ala Phe His Ser Gln Glu Leu Arg Arg
            295                 300                 305

ACG CTC AAG GAG GTG CTG ACA TGC TCC TGG TGAGCGCGGT GCACGCGCTT          1139
Thr Leu Lys Glu Val Leu Thr Cys Ser Trp
            310                 315

TAAGTGTGCT GGGCAGAGGG AGGTGGTGAT ATTGTGTGGT CTGGTTCCTG TGTGACCCTG      1199

GGCAGTTCCT TACCTCCCTG GTCCCCGTTT GTCAAAGAGG ATGGACTAAA TGATCTCTGA      1259

AAGTGTTGAA G                                                          1270
```

(2) INFORMATION FOR SEQ ID NO: 2:

(i) SEQUENCE CHARACTERISTICS:
        (A) LENGTH: 317 amino acids
        (B) TYPE: amino acid
        (D) TOPOLOGY: linear (ii) MOLECULE TYPE: polypeptide (xi) SEQUENCE DESCRIPTION: SEQ ID NO: 2:

```
Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Glu Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
            85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
130                 135                 140

Ser Ile Phe Tyr Ala Leu Arg Tyr His Ser Ile Val Thr Leu Pro Arg
145                 150                 155                 160

Ala Arg Arg Arg Val Ala Ala Ile Trp Val Ala Ser Val Val Phe Ser
            165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
```

```
225                 230                 235                 240
Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
    290                 295                 300

Leu Arg Arg Thr Leu Lys Glu Val Leu Thr Cys Ser Trp
305                 310                 315
```

(2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 3:

```
GGGAATTCTG TGTGTNATCN CNGTGGACCG GTA                              33
```

(2) INFORMATION FOR SEQ ID NO: 4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 4:

```
GGGGATCCGA AGAAGGGNAA CCAGCAGAGN ATGAA                            35
```

(2) INFORMATION FOR SEQ ID NO: 5:

(i) SEQUENCE CHARACTERISTICS:
        (A) LENGTH: 285 base pairs
        (B) TYPE: nucleic acid
        (C) STRANDEDNESS: double
        (D) TOPOLOGY: linear (ii) MOLECULE TYPE: DNA (PCR-fragment)

(ix) FEATURE:
        (A) NAME/KEY: CDS
        (B) LOCATION: 1..285

(xi) SEQUENCE DESCRIPTION: SEQ ID NO: 5:

```
TTC TAC GCA CTG CGC TAC CAC AGC ATC GTG ACC ATG CGC CGC ACT GTG    48
Phe Tyr Ala Leu Arg Tyr His Ser Ile Val Thr Met Arg Arg Thr Val
 1               5                  10                  15

GTG GTG CTT ACG GTC ATC TGG ACG TTC TGC ACG GGG ACT GGC ATC ACC    96
Val Val Leu Thr Val Ile Trp Thr Phe Cys Thr Gly Thr Gly Ile Thr
                20                  25                  30

ATG GTG ATC TTC TCC CAT CAT GTG CCC ACA GTG ATC ACC TTC ACG TCG   144
Met Val Ile Phe Ser His His Val Pro Thr Val Ile Thr Phe Thr Ser
             35                  40                  45

CTG TTC CCG CTG ATG CTG GTC TTC ATC CTG TGC CTC TAT GTG CAC ATG   192
Leu Phe Pro Leu Met Leu Val Phe Ile Leu Cys Leu Tyr Val His Met
         50                  55                  60
```

```
TTC CTG CTG GCT CGA TCC CAC ACC AGG AAG ATC TCC ACC CTC CCC AGA     240
Phe Leu Leu Ala Arg Ser His Thr Arg Lys Ile Ser Thr Leu Pro Arg
 65                  70                  75                  80

GCC AAC ATG AAA GGG GCC ATC ACC CTC ACC ATC CTG CTG GGC ATT         285
Ala Asn Met Lys Gly Ala Ile Thr Leu Thr Ile Leu Leu Gly Ile
                 85                  90                  95
```

(2) INFORMATION FOR SEQ ID NO: 6:

(i) SEQUENCE CHARACTERISTICS:
        (A) LENGTH: 95 amino acids
        (B) TYPE: amino acid
        (D) TOPOLOGY: linear (ii) MOLECULE TYPE: polypeptide (xi) SEQUENCE DESCRIPTION: SEQ ID NO: 6:

```
Phe Tyr Ala Leu Arg Tyr His Ser Ile Val Thr Met Arg Arg Thr Val
 1               5                  10                  15

Val Val Leu Thr Val Ile Trp Thr Phe Cys Thr Gly Thr Gly Ile Thr
                 20                  25                  30

Met Val Ile Phe Ser His His Val Pro Thr Val Ile Thr Phe Thr Ser
                 35                  40                  45

Leu Phe Pro Leu Met Leu Val Phe Ile Leu Cys Leu Tyr Val His Met
 50                  55                  60

Phe Leu Leu Ala Arg Ser His Thr Arg Lys Ile Ser Thr Leu Pro Arg
 65                  70                  75                  80

Ala Asn Met Lys Gly Ala Ile Thr Leu Thr Ile Leu Leu Gly Ile
                 85                  90                  95
```

(2) INFORMATION FOR SEQ ID NO: 7:

(i) SEQUENCE CHARACTERISTICS:
        (A) LENGTH: 306 base pairs
        (B) TYPE: nucleic acid
        (C) STRANDEDNESS: double
        (D) TOPOLOGY: linear (ii) MOLECULE TYPE: DNA (PCR-fragment)

(ix) FEATURE:
        (A) NAME/KEY: CDS
        (B) LOCATION: 1..306

(xi) SEQUENCE DESCRIPTION: SEQ ID NO: 7:

```
TTC TAC GCA CTG CGC TAC CAC AGC ATC GTG ACG GCG AGG CGC TCA GGG      48
Phe Tyr Ala Leu Arg Tyr His Ser Ile Val Thr Ala Arg Arg Ser Gly
 1               5                  10                  15

GCC ATC ATC GCC GGC ATC TGG GCT TTC TGC ACG GGC TGC GGC ATT GTC      96
Ala Ile Ile Ala Gly Ile Trp Ala Phe Cys Thr Gly Cys Gly Ile Val
                 20                  25                  30

TTC ATC CTG TAC TCA GAA TCC ACC TAC GTC ATC CTG TGC CTC ATC TCC     144
Phe Ile Leu Tyr Ser Glu Ser Thr Tyr Val Ile Leu Cys Leu Ile Ser
                 35                  40                  45

ATG TTC TTC GCT ATG CTG TTC CTC CTG GTG TCT CTG TAC ATA CAC ATG     192
Met Phe Phe Ala Met Leu Phe Leu Leu Val Ser Leu Tyr Ile His Met
                 50                  55                  60

TTC CTC CTG GCG CGG ACT CAC GTC AAG CGG ATC GCG CTC TGC CCG GGG     240
Phe Leu Leu Ala Arg Thr His Val Lys Arg Ile Ala Leu Cys Pro Gly
 65                  70                  75                  80

CCA GCT CTG CGC GGC AGA GGA CCA GCA TGC AGG GGC GCG GTC ACC CTC     288
Pro Ala Leu Arg Gly Arg Gly Pro Ala Cys Arg Gly Ala Val Thr Leu
                 85                  90                  95
```

```
ACC ATC CTG CTG GGC ATT                                              306
Thr Ile Leu Leu Gly Ile
        100

(2) INFORMATION FOR SEQ ID NO: 8:

(i) SEQUENCE CHARACTERISTICS:
        (A) LENGTH: 102 amino acids
        (B) TYPE: amino acid
        (D) TOPOLOGY: linear (ii) MOLECULE TYPE: polypeptide (xi) SEQUENCE DESCRIPTION: SEQ ID NO: 8:

Phe Tyr Ala Leu Arg Tyr His Ser Ile Val Thr Ala Arg Arg Ser Gly
 1               5                  10                  15

Ala Ile Ile Ala Gly Ile Trp Ala Phe Cys Thr Gly Cys Gly Ile Val
                20                  25                  30

Phe Ile Leu Tyr Ser Glu Ser Thr Tyr Val Ile Leu Cys Leu Ile Ser
            35                  40                  45

Met Phe Phe Ala Met Leu Phe Leu Leu Val Ser Leu Tyr Ile His Met
    50                  55                  60

Phe Leu Leu Ala Arg Thr His Val Lys Arg Ile Ala Leu Cys Pro Gly
65                  70                  75                  80

Pro Ala Leu Arg Gly Arg Gly Pro Ala Cys Arg Gly Ala Val Thr Leu
                85                  90                  95

Thr Ile Leu Leu Gly Ile
        100

(2) INFORMATION FOR SEQ ID NO: 9:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (ii) MOLECULE TYPE: DNA (PCR-fragment)

(ix) FEATURE:
        (A) NAME/KEY: CDS
        (B) LOCATION: 1..312

(xi) SEQUENCE DESCRIPTION: SEQ ID NO: 9:

TTC TAC GCA CTG CGT TAC CAC AGC ATC GTG ACC GTG CGG CGG GCC CTC    48
Phe Tyr Ala Leu Arg Tyr His Ser Ile Val Thr Val Arg Arg Ala Leu
 1               5                  10                  15

ACC TTG ATC GTG GCC ATC TGG GTC TGC TGC GGC GTC TGT GGC GTG GTG    96
Thr Leu Ile Val Ala Ile Trp Val Cys Cys Gly Val Cys Gly Val Val
                20                  25                  30

TTC ATC GTC TAC TCG GAG AGC AAA ATG GTC ATT GTG TGC CTC ATC ACC   144
Phe Ile Val Tyr Ser Glu Ser Lys Met Val Ile Val Cys Leu Ile Thr
            35                  40                  45

ATG TTC TTC GCC ATG ATG CTC CTC ATG GGC ACC CTC TAC GTG CAC ATG   192
Met Phe Phe Ala Met Met Leu Leu Met Gly Thr Leu Tyr Val His Met
    50                  55                  60

TTC CTC TTT GCG CGG CTG CAC GTC AAG CGC ATA GCA GCA CTG CCA CCT   240
Phe Leu Phe Ala Arg Leu His Val Lys Arg Ile Ala Ala Leu Pro Pro
65                  70                  75                  80

GCC GAC GGG GTG GCC CCA CAG CAA CAC TCA TGC ATG AAG GGG GCA GTC   288
Ala Asp Gly Val Ala Pro Gln Gln His Ser Cys Met Lys Gly Ala Val
                85                  90                  95
```

```
ACC CTC ACC ATC CTG CTG GGC ATT                                    312
Thr Leu Thr Ile Leu Leu Gly Ile
            100
```

(2) INFORMATION FOR SEQ ID NO: 10:

(i) SEQUENCE CHARACTERISTICS:
        (A) LENGTH: 104 amino acids
        (B) TYPE: amino acid
        (D) TOPOLOGY: linear (ii) MOLECULE TYPE: polypeptide (xi) SEQUENCE DESCRIPTION: SEQ ID NO: 10:

```
Phe Tyr Ala Leu Arg Tyr His Ser Ile Val Thr Val Arg Arg Ala Leu
 1               5                  10                  15

Thr Leu Ile Val Ala Ile Trp Val Cys Cys Gly Val Cys Gly Val Val
            20                  25                  30

Phe Ile Val Tyr Ser Glu Ser Lys Met Val Ile Val Cys Leu Ile Thr
            35                  40                  45

Met Phe Phe Ala Met Met Leu Leu Met Gly Thr Leu Tyr Val His Met
        50                  55                  60

Phe Leu Phe Ala Arg Leu His Val Lys Arg Ile Ala Ala Leu Pro Pro
65                  70                  75                  80

Ala Asp Gly Val Ala Pro Gln Gln His Ser Cys Met Lys Gly Ala Val
            85                  90                  95

Thr Leu Thr Ile Leu Leu Gly Ile
            100
```

(2) INFORMATION FOR SEQ ID NO: 11:

(i) SEQUENCE CHARACTERISTICS:
        (A) LENGTH: 372 base pairs
        (B) TYPE: nucleic acid
        (C) STRANDEDNESS: double
        (D) TOPOLOGY: linear (ii) MOLECULE TYPE: DNA (PCR-fragment)

(ix) FEATURE:
        (A) NAME/KEY: CDS
        (B) LOCATION: 1..372

(xi) SEQUENCE DESCRIPTION: SEQ ID NO: 11:

```
CTG TGT GTG ATC GCG CTG GAC CGG TAC ATC TCC ATC TTC TAC GCA CTG    48
Leu Cys Val Ile Ala Leu Asp Arg Tyr Ile Ser Ile Phe Tyr Ala Leu
 1               5                  10                  15

CGC TAC CAC AGC ATC GTG ACC CTG CCG CGG GCG CCG GAA GCC GTT GCG    96
Arg Tyr His Ser Ile Val Thr Leu Pro Arg Ala Pro Glu Ala Val Ala
            20                  25                  30

GCC ATC TGG GTG GCC AGT GTC GTC TTC AGC ACG CTC TTC ATC GCC TAC   144
Ala Ile Trp Val Ala Ser Val Val Phe Ser Thr Leu Phe Ile Ala Tyr
            35                  40                  45

TAC GAC CAC GTG GCC GTC CTG CTG TGC CTC GTG GTC TTC TTC CTG GCT   192
Tyr Asp His Val Ala Val Leu Leu Cys Leu Val Val Phe Phe Leu Ala
        50                  55                  60

ATG CTG GTG CTC ATG GCC GTG CTG TAC GTC CAC ATG CTG GCC CGG GCC   240
Met Leu Val Leu Met Ala Val Leu Tyr Val His Met Leu Ala Arg Ala
65                  70                  75                  80

TGC CAG CAC GCC CAG GGC ATC GCC CGG CTC CAC AAG AGG CAG CGC CCG   288
Cys Gln His Ala Gln Gly Ile Ala Arg Leu His Lys Arg Gln Arg Pro
            85                  90                  95

GTC CAC CAG GGC TTT GGC CTT AAA GGC GCT GTC ACC CTC ACC ATC CTG   336
```

Val His Gln Gly Phe Gly Leu Lys Gly Ala Val Thr Leu Thr Ile Leu
            100                 105                 110

CTG GGC ATT TTC ACC GTC TCG TGG CGC CCC TTC TTC                          372
Leu Gly Ile Phe Thr Val Ser Trp Arg Pro Phe Phe
        115                 120

(2) INFORMATION FOR SEQ ID NO: 12:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 12:

Leu Cys Val Ile Ala Leu Asp Arg Tyr Ile Ser Ile Phe Tyr Ala Leu
  1               5                  10                  15

Arg Tyr His Ser Ile Val Thr Leu Pro Arg Ala Pro Glu Ala Val Ala
            20                  25                  30

Ala Ile Trp Val Ala Ser Val Val Phe Ser Thr Leu Phe Ile Ala Tyr
            35                  40                  45

Tyr Asp His Val Ala Val Leu Leu Cys Leu Val Val Phe Phe Leu Ala
        50                  55                  60

Met Leu Val Leu Met Ala Val Leu Tyr Val His Met Leu Ala Arg Ala
 65                  70                  75                  80

Cys Gln His Ala Gln Gly Ile Ala Arg Leu His Lys Arg Gln Arg Pro
                85                  90                  95

Val His Gln Gly Phe Gly Leu Lys Gly Ala Val Thr Leu Thr Ile Leu
            100                 105                 110

Leu Gly Ile Phe Thr Val Ser Trp Arg Pro Phe Phe
        115                 120

(2) INFORMATION FOR SEQ ID NO: 13:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 13:

GGGAATTCTA CGCACTGCGC TACCACAGCA TCGTG                                    35

(2) INFORMATION FOR SEQ ID NO: 14:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: DNA (synthetic)

(xi) SEQUENCE DESCRIPTION: SEQ ID NO: 14:

GGGGATCCAA TGCCCAGCAG GATGGTGAGG GTGA                                     34

(2) INFORMATION FOR SEQ ID NO: 15:

(i) SEQUENCE CHARACTERISTICS:
        (A) LENGTH: 1650 base pairs
        (B) TYPE: nucleic acid

```
         (C) STRANDEDNESS: double
         (D) TOPOLOGY: linear (ii) MOLECULE TYPE: DNA (cDNA)

(ix) FEATURE:
         (A) NAME/KEY: CDS
         (B) LOCATION: 616..1590

(xi) SEQUENCE DESCRIPTION: SEQ ID NO: 15:

CTTGAGGAGA ATGTCGTGCA GTAGCCTTAG GAATGTGAAC ATTGGGAGAC TGGCTGGGAT      60

TTTGTAGGTT ATGAGAAGGG GACACTTATG ATATGTGAAC TTGAGCCCAG GAGAGAAGCC     120

ATAAAAAGTG AAACTGTCCT GGGCACTTGG AGGTGAGTGT CTCTCTAGTA AGATGCATGT     180

GAAAGGCCTG GGAGCTGAAA GCAAGGAGAG CAGAAGAGGC TGGTGAAGAT TCTAATCTGC     240

GTGTCCAGGG GCACTCTTCC AGGTCTCAGG AACGCAGGTC AGAATGTGCA AGCCAGCTGC     300

CGGGCACGTG GCTCACCCCT GTAGTACCAG CACTTTGGGA GGCTGAGAGA GAAGATCGCT     360

TGTGGCCAGG AGTTTGAGAC CAGACTGGGG CTTCATAGGG AGACCCTGTC TCTTAAAAAA     420

AAAAAAAAAA AAGGACTGAG TGAGCCGAGC CCAGTCCTCT CATGCACTGT GTCATTCATC     480

CCCTTTCTTA GGCTGTGTTG GTTCTAGGCT AGCTGCTGTC TTTCTTTGGT AGGCTGCTAA     540

CCTCTTTGGA TTGTGAATTT AAAACATGTT TTACAGTAAA TTTGCTGCCA AGACAAGAGG     600

TGTATTTCTC CAGCA ATG AAT TCC TCA TTT CAC CTG CAT TTC TTG GAT CTC      651
               Met Asn Ser Ser Phe His Leu His Phe Leu Asp Leu
                 1               5                  10

AAC CTG AAT GCC ACA GAG GGC AAC CTT TCA GGA CCC AAT GTC AAA AAC       699
Asn Leu Asn Ala Thr Glu Gly Asn Leu Ser Gly Pro Asn Val Lys Asn
             15                  20                  25

AAG TCT TCA CCA TGT GAA GAC ATG GGC ATT GCT GTG GAG GTG TTT CTC       747
Lys Ser Ser Pro Cys Glu Asp Met Gly Ile Ala Val Glu Val Phe Leu
 30                  35                  40

ACT CTG GGT GTC ATC AGC CTC TTG GAG AAC ATC TTG GTC ATA GGG GCC       795
Thr Leu Gly Val Ile Ser Leu Leu Glu Asn Ile Leu Val Ile Gly Ala
 45                  50                  55                  60

ATA GTG AAG AAC AAA AAC CTG CAC TCC CCC ATG TAC TTC TTC GTG TGC       843
Ile Val Lys Asn Lys Asn Leu His Ser Pro Met Tyr Phe Phe Val Cys
             65                  70                  75

AGC CTG GCA GTG GCG GAC ATG CTG GTG AGC ATG TCC AGT GCC TGG GAG       891
Ser Leu Ala Val Ala Asp Met Leu Val Ser Met Ser Ser Ala Trp Glu
         80                  85                  90

ACC ATC ACC ATC TAC CTA CTC AAC AAC AAG CAC CTA GTG ATA GCA GAC       939
Thr Ile Thr Ile Tyr Leu Leu Asn Asn Lys His Leu Val Ile Ala Asp
         95                 100                 105

GCC TTT GTG CGC CAC ATT GAC AAT GTG TTT GAC TCC ATG ATC TGC ATT       987
Ala Phe Val Arg His Ile Asp Asn Val Phe Asp Ser Met Ile Cys Ile
110                 115                 120

TCC GTG GTG GCA TCC ATG TGC AGC TTA CTG GCC ATT GCA GTG GAT AGG      1035
Ser Val Val Ala Ser Met Cys Ser Leu Leu Ala Ile Ala Val Asp Arg
125                 130                 135                 140

TAC GTC ACC ATC TTC TAC GCC CTG CGC TAC CAC CAC ATC ATG ACG GCG      1083
Tyr Val Thr Ile Phe Tyr Ala Leu Arg Tyr His His Ile Met Thr Ala
                145                 150                 155

AGG CGC TCA GGG GCC ATC ATC GCC GGC ATC TGG GCT TTC TGC ACG GGC      1131
Arg Arg Ser Gly Ala Ile Ile Ala Gly Ile Trp Ala Phe Cys Thr Gly
            160                 165                 170

TGC GGC ATT GTC TTC ATC CTG TAC TCA GAA TCC ACC TAC GTC ATC CTG      1179
Cys Gly Ile Val Phe Ile Leu Tyr Ser Glu Ser Thr Tyr Val Ile Leu
        175                 180                 185
```

```
TGC CTC ATC TCC ATG TTC TTC GCT ATG CTG TTC CTC CTG GTG TCT CTG    1227
Cys Leu Ile Ser Met Phe Phe Ala Met Leu Phe Leu Leu Val Ser Leu
    190                 195                 200

TAC ATA CAC ATG TTC CTC CTG GCG CGG ACT CAC GTC AAG CGG ATC GCG    1275
Tyr Ile His Met Phe Leu Leu Ala Arg Thr His Val Lys Arg Ile Ala
205                 210                 215                 220

CTC TGC CCG GGG CCA GCT CTG CGC GGC AGA GGA CCA GCA TGG CAG GGC    1323
Leu Cys Pro Gly Pro Ala Leu Arg Gly Arg Gly Pro Ala Trp Gln Gly
                225                 230                 235

GCG GTC ACC GTC ACC ATG CTG CTG GGC GTG TTT ACC GTG TGC TGG GCC    1371
Ala Val Thr Val Thr Met Leu Leu Gly Val Phe Thr Val Cys Trp Ala
        240                 245                 250

CCG TTC TTC CTT CAT CTC ACT TTA ATG CTT TCT TGC CCT CAG AAC CTC    1419
Pro Phe Phe Leu His Leu Thr Leu Met Leu Ser Cys Pro Gln Asn Leu
            255                 260                 265

TAC TGC TCT CGC TTC ATG TCT CAC TTC AAT ATG TAC CTC ATA CTC ATC    1467
Tyr Cys Ser Arg Phe Met Ser His Phe Asn Met Tyr Leu Ile Leu Ile
270                 275                 280

ATG TGT AAT TCC GTG ATG GAC CCT CTC ATA TAT GCC TTC CGC AGC CAA    1515
Met Cys Asn Ser Val Met Asp Pro Leu Ile Tyr Ala Phe Arg Ser Gln
285                 290                 295                 300

GAG ATG CGG AAG ACC TTT AAG GAG ATT ATT TGC TGC CGT GGT TTC AGG    1563
Glu Met Arg Lys Thr Phe Lys Glu Ile Ile Cys Cys Arg Gly Phe Arg
                305                 310                 315

ATC GCC TGC AGC TTT CCC AGA AGG GAT TAACGACAAA GTGCTCCTCT          1610
Ile Ala Cys Ser Phe Pro Arg Arg Asp
                320                 325

CTGTGGCTCT GTTCTCCTTT GTTTGCTCAC CTATGACAAA                        1650
```

(2) INFORMATION FOR SEQ ID NO: 16:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO: 16:

```
Met Asn Ser Ser Phe His Leu His Phe Leu Asp Leu Asn Leu Asn Ala
1               5                   10                  15

Thr Glu Gly Asn Leu Ser Gly Pro Asn Val Lys Asn Lys Ser Ser Pro
            20                  25                  30

Cys Glu Asp Met Gly Ile Ala Val Glu Val Phe Leu Thr Leu Gly Val
        35                  40                  45

Ile Ser Leu Leu Glu Asn Ile Leu Val Ile Gly Ala Ile Val Lys Asn
    50                  55                  60

Lys Asn Leu His Ser Pro Met Tyr Phe Phe Val Cys Ser Leu Ala Val
65                  70                  75                  80

Ala Asp Met Leu Val Ser Met Ser Ser Ala Trp Glu Thr Ile Thr Ile
                85                  90                  95

Tyr Leu Leu Asn Asn Lys His Leu Val Ile Ala Asp Ala Phe Val Arg
            100                 105                 110

His Ile Asp Asn Val Phe Asp Ser Met Ile Cys Ile Ser Val Val Ala
        115                 120                 125

Ser Met Cys Ser Leu Leu Ala Ile Ala Val Asp Arg Tyr Val Thr Ile
    130                 135                 140

Phe Tyr Ala Leu Arg Tyr His His Ile Met Thr Ala Arg Arg Ser Gly
145                 150                 155                 160
```

```
Ala Ile Ile Ala Gly Ile Trp Ala Phe Cys Thr Gly Cys Gly Ile Val
            165                 170                 175

Phe Ile Leu Tyr Ser Glu Ser Thr Tyr Val Ile Leu Cys Leu Ile Ser
            180                 185                 190

Met Phe Phe Ala Met Leu Phe Leu Leu Val Ser Leu Tyr Ile His Met
            195                 200                 205

Phe Leu Leu Ala Arg Thr His Val Lys Arg Ile Ala Leu Cys Pro Gly
            210                 215                 220

Pro Ala Leu Arg Gly Arg Gly Pro Ala Trp Gln Gly Ala Val Thr Val
225                 230                 235                 240

Thr Met Leu Leu Gly Val Phe Thr Val Cys Trp Ala Pro Phe Phe Leu
            245                 250                 255

His Leu Thr Leu Met Leu Ser Cys Pro Gln Asn Leu Tyr Cys Ser Arg
            260                 265                 270

Phe Met Ser His Phe Asn Met Tyr Leu Ile Leu Ile Met Cys Asn Ser
            275                 280                 285

Val Met Asp Pro Leu Ile Tyr Ala Phe Arg Ser Gln Glu Met Arg Lys
            290                 295                 300

Thr Phe Lys Glu Ile Ile Cys Cys Arg Gly Phe Arg Ile Ala Cys Ser
305                 310                 315                 320

Phe Pro Arg Arg Asp
            325
```

(2) INFORMATION FOR SEQ ID NO: 17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:17:

GGAAGCTTTC TTTGGTAGGC TG                                  22

(2) INFORMATION FOR SEQ ID NO: 18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 18:

GGTCTAGAGC CACAGAGAGG AG                                  22

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 19:

CTGCATTTCT TGGATCT                                           17

-continued (2) INFORMATION FOR SEQ ID NO: 20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 20:

AAGCTGCACA TGGATGC                                      17